United States Patent
Fodor et al.

(10) Patent No.: US 7,087,732 B2
(45) Date of Patent: *Aug. 8, 2006

(54) NUCLEOTIDES AND ANALOGS HAVING PHOTOREMOVABLE PROTECTING GROUPS

(75) Inventors: Stephen P. A. Fodor, Palo Alto, CA (US); Lubert Stryer, Stanford, CA (US); J. Leighton Read, Palo Alto, CA (US); Michael C. Pirrung, Durham, NC (US)

(73) Assignee: Affymetrix, Inc., Santa Clara, CA (US)

( * ) Notice: Subject to any disclaimer, the term of this patent is extended or adjusted under 35 U.S.C. 154(b) by 459 days.

This patent is subject to a terminal disclaimer.

(21) Appl. No.: 10/033,195

(22) Filed: Dec. 28, 2001

(65) Prior Publication Data

US 2003/0119008 A1   Jun. 26, 2003

Related U.S. Application Data

(60) Continuation of application No. 09/465,126, filed on Dec. 17, 1999, now Pat. No. 6,566,495, which is a continuation of application No. 09/063,933, filed on Apr. 21, 1998, now Pat. No. 6,600,031, and a continuation of application No. 08/466,632, filed on Jun. 6, 1995, now Pat. No. 5,744,305, and a continuation-in-part of application No. 08/456,887, filed on Jun. 1, 1995, now Pat. No. 6,406,844, which is a division of application No. 08/390,272, filed on Feb. 16, 1995, now Pat. No. 5,489,678, which is a division of application No. 07/954,646, filed on Sep. 30, 1992, now Pat. No. 5,445,934, which is a division of application No. 07/850,356, filed on Mar. 12, 1992, now Pat. No. 5,405,783, which is a continuation of application No. 07/624,120, filed on Dec. 6, 1990, now abandoned, which is a continuation-in-part of application No. 07/492,462, filed on Mar. 7, 1990, now Pat. No. 5,143,854, which is a division of application No. 07/492,462, filed on Mar. 7, 1990, now Pat. No. 5,143,854, which is a continuation-in-part of application No. 07/362,901, filed on Jun. 7, 1989, now abandoned.

(51) Int. Cl.
*C07H 21/00* (2006.01)
*C07H 21/02* (2006.01)
*C07H 21/04* (2006.01)

(52) U.S. Cl. .................. 536/22.1; 536/23.1; 536/24.3; 536/25.3; 536/25.31; 536/25.33

(58) Field of Classification Search .............. 536/22.1, 536/25.3, 25.31, 23.1, 24.3, 25.33
See application file for complete search history.

(56) References Cited

U.S. PATENT DOCUMENTS

| | | | |
|---|---|---|---|
| 3,642,450 A | 2/1972 | Eriksson | |
| 3,730,844 A | 5/1973 | Gilham et al. | 195/103.5 R |
| 3,849,137 A | 11/1974 | Barzynski et al. | 96/97 |
| 3,862,056 A | 1/1975 | Hartman | 252/511 |
| 3,939,350 A | 2/1976 | Kronick et al. | 250/365 |
| 4,072,576 A | 2/1978 | Arwin et al. | 195/103.5 R |
| 4,121,222 A | 10/1978 | Diebold et al. | 347/7 |
| 4,180,739 A | 12/1979 | Abu-Shumays | 250/461 R |
| 4,216,245 A | 8/1980 | Johnson | 427/2.13 |
| 4,238,757 A | 12/1980 | Schenck | 357/25 |
| 4,269,933 A | 5/1981 | Pazos | 430/291 |
| 4,314,821 A | 2/1982 | Rice | 23/230 B |
| 4,327,073 A | 4/1982 | Huang | 424/1 |
| 4,339,528 A | 7/1982 | Goldman | 430/323 |
| 4,342,905 A | 8/1982 | Fujii et al. | 250/201 |
| 4,373,071 A | 2/1983 | Itakura | 525/375 |
| 4,395,486 A | 7/1983 | Wilson et al. | 435/6 |
| 4,405,771 A | 9/1983 | Jagur | 528/266 |
| 4,444,878 A | 4/1984 | Paulus | 435/7 |
| 4,444,892 A | 4/1984 | Malmros | 436/528 |
| 4,448,534 A | 5/1984 | Wertz et al. | 356/435 |
| 4,458,066 A | 7/1984 | Caruthers et al. | 536/27 |
| 4,477,556 A | 10/1984 | Dueber et al. | |
| 4,478,967 A | 10/1984 | Eian et al. | |
| 4,483,920 A | 11/1984 | Gillespie et al. | 435/6 |
| 4,500,707 A | 2/1985 | Caruthers et al. | 536/27 |
| 4,500,919 A | 2/1985 | Schreiber | 358/78 |

| Patent | Date | Inventor | Class |
|---|---|---|---|
| 4,516,833 A | 5/1985 | Fusek | 350/162.12 |
| 4,517,338 A | 5/1985 | Urdea et al. | 525/54.11 |
| 4,533,682 A | 8/1985 | Tortorello et al. | 523/414 |
| 4,537,861 A | 8/1985 | Elings et al. | 436/518 |
| 4,542,102 A | 9/1985 | Dattagupta et al. | 435/6 |
| 4,555,490 A | 11/1985 | Merril | 436/86 |
| 4,556,643 A | 12/1985 | Paau et al. | 435/5 |
| 4,562,157 A | 12/1985 | Lowe et al. | 435/291 |
| 4,563,417 A | 1/1986 | Albarella et al. | |
| 4,563,419 A | 1/1986 | Ranki et al. | 435/6 |
| 4,569,967 A | 2/1986 | Kornreich et al. | 525/54.11 |
| 4,580,895 A | 4/1986 | Patel | 356/39 |
| 4,584,277 A | 4/1986 | Ullman | 436/501 |
| 4,588,682 A | 5/1986 | Groet et al. | 435/6 |
| 4,591,570 A | 5/1986 | Chang | 435/7.24 |
| 4,598,049 A | 7/1986 | Zelinka et al. | 422/116 |
| 4,613,566 A | 9/1986 | Potter | 435/6 |
| 4,624,915 A | 11/1986 | Schindler et al. | 435/4 |
| 4,626,684 A | 12/1986 | Landa | 250/328 |
| 4,631,211 A | 12/1986 | Houghten | 428/35 |
| 4,637,861 A | 1/1987 | Krull et al. | 204/1 T |
| 4,656,127 A | 4/1987 | Mundy | 435/6 |
| 4,670,380 A | 6/1987 | Dattagupta | 435/6 |
| 4,677,054 A | 6/1987 | White et al. | 435/6 |
| 4,681,859 A | 7/1987 | Kramer | 436/501 |
| 4,683,195 A | 7/1987 | Mullis et al. | 435/6 |
| 4,683,202 A | 7/1987 | Mullis | 435/91 |
| 4,689,405 A | 8/1987 | Frank et al. | 536/27 |
| 4,704,353 A | 11/1987 | Humphries et al. | 435/4 |
| 4,711,955 A | 12/1987 | Ward et al. | 536/29 |
| 4,713,326 A | 12/1987 | Dattagupta et al. | 435/6 |
| 4,713,347 A | 12/1987 | Mitchell et al. | 436/501 |
| 4,715,413 A | 12/1987 | Backlund et al. | 141/94 |
| 4,715,929 A | 12/1987 | Ogawa | |
| 4,716,106 A | 12/1987 | Chiswell | 435/6 |
| 4,719,179 A | 1/1988 | Barany | 435/172.1 |
| 4,719,615 A | 1/1988 | Feyrer et al. | 369/284 |
| 4,722,906 A | 2/1988 | Guire | 436/501 |
| 4,728,502 A | 3/1988 | Hamill | 422/116 |
| 4,728,591 A | 3/1988 | Clark et al. | 430/5 |
| 4,731,325 A | 3/1988 | Palva et al. | 435/6 |
| 4,737,344 A | 4/1988 | Koizumi et al. | 422/100 |
| 4,755,458 A | 7/1988 | Rabbani et al. | 435/5 |
| 4,758,727 A | 7/1988 | Tomei et al. | |
| 4,762,881 A | 8/1988 | Kauer | 525/54.11 |
| 4,766,062 A | 8/1988 | Diamond et al. | 435/6 |
| 4,767,700 A | 8/1988 | Wallace | 435/6 |
| 4,777,019 A | 10/1988 | Dandekar | 422/68 |
| 4,780,504 A | 10/1988 | Buendia et al. | 525/54.11 |
| 4,786,170 A | 11/1988 | Groebler | 356/318 |
| 4,786,684 A | 11/1988 | Glass | 525/54.1 |
| 4,794,150 A | 12/1988 | Steel | 525/54.11 |
| 4,808,508 A | 2/1989 | Platzer | 430/143 |
| 4,810,869 A | 3/1989 | Yabe et al. | 250/201 |
| 4,811,062 A | 3/1989 | Tabata et al. | 356/152 |
| 4,811,218 A | 3/1989 | Hunkapiller et al. | 204/461 |
| 4,812,512 A | 3/1989 | Buendia et al. | 525/54.11 |
| 4,820,630 A | 4/1989 | Taub | 435/5 |
| 4,822,566 A | 4/1989 | Newman | 422/68 |
| 4,833,092 A | 5/1989 | Geysen | 436/501 |
| 4,844,617 A | 7/1989 | Kelderman et al. | 356/372 |
| 4,846,552 A | 7/1989 | Veldkamp et al. | 350/162.2 |
| 4,849,513 A | 7/1989 | Smith et al. | 536/27 |
| 4,855,225 A | 8/1989 | Fung et al. | 435/6 |
| 4,865,990 A | 9/1989 | Stead et al. | 435/803 |
| 4,868,103 A | 9/1989 | Stavrianopoulos et al. | 435/5 |
| 4,874,500 A | 10/1989 | Madou et al. | 204/412 |
| 4,877,745 A | 10/1989 | Hayes et al. | 436/166 |
| 4,886,741 A | 12/1989 | Schwartz | 435/5 |
| 4,888,278 A | 12/1989 | Singer et al. | 435/6 |
| 4,921,805 A | 5/1990 | Gebeyehu et al. | 435/270 |
| 4,923,901 A | 5/1990 | Koester et al. | 521/53 |
| 4,925,785 A | 5/1990 | Wang et al. | 435/6 |
| 4,931,384 A | 6/1990 | Layton et al. | 435/7.31 |
| 4,946,942 A | 8/1990 | Fuller et al. | 530/335 |
| 4,965,188 A | 10/1990 | Mullis et al. | 435/6 |
| 4,973,493 A | 11/1990 | Guire | 427/2 |
| 4,979,959 A | 12/1990 | Guire | 623/66 |
| 4,981,783 A | 1/1991 | Augenlicht | 435/6 |
| 4,981,985 A | 1/1991 | Kaplan et al. | 556/50 |
| 4,984,100 A | 1/1991 | Takayama et al. | 360/49 |
| 4,987,065 A | 1/1991 | Stavrianopoulos et al. | 435/5 |
| 4,988,617 A | 1/1991 | Landegren et al. | 435/6 |
| 4,992,383 A | 2/1991 | Farnsworth | 436/89 |
| 4,994,373 A | 2/1991 | Stavrianopoulos et al. | 435/6 |
| 4,996,142 A | 2/1991 | Al-Hakim et al. | |
| 5,002,867 A | 3/1991 | Macevicz | 435/6 |
| 5,006,464 A | 4/1991 | Chu et al. | 435/7.1 |
| 5,011,770 A | 4/1991 | Kung et al. | 435/6 |
| 5,013,669 A | 5/1991 | Peters, Jr. et al. | 436/518 |
| 5,021,550 A | 6/1991 | Zeiger | 530/334 |
| 5,026,773 A | 6/1991 | Steel | 525/54.11 |
| 5,026,840 A | 6/1991 | Dattagupta et al. | 536/27 |
| 5,028,525 A | 7/1991 | Gray et al. | 435/6 |
| 5,028,545 A | 7/1991 | Soini | 436/501 |
| 5,037,882 A | 8/1991 | Steel | 525/54.11 |
| 5,043,265 A | 8/1991 | Tanke et al. | 435/6 |
| 5,047,524 A | 9/1991 | Andrus et al. | 536/27 |
| 5,064,754 A | 11/1991 | Mills | 435/6 |
| 5,077,085 A | 12/1991 | Schnur et al. | 427/98 |
| 5,077,210 A | 12/1991 | Eigler et al. | 435/176 |
| 5,079,600 A | 1/1992 | Schnur et al. | 357/4 |
| 5,081,584 A | 1/1992 | Omichinski et al. | 364/497 |
| 5,082,830 A | 1/1992 | Brakel et al. | 514/44 |
| 5,091,652 A | 2/1992 | Mathies et al. | 250/458.1 |
| 5,096,807 A | 3/1992 | Leaback | 435/6 |
| 5,100,626 A | 3/1992 | Levin | 422/100 |
| 5,100,777 A | 3/1992 | Chang | 435/7.24 |
| 5,112,962 A | 5/1992 | Letsinger et al. | 536/27 |
| 5,141,813 A | 8/1992 | Nelson | 428/402 |
| 5,143,854 A | 9/1992 | Pirrung et al. | 436/518 |
| 5,149,625 A | 9/1992 | Church et al. | 435/6 |
| 5,153,319 A | 10/1992 | Caruthers et al. | 536/27 |
| 5,164,319 A | 11/1992 | Hafeman et al. | 435/287.1 |
| 5,171,695 A | 12/1992 | Ekins | 436/501 |
| 5,188,963 A | 2/1993 | Stapleton | 435/288.3 |
| 5,192,980 A | 3/1993 | Dixon et al. | 356/326 |
| 5,200,051 A | 4/1993 | Cozzette et al. | 204/403 |
| 5,202,231 A | 4/1993 | Drmanac et al. | 435/6 |
| 5,206,137 A | 4/1993 | Ip et al. | 435/6 |
| 5,215,882 A | 6/1993 | Bahl et al. | 435/6 |
| 5,215,889 A | 6/1993 | Schultz | 435/41 |
| 5,219,726 A | 6/1993 | Evans | 435/6 |
| 5,225,326 A | 7/1993 | Bresser et al. | 435/6 |
| 5,232,829 A | 8/1993 | Longiaru et al. | 435/6 |
| 5,235,028 A | 8/1993 | Barany et al. | 528/335 |
| 5,242,974 A | 9/1993 | Holmes | 525/54.11 |
| 5,252,743 A | 10/1993 | Barrett et al. | 548/303.7 |
| 5,256,549 A | 10/1993 | Urdea et al. | 435/91 |
| 5,258,506 A | 11/1993 | Urdea et al. | 536/23.1 |
| 5,306,641 A | 4/1994 | Saccocio | 436/85 |
| 5,310,893 A | 5/1994 | Erlich et al. | 536/24.31 |
| 5,324,633 A | 6/1994 | Fodor et al. | 435/6 |
| 5,328,824 A | 7/1994 | Ward et al. | 435/6 |
| 5,348,855 A | 9/1994 | Dattagupta et al. | 435/6 |
| 5,384,261 A | 1/1995 | Winkler et al. | 436/518 |
| 5,405,783 A | 4/1995 | Pirrung et al. | 436/518 |
| 5,412,087 A | 5/1995 | McGall et al. | |
| 5,424,186 A | 6/1995 | Fodor et al. | 435/6 |
| 5,424,188 A | 6/1995 | Schneider et al. | 435/6 |
| 5,432,099 A | 7/1995 | Ekins | 436/518 |
| 5,436,327 A | 7/1995 | Southern et al. | 536/25.34 |
| 5,445,934 A | 8/1995 | Fodor et al. | 435/6 |
| 5,447,841 A | 9/1995 | Gray et al. | 435/6 |
| 5,474,796 A | 12/1995 | Brennan | 427/2.13 |
| 5,486,452 A | 1/1996 | Gordon et al. | 435/5 |

| | | | | | |
|---|---|---|---|---|---|
| 5,489,507 A | 2/1996 | Chehab .................. 435/6 | EP | 174 879 | 3/1986 |
| 5,489,678 A | 2/1996 | Fodor et al. ............ 536/22.1 | EP | 194 132 | 9/1986 |
| 5,492,806 A | 2/1996 | Drmanac et al. ............ 435/5 | EP | 194132 | 9/1986 |
| 5,494,810 A | 2/1996 | Barany et al. ........... 435/91.52 | EP | 228 075 | 7/1987 |
| 5,510,270 A | 4/1996 | Fodor et al. ............ 436/518 | EP | 0233 403 B1 | 8/1987 |
| 5,525,464 A | 6/1996 | Drmanac et al. ............ 435/6 | EP | 245 662 | 11/1987 |
| 5,527,681 A | 6/1996 | Holmes ................ 435/6 | EP | 0266 881 A3 | 5/1988 |
| 5,552,270 A | 9/1996 | Khrapko et al. ............ 435/6 | EP | 268 237 | 5/1988 |
| 5,556,961 A | 9/1996 | Foote et al. ............ 536/27.1 | EP | 130 523 | 6/1988 |
| 5,561,071 A | 10/1996 | Hollenberg et al. ........... 437/1 | EP | 281 927 | 9/1988 |
| 5,569,584 A | 10/1996 | Augenlicht ............ 435/6 | EP | 228 310 | 10/1988 |
| 5,571,639 A | 11/1996 | Hubbell et al. ............ 430/5 | EP | 288 310 | 10/1988 |
| 5,593,839 A | 1/1997 | Hubbell et al. ............ 435/6 | EP | 304 202 | 2/1989 |
| 5,599,720 A | 2/1997 | Ekins ................ 436/501 | EP | 307 476 | 3/1989 |
| 5,604,099 A | 2/1997 | Erlich et al. ............ 435/6 | EP | 319 012 | 6/1989 |
| 5,643,728 A | 7/1997 | Slater et al. ............ 435/6 | EP | 328 256 | 8/1989 |
| 5,653,939 A | 8/1997 | Hollis et al. ............ 422/50 | EP | 333 561 | 9/1989 |
| 5,667,667 A | 9/1997 | Southern ............ 205/687 | EP | 337 498 | 10/1989 |
| 5,667,972 A | 9/1997 | Drmanac et al. ............ 435/6 | EP | 386 229 | 4/1990 |
| 5,688,642 A | 11/1997 | Chrisey et al. | EP | 373 203 | 6/1990 |
| 5,695,940 A | 12/1997 | Drmanac et al. ............ 435/6 | EP | 392 546 | 10/1990 |
| 5,698,393 A | 12/1997 | Macioszek et al. ............ 435/5 | EP | 142 299 | 12/1990 |
| 5,700,637 A | 12/1997 | Southern ............ 435/6 | EP | 0400 920 B1 | 12/1990 |
| 5,707,806 A | 1/1998 | Shuber ................ 435/6 | EP | 173 339 | 1/1992 |
| 5,744,305 A | 4/1998 | Fodor et al. ............ 435/6 | EP | 171 150 | 3/1992 |
| 5,753,788 A * | 5/1998 | Fodor et al. ............ 536/22.1 | EP | 237 362 | 3/1992 |
| 5,776,737 A | 7/1998 | Dunn ................ 435/91.1 | EP | 185 547 | 6/1992 |
| 5,777,888 A | 7/1998 | Rine et al. ............ 364/496 | EP | 260 634 | 6/1992 |
| 5,800,992 A | 9/1998 | Fodor et al. ............ 435/6 | EP | 232 967 | 4/1993 |
| 5,807,522 A | 9/1998 | Brown et al. ............ 422/50 | EP | 235 726 | 5/1993 |
| 5,810,989 A | 9/1998 | Krihak et al. | EP | 476 014 | 8/1994 |
| 5,830,645 A | 11/1998 | Pinkel et al. ............ 435/6 | EP | 225 807 | 10/1994 |
| 5,837,832 A | 11/1998 | Chee et al. | EP | 717 113 | 6/1996 |
| 5,837,859 A | 11/1998 | Teoule et al. | EP | 721 016 | 7/1996 |
| 5,843,767 A | 12/1998 | Beattie ............ 435/287.1 | EP | 535 242 | 9/1997 |
| 5,846,708 A | 12/1998 | Hollis et al. ............ 435/6 | EP | 848 067 | 6/1998 |
| 5,869,237 A | 2/1999 | Ward et al. ............ 435/6 | EP | 619 321 | 1/1999 |
| 5,871,697 A | 2/1999 | Rothberg et al. ............ 422/68.1 | FR | 2559783 | 3/1988 |
| 5,889,165 A * | 3/1999 | Fodor et al. ............ 536/22.1 | GB | 2156074 | 3/1988 |
| 5,922,534 A | 7/1999 | Lichtenwalter | GB | 2196476 | 4/1988 |
| 5,972,619 A | 10/1999 | Drmanac et al. ............ 435/6 | GB | 8810400.5 | 5/1988 |
| 6,018,041 A | 1/2000 | Drmanac et al. ............ 536/24.3 | GB | 2233654 | 1/1991 |
| 6,025,136 A | 2/2000 | Drmanac et al. ............ 435/6 | GB | 2248840 | 9/1992 |
| 6,040,166 A | 3/2000 | Erlich et al. ............ 435/194 | JP | 49-110601 | 10/1974 |
| 6,054,270 A | 4/2000 | Southern ............ 435/6 | JP | 60-248669 | 12/1985 |
| 6,093,302 A | 7/2000 | Montgomery | JP | 63-084499 | 4/1988 |
| 6,171,797 B1 | 1/2001 | Perbost | JP | 63-223557 | 9/1988 |
| 6,210,894 B1 | 4/2001 | Brennan | JP | 1-233447 | 9/1989 |
| 6,221,653 B1 | 4/2001 | Caren et al. | JP | 01233447 | 9/1989 |
| 6,225,625 B1 | 5/2001 | Pirrung et al. | NO | P 913186 | 8/1991 |
| 6,235,483 B1 | 5/2001 | Wolber et al. | WO | WO 84/03151 | 8/1984 |
| 6,255,053 B1 | 7/2001 | Lichtenwalter | WO | WO 84/03564 | 9/1984 |
| 6,261,776 B1 | 7/2001 | Pirrung et al. | WO | WO 85/01051 | 3/1985 |
| 6,291,183 B1 | 9/2001 | Pirrung et al. | WO | WO 86/00991 | 2/1986 |
| 6,310,189 B1 * | 10/2001 | Fodor et al. ............ 536/22.1 | WO | WO 86/06487 | 11/1986 |
| 6,346,423 B1 | 2/2002 | Schembri | WO | WO 87/05942 | 10/1987 |
| 6,458,583 B1 | 10/2002 | Bruhn et al. | WO | WO 88/01058 | 2/1988 |
| 2002/0064796 A1 | 5/2002 | Stryer et al. | WO | WO 88/04777 | 6/1988 |
| | | | WO | WO 89/05616 | 6/1989 |
| | FOREIGN PATENT DOCUMENTS | | WO | WO 89/08834 | 9/1989 |
| | | | WO | WO 89/10977 | 11/1989 |
| CA | 1284931 | 6/1991 | WO | WO 89/11548 | 11/1989 |
| DE | 2242394 | 3/1974 | WO | WO 89/12819 | 12/1989 |
| DE | 2612 359 A1 | 3/1976 | WO | WO 90/00626 | 1/1990 |
| DE | 3440141 | 5/1986 | WO | WO 90/00887 | 2/1990 |
| DE | 3505287 | 3/1988 | WO | WO 90/15070 | 2/1990 |
| DE | 4013 588 A1 | 4/1990 | WO | WO 90/03382 | 4/1990 |
| EP | 046 083 | 2/1982 | WO | WO 90/04652 | 5/1990 |
| EP | 0046 430 A1 | 2/1982 | WO | WO 90/05789 | 5/1990 |
| EP | 088 636 | 9/1983 | WO | WO 90/07582 | 7/1990 |
| EP | 103 197 | 3/1984 | WO | WO 9015070 | 12/1990 |
| EP | 127 438 | 12/1984 | WO | WO 91/00868 | 1/1991 |
| EP | 063 810 | 3/1986 | WO | WO 91/04266 | 4/1991 |

| WO | WO 91/07087 | 5/1991 |
| WO | WO 92/16655 | 1/1992 |
| WO | WO 92/10092 | 6/1992 |
| WO | WO 92/10588 | 6/1992 |
| WO | WO 93/02992 | 2/1993 |
| WO | WO 93/09668 | 5/1993 |
| WO | WO 88/01302 | 6/1993 |
| WO | WO 93/11262 | 6/1993 |
| WO | WO 93/17126 | 9/1993 |
| WO | WO 93/22456 | 11/1993 |
| WO | WO 93/22480 | 11/1993 |
| WO | WO 93/22680 | 11/1993 |
| WO | WO 95/00530 | 1/1995 |
| WO | WO 95/11995 | 5/1995 |
| WO | WO 95/33846 | 12/1995 |
| WO | WO 96/23078 | 8/1996 |
| WO | WO 97/10365 | 3/1997 |
| WO | WO 97/17317 | 5/1997 |
| WO | WO 97/19410 | 5/1997 |
| WO | WO 97/27317 | 7/1997 |
| WO | WO 97/29212 | 8/1997 |
| WO | WO 97/31256 | 8/1997 |
| WO | WO 97/45559 | 12/1997 |
| WO | WO 98/03673 | 1/1998 |
| WO | WO 98/31836 | 7/1998 |
| YU | P-570/87 | 4/1987 |
| YU | 18617/87 | 9/1987 |

OTHER PUBLICATIONS

Sequencing by Hybridization Workshop, listing of participants and workshop presentation summaries (1991).
"A Sequencing Reality Check," *Science*, 242:1245 (1988).
"Affymax raises $25 million to develop high-speed drug discovery system," *Biotechnology News*, 10(3):7-8 (1990).
"Preparation of fluorescent-labeled DNA and its use as a probe in molecular hybridization," *Bioorg Khim*, 12(11):1508-1513 (1986).
Abbott et al., "Manipulation of the Wettability of Surfaces on the 0.1—to 1 -Micrometer Scale Through Micromaching and Molecular Self-Assembly," *Science*, 257:1380-1382 (1992).
Adams et al., "Complementary DNA Sequencing: Expressed Sequence Tags and Human Genome Project," *Science*, 252(5013):1651-1656 (1991).
Adams et al., "Photolabile Chelators That "Cage" Calcium with Improved Speed of Release and Pre-Photolysis Affinity," *J. Gen. Physiol.*, p. 9a (Dec. 1986).
Adams et al., "Biologically Useful Chelators That Take Up Ca2+ upon Illumination," *J. Am. Chem. Soc.*, 111:7957-7968 (1989).
Ajayaghosh et al., "Solid-Phase Synthesis of N-Methyl- and N-Ethylamides of Peptides Using Photolytically Detachable ((3-Nitro-4((alkylamino)methyl)benzamido)methyl)polystyrene Resin," *J. Org.Chem.*, 55(9):2826-2829 (1990).
Ajayaghosh et al., "Solid-phase synthesis of C-terminal peptide amides using a photoremovable α-methylphenacylamido anchoring linkage," *Proc. Ind. Natl. Sci (Chem.Sci.)*, 100(5):389-396 (1988).
Ajayaghosh et al., "Polymer-supported Solid-phase Synthesis of C-Terminal Peptide N-Methylamides Using a Modified Photoremovable 3-Nitro-4-N-methylaminomethyl-polystyrene Support," *Ind.J.Chem.*, 27B:1004-1008 (1988).
Ajayaghosh et al., "Polymer-Supported Synthesis of Protected Peptide Segments on a Photosensitive o-Nitro(α-Methyl)Bromobenzyl Resin," *Tetrahedron*, 44(21):6661-6666 (1988).

Amit et al., "Photosensitive Protecting Groups of Amino Sugars and Their Use in Glycoside Synthesis. 2-Nitrobenzyloxycarbonylamino and 6-Nitrovcratryloxycarbonylamino Derivatives," *J.Org. Chem*, 39(2):192-196 (1974).
Amit et al., "Photosensitive Protecting Groups—A Review," *Israel J. Chem.*, 12(1-2):103-113 (1974).
Anand et al., "A 3.5 genome equivalent multi access YAC library: construction, characterisation, screening and storage," *Nuc. Acids Res.*, 18(8):1951-1956 (1990).
Anderson et al., "Quantitative Filter Hybridisation," chapter 3 from *Nucleic Acid Hybridization a practical approach*, pp. 73-111, Hames et al., eds., IRL Press (1985).
Applied Biosystems, Model 431A Peptide Synthesizer User's manual, Sections 2 and 6, (Aug. 15, 1989).
Arnold et al., "A Novel Universal Support for DNA & RNA Synthesis," abstract from *Federation Proceedings*, 43(7): abstract No. 3669 (1984).
Atherton et al., Solid Phase Peptide Synthesis: A Practical Approach, IRL Press, (1989), tb1. of cont., pp. vii-ix.
Augenlicht et al., "Cloning and Screening of Sequences Expressed in a Mouse Colon Tumor," *Cancer Research*, 42:1088-1093 (1982).
Augenlicht et al., "Expression of Cloned Sequences in Biopsies of Human Colonic Tissue and in Colonic Carcinoma Cells Induced to Differentiate *in Vitro,*" *Cancer Res.*, 47:6017-6021 (1987).
Bains, W., "Hybridization Methods for DNA Sequencing," *Genomics*, 11(2):294-301 (1991).
Bains et al., "A Novel Method for Nucleic Acid Sequence Determination," *J. Theor.Biol.*, 135:303-307 (1988).
Bains, W., "Alternative Routes Through the Genome," *Biotechnology*, 8:1251-1256 (1988).
Balachander et al., "Functionalized Siloxy-Anchored Monolayers with Exposed Amino, Azido, Bromo, or Cyano Groups," *Tetrahed. Ltrs.*, 29(44):5593-5594 (1988).
Baldwin et al., "New Photolabile Phosphate Protecting Groups," *Tetrahed.*, 46(19):6879-6884 (1990).
Bannwarth et al., "Laboratory Methods, A System for the Simultaneous Chemical synthesis of Different DNA Fragments on Solid Support," *DNA*, 5(5):413-419 (1986).
Bannwarth, W., "Gene Technology: a Challenge for a Chemist," *CHIMIA*, 41(9):302-317 (1987).
Barany, F., "Genetic disease detection and DNA amplification using cloned thermostable ligase," *PNAS*, 88:189-193 (1991).
Barltrop et al., "Photosensitive Protective Groups," *Chemical Communications*, pp. 822-823 (1966).
Baringa, M., "Will 'DNA Chip' Speed Genome Initiative," *Science*, 253:1489 (1985).
Bart et al., "Microfabricated Electrohydrodynamic Pumps," *Sensors and Actuators*, A21-A23:193-197 (1990).
Bartsh et al., "Cloning of mRNA sequences from the human colon: Preliminary characterisation of defined mRNAs in normal and neoplastic tissues," *Br.J.Can.*, 54:791-798 (1986).
Baum, R., "Fledgling firm targets drug discovery process," *Chem. Eng. News*, p. 10-11 (1990).
Beltz et al., "Isolation of Multigene Families and Determination of Homologies by Filter Hybridization Methods," *Methods in Enzymology*, 100:266-285 (1983).
Benschop, Chem. Abstracts 114(26):256643 (1991).
Bhatia et al., "New Approach To Producing Patterned Biomolecular Assemblies," *J. American Chemical Society*, 114:4432-4433 (1992).

Biorad Chromatography Electrophoresis Immunochemistry Molecular Biology HPLC catalog M 1987 pp. 182.

Blawas et al., "Step-and-Repeat Photopatterning of Protein Features Using Caged-Biotin-BSA: Characterization and Resolution," *Langmuir*, 14(15):4243-4250 (1998).

Blawas, A.S., "Photopatterning of Protein Features using Caged-biotin-Bovine Serum Albumin," dissertation for ph.D at Duke University in 1998.

Bos et al., "Amino-acid substirutions at codon 13 of the N-ras oncogene in human acute myeloid leukaemia," *Nature*, 315:726-730 (1985).

Boyle et al., "Differential distribution of long and short interspersed element sequences in the mouse genome: Chromosome karyotyping by fluorescence in situ hybridization," *PNAS*, 87:7757-7761 (1990).

Brock et al., "Rapid flurorescence detection of in situ hybridization with biotinylated bovine herpesvirus-1 DNA probes," *J. Veterinary Diagnostic Invest.*, 1:34-38 (1989).

Burgi et al., "Optimization in Sample Stacking for High-Performance Capillary Electrophoresis," *Anal. Chem.*, 63:2042-2047 (1991).

Cameron et al., "Photogeneration of Organic Bases from o-Nitrobenzyl-Derived Carbamates," *J. Am. Chem. Soc.*, 113:4303-4313 (1991).

Carrano et al., "A High-Resolution, Fluorescence-Based, Semiautomated Method for DNA Fingerprinting," *Genomics*, 4:129-136 (1989).

Caruthers, M.H., "Gene Synthesis Machines: DNA Chemistry and Its Uses," *Science*, 230:281-285 (1985).

Chatterjee et al., "Inducible Alkylation of DNA Using an Oligonucleotide-Quinone Conjugate," *Am. J. Chem. Soc.*, 112:6397-6399 (1990).

Chee et al., "Accessing Genetic Information with High-Density DNA Arrays,"*Science*, 274:610-614 (1996).

Chehab et al., "Detection of sicle cell anaemia mutation by colour DNA amplification," *Lancet*, 335:15-17 (1990).

Chehab et al., "Detection of specific DNA sequences by fluorescence amplification: A color complementation assay," *PNAS*, 86:9178-9182 (1989).

Chetverin et al., "Oligonucleotide Arrays: New Concepts and Possibilities," *Biotechnology*, 12:1093-1099 (1994).

Church et al., "Multiplex DNA sequencing," *Science*, 240:185-188 (1988).

Church et al., "Genomic sequencing," *PNAS*, 81:1991-1995 (1984).

Clevite Corp., Piezoelectric Technology, Data for Engineers.

Corbett et al., "Reaction of Nitroso Aromatics with Glyoxylic Acid. A New Path to Hydroxamic Acids," *J. Org. Chem.*, 45:2834-2839 (1980).

Coulson et al., "Toward a physical map of the genome of the nematode *Caenorhabditis elegans,*" *PNAS*, 83:7821-7825 (1986).

Craig et al., "Ordering of cosmid clones covering the Herpes simplex virus type 1 (HSV-1) genome: a test case for fingerprinting by hybridization," *Nuc. Acid. Res.*, 18(9):2653-2660 (1990).

Cummings et al., "Photoactivable Fluorophores. 1. Synthesis and Photoactivation of o-Nitrobenzyl-Quenched Fluorescent Carbamates," *Tetrahedron Letters*, 29(1):65-68 (1988).

Dattagupta et al., "Rapid identification of Microorganisms by Nucleic Acid Hybridization after Labeling the Test Sample," *Anal. Biochem.*, 177:85-89 (1989).

Dattagupta et al., "Nucleic Acid Hybridization: a Rapid Method for the Diagnosis of Infectious Diseases," *Perspectives in Antiinfective Therapy*, eds. Jackson et al., pp. 241-247 (1988).

Dower et al., "The Search for Molecular Diversity (II): Recombinant and Synthetic Randomized Peptide Libraries," *Ann. Rep. Med. Chem.*, 26:271-280 (1991).

Diggelmann, "Investigating the VLSIPS synthesis process," Sep. 9, 1994.

Di Mauro et al., "DNA Technology in Chip Construction," *Adv. Mater.*, 5(5):384-386 (1993).

Drmanac et al., "An Algorithm for the DNA Sequence Generation from k-Tuple Word Contents of the Minimal Number of Random Fragments," *J. Biomol. Struct. Dyn.*, 8(5):1085-1102 (1991).

Drmanac et al., "Partial Sequencing by Oligo-Hybridization Concept and Applications in Genome Analysis," 1st Int. Conf. Electrophor., Supercomp., Hum. Genome pp. 60-74 (1990).

Drmanac et al., "Sequencing by Oligonucleotide Hybridization: A Promising Framework in Decoding of the Genome Program?," 1st Int. Conf. Electrophor., Supercomp., Hum. Genome pp. 47-59 (1990).

Drmanac et al., "Laboratory Methods, Reliable Hybridization of Oligonucleotides as Short as Six Nucleotides," *DNA and Cell Biol.*, 9(7):527-534 (1990).

Drmanac et al., "Sequencing of *Megabase Plus DNA by Hybridization: theory of the Method,*" *Genomics*, 4:114-128 (1989).

Dramanac et al., "Sequencing of Megabase Plus DNA by Hybridization: Theory of the Method," abstract of presentation given at Cold Spring Harbor Symposium on Genome Mapping and Sequencing, Apr. 27, 1988 thru May 1, 1988.

Dulcey et al., "Deep UV Photochemistry of Chemisorbed Monolayers: Patterned Coplanar Molecular Assemblies," *Science*, 252:551-554 (1991).

Duncan et al., "Affinity Chromatography of a Sequence-Specific DNA Binding Protein Using Teflon-Linked Oligonucleotides," *Analytical Biochemistry*, 169:104-108 (1988).

Effenhauser et al., "Glass Chips for High-speed Capillary Electrophoresis Separations with Submicrometer Plate Heights," *Anal. Chem.*, 65:2637-2642 (1993).

Effenhauser et al., "High-Speed Separation of Antisense Oligonucleotides on a Micromachined Capillary Electrophoresis Device," *Anal. Chem.*, 66:2949-2953 (1994).

Ekins et al., "High Specific Activity Chemiluminescent and Fluorescent Markers: their Potential Application to High Sensitivity and 'Multi-analyte' Immunoassays," *J. Bioluminescence Chemiluminescence*, 4:59-78 (1989).

Ekins et al., "Development of Microspot Multi-Analyte Ratiometric Immunoassay Using dual Fluorescent-Labelled Antibodies," *Anal. Chemica Acta*, 227:73-96 (1989).

Ekins et al., "Multianalyte Microspot Immunoassay-Microanalytical 'Compact Disk' of the Future," *Clin. Chem.*, 37(11):1955-1967 (1991).

Ekins, R.P., "Multi-Analyte immunoassay*," *J. Pharmaceut. Biomedical Analysis*, 7(2):155-168 (1989).

Ekins et al., "Fluorescence Spectroscopy and its Application to a New Generation of High Sensitivity, Multi-Microspot, Multianalyte, Immunoassay," *Clin. Chim. Acta*, 194:91-114 (1990).

Elder, J.K., "Analysis of DNA Oligonucleotide Hybridization Data by Maximum Entropy," in *Maximum Entropy and Bayesian Methods*, eds. Mohammad-Djafari and Demoment, Kluwer, Dordrecht, pp. 363-371 (1992).

Ellis, R.W., "The Applications of Synthetic Oligonucleotides to Molecular Biology," *Pharmaceutical Research*, 3(4):195-207 (1986).

Evans et al., "Microfabrication for Automation of Molecular processes in Human Genome Analysis," *Clin. Chem.*, 41(11):1681 (1995).

Evans et al., "Physical mapping of complex genomes by cosmid multiplex analysis," *PNAS*, 86:5030-5034 (1989).

Ezaki et al., "Small-Scale DNA Preparation for Rapid Genetic Identification of *Campylobacter* Species without Radioisotope," *Microbiol. Immunology*, 32(2):141-150 (1988).

Fan et al., "Mapping small DNA sequences by fluorescence *in situ* hybridization directly on banded metaphase chromosomes," *PNAS*, 87(16):6223-6227 (1990).

Fan et al., "Micromachining of Capillary Electrophoresis Injectors and Separators on Glass Chips and Evaluation of Flow at Capillary Intersections," Anal. Chem., 66:177-184 (1994).

Feinberg et al., ADDENDUM to "A technique for Radiolabeling DNA Restriction Endonuclease Fragments to High Specific Activity," *Anal. Biochem.*, 137:266-267 (1984).

Fettinger et al., "Stacked modules for micro flow systems in chemical analysis: concept and studies using an enlarged model," *Sensors and Actuators*, B17:19-25 (1993).

Flanders et al., "A new interferometric alignment techique," *App. Phys. Ltrs.*, 31(7):426-429 (1977).

Fodor et al., "Multiplexed biochemical assays with biological chips," *Nature*, 364:555-556 (1993).

Fodor et al., "Light-directed, Spatially Addressable Parallel Chemical Synthesis," *Science*, 251:767-773 (1991).

Forman et al., "Thermodynamics of Duplex Formation and Mismatch Discrimination on Photolithographically Synthesized Oligonucleotide Arrays," chapter 13pp. 206-228 from *Molecular Modeling of Nucleic Acids*, ACS Symposium Series 682, Apr. 13-17, 1997, Leontis et al., eds.

Frank et al., "Simultaneous Multiple Peptide Synthesis Under Continuous flow Conditions on Cellulose Paper Discs as Segmental Solid Supports," *Tetrahedron*, 44(19):6031-6040 (1988).

Frank et al., "Automation of DNA Sequencing Reactions and Related Techniques: A Workstation for Micromanipulation of Liquids," *Bio/Technology*, 6:1211-1212 (1988).

Frank et al., "Simultaneous Synthesis and Biological Applications of DNA Fragments: An Efficient and Complete Methodology," *Methods in Enzymology*, 154:221-250 (1987).

Fuhr et al., "Travelling wave-drive microfabricated electrohydrodynamic pumps for liquids," *J. Micromech. Microeng.*, 4:217-226 (1994).

Fuller et al., "Urethane-Protected Amino Acid N-Carboxy Anhydrides and Their Use in Peptide Synthesis," *J. Amer. Chem. Soc.*, 112(20):7414-7416 (1990).

Furka et al., "General method for rapid synthesis of multicomponent peptide mixtures," *Int. J. Peptide Protein Res.*, 37:487-493 (1991).

Furka et al., "Cornucopia of Peptides by Synthesis," 14th Int. Congress of Biochem. abst.# FR:013, Jul. 10-15, 1988 Prague, Czechoslovakia.

Furka et al., "More Peptides by Less Labour," abst. 288, Int. Symp. Med. Chem., Budapest Hungary Aug. 15-19, 1988.

Gait, eds ., pp. 1-115 from *Oligonucleotide Synthesis: A Practical Approach*, IRL Press, (1984).

Gazard et al., "Lithographic Technique Using Radiation-Induced Grafting of Acrylic Acid into Poly(Methyl Methacrylate) Films," *Polymer Engineering and Science*, 20(16):1069-1072 (1980).

Gergen et al., "Filter replicas and permanent collections of recombinant DNA plasmids," *Nuc. Acids Res.*, 7(8):2115-2137 (1979).

Getzoff et al., "Mechanisms of Antibody Binding to a Protein," *Science*, 235:1191-1196 (1987).

Geysen et al., "Strategies for epitope analysis using peptide synthesis," *J. Immunol. Meth.*, 102:259-274 (1987).

Geysen et al., "Use of peptide synthesis to probe viral antigens for epitopes to a resolution of a single amino acid," *PNAS*, 81:3998-4002 (1984).

Geysen et al., "A synthetic strategy for epitope mapping," from Peptides:Chem. & Biol., Proc. of 10th Am. Peptide Symp., May 23-28, 1987, pp. 519-523, (1987).

Geysen, "Antigen-antibody interactions at the molecular level: adventures in peptide synthesis," *Immunol. Today*, 6(12):364-369 (1985).

Geysen et al., "Cognitive Features of Continuous Antigenic Determinants," from Synthetic Peptides: Approaches to Biological Probes, pp. 19-30, (1989).

Geysen et al., "Chemistry of Antibody Binding to a Protein," *Science*, 235:1184-1190 (1987).

Geysen et al., "The delineation of peptides able to mimic assembled epitopes," 1986 CIBA Symp., pp. 130-149.

Geysen et al., "Cognitive Features of Continuous Antigenic Determinants," *Mol. Recongnit.*, 1(1):1-10 (1988).

Geysen et al., "*A Prio Ri* Delineation of a Peptide Which Mimics A Discontinuous Antigenic Determinant," *Mol. Immunol.*, 23(7):709-715 (1986).

Ghosh et al., "Covalent attachment of oligonucleotides to solid supports," *Nuc. Acids Res.*, 15(13):5353-5373 (1987).

Gilon et al., "Backbone Cyclization: A New Method for Conferring Conformational Constraint on Peptides," *Biopolymers*, 31(6):745-750 (1991).

Gingeras et al., "Hybridization properties of immobilized nucleic acids," *Nuc. Acids Res.*, 15(13):5373-5390 (87).

Gummerlock et al., "RAS Enzyme-Linked Immunoblot Assay Discriminates p21 Species: A Technique to Dissect Gene Family Expression," *Anal. Biochem.*, 180:158-168 (1989).

Gurney et al., "Activation of a potassium current by rapid photochemically generated step increases of intracellular calcium in rat sympathetic neurons," *PNAS*, 84:3496-3500 (1987).

Haase et al., "Detection of Two Viral Genomes in Single Cells by Double-Label Hybridization in Situ and Color Microradioautography," *Science*, 227:189-192 (1985).

Hacia, et al., "Two color hybridization analysis using high density oligonucleotide arrays and energy transfer dyes," *Nuc. Acids Res.*, 26(16):3865-3866 (1998).

Hack, M.L., "Conics Formed to Make Fluid & Industrial Gas Micromachines," *Genetic Engineering News*, 15(18):1, 29 (1995).

Hagedorn et al., "Pumping of Water Solutions in Microfabricated Electrohydrodynamic Systems," from Micro Electro Mechanical Systems conference in Travemunde Germany (1992).

Hames et al., *Nuclear acid hybridization, a practical approach*, cover page and table of contents (1985).

Hanahan et al., "Plasmid Screening at High Colony Density," *Meth. Enzymology*, 100:333-342 (1983).

Hanahan et al., "Plasmid screening at high colony density," *Gene*, 10:63-67 (1980).

Haridasan et al., "Peptide Synthesis using Photolytically Cleavable 2-Nitrobenzyloxycarbonyl Protecting Group," *Proc. Indian Natn. Sci. Adad.*, 53A(6):717-728 (1987).

Harrison et al., "Capillary Electrophoresis and Sample Injection Systems Integrated on a Planar Glass Chip," *Anal. Chem.*, 64:1926-1932 (1992).

Harrison et al., "Micromachining a Minaturized Capillary Electrophoresis-Based Chemical Analysis System on a Chip," Science, 261:895-897 (1993).

Harrison et al., "Towards minaturized electrophoresis and chemical analysis systems on silicon: an alternative to chemical sensors*," *Sensors and Actuators*, B10:107-116 (1993).

Harrison et al., "Rapid separation of fluorescein derivatives using a micromachined capillary electrophoresis system," *Analytica Chemica Acta*, 283:361-366 (1993).

Hellberg et al., "Minimum analogue peptide sets (MAPS) for quantitative structure-activity relationships," *Int. J. Peptide Protein Res.*, 37:414-424 (1991).

Hilser et al., "Protein and peptide mobility in capillary zone electrophoresis, A comparison of existing models and further analysis," *J. Chromatography*, 630:329-336 (1993).

Ho et al., "Highly Stable Biosensor Using an Artificial Enzyme," *Anal.Chem.*, 59:536-537 (1987).

Hochgeschwender et al., "Preferential expression of a defined T-cell receptor β-chain gene in hapten-specific cytotoxic T-cell clones," *Nature*, 322:376-378 (1986).

Hodgson, J., "Asssays A La Photolithography," *Biotech.*, 9:419 (1991).

Hodgson et al., "Hybridization probe size control: optimized 'oligolabelling'," *Nuc.Acids Res.*, 15(15):6295 (1987).

Hopman et al., "Bi-color detection of two target DNAs by non-radioactive in situ hybridization*," *Histochem.*, 85:1-4 (1986).

Iwamura et al., "1-Pyrenylmethyl Esters, Photolabile Protecting Groups for Carboxlic Acids," *Tetrahedron Ltrs.*, 28(6):679-682 (1987).

Iwamura et al., "1-(α-Diazobenzyl)pyrene: A Reagent for Photolabile and Fluorescent Protection of Carboxyl Groups of Amino Acids and Peptides," *Synlett*, p. 35-36 (1991).

Jacobson et al., "Effects of Injection Schemes and Column Geometry on the Performance of Microchip Electrophoresis Devices," Anal. Chem., 66:1107-1113 (1994).

Jacobson et al., "Open Channel Electrochromatography on a Microchip," Anal. chem., 66:2369-2373 (1994).

Jacobson et al., "Microchip Capillary Electrophoresis with an Integrated Postcolumn Reactor" Anal. Chem., 66:3472-3476 (1994).

Jacobson et al., "Precolumn Reactions with Electrophoretic Analysis Integrated on a Microchip," *Anal. Chem.*, 66:4127-4132 (1994).

Jacobson et al., "Microfabricated chemical measurement systems," *Nature Medicine*, 1(10):1093-1096 (1995).

Jacobson et al., "Fused Quartz Substrates for Microchip Electrophoresis," *Anal. chem.*, 67:2059-2063 (1995).

Jacobson et al., "High-Speed Separtions on a Microchip," Anal. Chem., 66:1114-1118 (1994).

Jacobson et al., "Microchip electrophoresis with sample stacking," *Electrophoresis*, 16:481-486 (1995).

Jayakumari, "Peptide synthesis in a triphasic medium catalysed by papain immobilized on a crosslinked polystyrene support," *Indian J. Chemistry*, 29B:514-517 (1990).

Jovin et al., "Luminescence Digital Imaging Microscopy," *Ann. Rev. Biophys. Chem.*, 18:271-308 (1989).

Kafatos et al., "Determination of nucleic acid sequence homologies and relative concentrations by a dot hybridization procedure," *Nuc. Acids Res.*, 7(6):1541-1553 (1979).

Kaiser et al., "Peptide and Protein Synthesis by Segment Synthesis-Condensation," *Science*, 243:187-192 (1989).

Kaplan et al., "Photolabile cholators for the rapid photorelease of divalent cations," *PNAS*, 85:6571-6575 (1988).

Karube, "Micro-biosensors based on silicon fabrication technology," chapter 25 from Biosensors:Fundamentals and Applications, Turner et al., eds., Oxford Publ., 1987, pp. 471-480 (1987).

Kates et al., "A Novel, Convenient, Three-dimensional Orthogonal Strategy for Solid-Phase Synthesis of Cyclic Peptides 1-3," *Tetrahed. Letters*, 34(10):1549-1552 (1993).

Kerkof et al., "A Procedure for Making Simultaneous Determinations of the Relative Levels of Gene Transcripts in Tissues or Cells," *Anal. Biochem.*, 188:349-355 (1990).

Khrapko et al., "An Oligonucleotide hybridization approach to DNA sequencing," *FEBS Lett.*, 256(1,2):118-122 (1989).

Khrapko et al., "A method for DNA sequencing by hybridization with oligonucleotide matrix," *DNA Seq. Map.*, 1:375-388 (1991).

Kidd et al., "60 $_1$-Antitrypsin deficiency detection by direct analysis of the mutation in the gene," *Nature*, 304:230-234 (1983).

Kievits et al., "Rapid subchromosomal localization of cosmids by nonradioactive in situ hybridization," *Cytogenetics Cell Genetics*, 53(2-3):134-136 (1990).

Kimura et al., "An Immobilized Enzyme Membrane Fabrication Method using an Ink Jet Nozzle," *Biosensors*, 4:41-52 (1988).

Kimura et al., "An Integrated SOS/FET Multi-Biosensor," *Sensors & Actuators*, 9:373-387 (1986).

Kitazawa et al., "In situ DNA-RNA hybridization using in vivo bromodeoxyuridine-labeled DNA probe," *Histochemistry*, 92:195-199 (1989).

Kleinfeld et al., "Controlled Outgrowth of Dissociated Neurons on Patterned Substrates," *J. Neurosci.*, 8(11):4098-4120 (1988).

Knight, P., "Materials and Methods/Microsequencers for Proteins and Oligosaccharides," *Bio/Tech.*, 7:1075-76 (1989).

Kohara et al., "The Physical Map of the Whole *E. coli* Chromosome: Application of a New Strategy for Rapid Analysis and Sorting of a Large Genomic Library," *Cell*, 50:495-508 (1987).

Krile et al., "Multiplex holography with chirp-modulated binary phase-coded reference-beam masks," *Applied Opt.*, 18(1):52-56 (1979).

Labat, I., "Subfragments as an informative characteristic of the DNA molecule—computer simulation," research report submitted to the University of Belgrade College of Natural Sciences and Mathematics, (1988).

Lander et al., "Genomic Mapping by Fingerprinting Randon Clones: A Mathematical Analysis," *Genomics*, 2:231-239 (1988).

Lainer et al., "Human Lymphocyte Subpopulations Identified by Using Three-Color Immunofluorescence and Flow Cytometry Analysis: Correlation of Leu-2, Leu-3, Leu-7, Leu-8, and Leu-11 Clee Surface Antigen Expression," *Journal of Immunology*, 132(1):151-156 (1984).

Lam et al., "A new type of synthetic peptide library for identifying ligand-binding activity," *Nature*, 354:82-84 (1991).

Laskey et al., "Messenger RNA prevalence in sea urchin embryos measured with cloned cDNAs," *PNAS*, 77(9):5317-5321 (1980).

Lee et al., "synthesis of a Polymer Surface Containing Covalently Attached Triethoxysilane Functionality: Adhesion to Glass," *Macromolecules*, 21:3353-3356 (1988).

Lehrach et al., "Labelling oligonucleotides to high specific activity (I)," *Nuc. Acids Res.*, 17(12):4605-4610 (89).

Lehrach et al., "Phage Vectors—EMBL Series," *Meth. Enzymology*, 153:103-115 (1987).

Lehrach et al., "Hybridization Fingerprinting in Genome Mapping and Sequencing," *Genome Analysis vol. 1: Genetic and Physical Mapping*, Cold Spring Harbor Laboratory Press, pp. 39-81 (1990).

Levy, M.F., "Preparing Additive Printed Circuits," *IBM Tech. Discl. Bull.*, 9(11):1473 (1967).

Lewin, Benjamin, eds., *Genes*, third edition, John Wiley & Sons, cover page, preface and table of contents, (1987).

Lichter et al., "High-Resolution Mapping of Human Chromosome 11 by in Situ hybridization with Cosmid Clones," *Science*, 247:64-69 (1990).

Lichter et al., "Fluorescence in situ hybridization with *Alu* and L1 polymerase chain reaction probes for rapid characterization of human chromosomes in hybrid cell lines," *PNAS*, 87:6634-6638 (1990).

Lichter et al., "Rapid detection of human chromosome 21 aberrations by *in situ* hybridization," *PNAS*, 85:9664-9668 (1988).

Lichter et al., "Is non-isotopic *in situ* hybridization finally coming of age," *Nature*, 345:93-94 (1990).

Lieberman et al., "A Light source Smaller Than the Optical Wavelength," *Science*, 247:59-61 (1990).

Lipshutz et al., "Using Oligonucleotide Probe Arrays To Access Genetic Diversity," *BioTech.*, 19(3):442-7 (1995).

Little, P., "Clone maps made simple," *Nature*, 346:611-612 (1990).

Liu et al., "Sequential Injection Analysis in Capillary Format with an Electroosmotic Pump," *Talanta*, 41(11):1903-1910 (1994).

Lockhart et al., "Expression monitoring by hybridization to high-density oligonucleotide arrays," *Nat. Biotech.*, 14:1675-1680 (1996).

Logue et al., "General Approaches to Mask Design for Binary Optics," SPIE, 1052:19-24 (1989).

Loken et al., "three-color Immunofluorescence Analysis of Leu Antigens on Human Peripheral Blood Using Two Lasers on a Fluorescence-Activated Cell Sorter," *Cymoetry*, 5:151-158 (1984).

Love et al., "Screening of λ Library for Differentially Expressed Genes Using *in Vitro* Transcripts," *Anal. Biochem.*, 150:429-441 (1985).

Lowe, C.R., "Biosensors," *Trends in Biotech.*, 2:59-65 (1984).

Lowe, C.R., "An Introduction to the Concepts and Technology of Biosensors," *Biosensors*, 1:3-16 (1985).

Lowe, C. R., Biotechnology and Crop Improvement and Protection, BCPC Publications, pp. 131-138 (1986).

Lowe et al., "Solid-Phase Optoelectronic Biosensors," *Methods in Enzymology*, 137:338-347 (1988).

Lowe, C.R., "Biosensors," *Phil. Tran. R. Soc. Lond.*, 324:487-496 (1989).

Lu et al., "Differential screening of murine ascites cDNA libraries by means of in vitro transcripts of cell-cycle-phase-specific cDNA and digital image processing," *Gene*, 86:185-192 (1990).

Luo, J. et al., "Improving the fidelity of *Thermus thermophilus* DNA ligase," *Nuc. Acids Res.*, 24(14):3071-3078 (1996).

Lysov et al., "A new method for determining the DNA nucleotide sequence by hybridization with oligonucleotides," *Doklady Biochem.*, 303(1-6):436-438 (1989).

Lysov et al., "DNA Sequencing by Oligonucleotide Hybridization," First International Conference on Electrophoresis, Supercomputing and the Human Genome, Apr. 10-13, 1990 p. 157.

MacDonald et al., "A Rapid ELISA for Measuring Insulin in a Large Number of Research Samples," *Metabolism*, 38(5):450-452 (1989).

Mairanovsky, V.G., "Electro-Deprotection- Electrochemical Removal of Protecting Groups**," *Agnew. Chem. Int. Ed. Engl.*, 15(5):281-292 (1976).

Manz et al., "Miniaturized Total Chemical Analysis Systems: a Novel Concept for Chemical Sensing," *Sensors and Actuators*, B1:244-248 (1990).

Manz et al., "Micromachining of monocrystalline silicon and glass for chemical analysis systems, A look into next century's technology or just a fashionable craze?," *Trends in Analytical Chem.*, 10(5):144-149 (1991).

Manz et al., "Planar chips technology for minaturization and integration of separation techniques into monitoring systems, Capillary electrophoresis on a chip," *J. Chromatography*, 593:253-258 (1992).

Manz et al., "Planar Chips Technology for Miniaturization of Separation Systems: A Developing Perspective in Chemical Monitoring," chapter 1, 1-64 (1993).

Manz et al., "Electroosmotic pumping and electrophoretic separations for minaturized chemical analysis systems," *J. Micromech. Microeng.*, 4:257-265 (1994).

Masiakowski et al., "*Cloning of cDNA sequences of hormone-regulated genes from the MCF-7* human breast cancer cell line," *Nuc. Acids Res.*, 10(24):7895-7903 (1982).

Matsumoto et al., "Preliminary Investigation of Micropumping Based on Electrical Control of Interfacial Tension," IEEE, pp. 105-110 (1990).

Matsuzawa et al., "Containment and growth of neuroblastoma cells on chemically patterned substrates," *J. Neurosci. Meth.*, 50:253-260 (1993).

Matthes et al., "Simultaneous rapid chemical synthesis of over one hundred oligonucleotides on a microscale," *EMBO J.*, 3(4):801-805 (1984).

McCray et al., "Properties and Uses of Photoreactive Caged Compounds," *Ann. Rev. Biophys. Biophys. Chem.*, 18:239-270 (1989).

McGall et al., "The Efficiency of Light-Directed Synthesis of DNA Arrays on Glass Substrates," *J. American Chem. Soc.*, 119(22):5081-5090 (1997).

McGillis, VLSI Technology, Sze, eds., Chapter 7, "Lithography," pp. 267-301 (1983).

McMurray, J.S., "Solid Phase Synthesis of a Cyclic Peptide Using Fmoc Chemistry," *Tetrahedron Letters.*, 32(52):7679-7682 (1991).

Meinkoth et al., "Review: Hybridization of Nucleic Acids Immobilized on solid Supports," *Analytical Biochem.*, 138:267-284 (1984).

Melcher et al., "Traveling-Wave Bulk Electroconvection Induced across a Temperature Gradient," *Physics of Fluids*, 10(6):1178-1185 (1967).

Merrifield, R.B., "Solid Phase peptide Synthesis. I. The Synthesis of a Tetrapeptide," *J. Am.Chem.Soc.*, 85:2149-2154 (1963).

Michiels et al., "Molecular approaches to genome analysis: a strategy for the construction of ordered overlapping clone libraries," *CABIOS*, 3(3):203-10 (1987).

Mirzabekov, A.D., "DNA sequencing by hybridization—a megasequencing method and a diagnostic tool?," *TIBTECH*, 12:27-32 (1994).

Miyada et al., "Oligonucleotide Hybridization Techniques," *Meth. Enzymology*, 154:94-107 (1987).

Monaco et al., "Human Genome Linking with Cosmids and Yeast Artificial Chromosomes", abstract from CSHS, p. 50, (1989).

Morita et al., "Direct pattern fabrication on silicone resin by vapor phase electron beam polymerization," *J. Vac.Sci. Technol.*, B1(4):1171-1173 (1983).

Morrison et al., "Solution-Phase Detection of Polynucleotides Using Interacting Fluorescent Labels and Competitive Hybridization," *Anal. Biochem.*, 183:231-244 (1989).

Munegumi et al., "thermal Synthesis of Polypeptides from N-Boc-Amino Acid (Aspartic Acid, β-Aminoglutaric Acid) Anhydrides," *Chem. Letters*, pp. 1643-1646 (1988).

Mutter et al., "Impact of Conformation on the Synthetic Strategies for Peptide Sequences," pp. 217-228 from Chemistry of Peptides and Proteins, vol. 1, Proceedings of the Third USSR-FRG Symp., in USSR (1982).

Nakamori et al., " A Simple and Useful Method for Simultaneous Screening of Elevated Levels of Expression of a Variety of Oncogenes in Malignant Cells," *Jpn. J. Cancer Res.*, 79:1311-1317 (1988).

Nederlof et al., "Multiple Fluorescence In Situ Hybridization," *Cytometry*, 11:126-131 (1990).

Nederlof et al., "Three-Color Fluorescence In Situ Hybridization for the Simultaneous Detection of Multiple Nucleic Acid Sequences," *Cytometry*, 10:20-27 (1989).

Nizetic et al., "An improved bacterial colony lysis procedure enables direct DNA hybridisation using short (10, 11 bases) oligonucleotides to cosmids," *Nuc. Acids Res.*, 19(1):182 (1990).

Nizetic et al., "Construction, arraying, and high-density screening of large insert libraries of human chromosomes X and 21: their potential use as reference libraries," *PNAS*, 88:3233-3237 (1991).

Nyborg, W., "Acoustic Streaming," chapter 11 pp. 265-329 from Physical Acoustics, Principles and Methods, Mason, eds., vol. II, part B, Academic Press, New York and London (1965).

Ocvirk et al., "High Performance Liquid Chromatography Partially Integrated onto a Silicon Chip," *Analyt. Meth. Instrumentation*, 2(2):74-82 (1995).

Ohtsuka et al., "Studies on transfer ribonucleic acids and related compounds. IX Ribonucleic oligonucleotide synthesis using a photosensitive 0-nitrobenzyl protection at the 2'-hydroxl group," *Nuc.Acids.Res.*, 1(10):1351-1357 (1974).

Olefirowicz et al., "Capillary Electrophoresis for Sampling Single Nerve Cells," *Chimia*, 45(4):106-108 (1991).

Olson et al., "Random-clone strategy for genomic restriction mapping in yeast," *PNAS*, 83:7826-7830 (1986).

Patchornik et al., "Photosensitive Protecting Groups," *J.Am. Chem.Soc.*, 92(21):6333-6335 (1970).

Patent Abstracts of Japan from EPO, Abst. 13:557, JP 1-233 447 (1989).

Pease et al., "Light-generated oligonucleotide arrays for rapid DNA sequence analysis," *PNAS*, 91:5022-26 (1994).

Pevzner, P.A., "DNA Physical Mapping and Alternating Eulerian Cycles in Colored Grapes," *Algorithmica*, 13(1-2):77-105 (1995).

Pevzner et al., "Multiple Filtration and Approximate Pattern Matching," *Algorithmica*, 13(1-2):135-154 (1995).

Pevzner et al., "Generalized Sequence Alignment and Duality," *Adv. Applied Math.*, 14:139-171 (1993).

Pevzner, P.A., "1-Tuple DNA Sequencing: Computer Analysis," *J. Biomol. Struct. Dynam.*, 7(1):63-69 (1989).

Pfahler et al., "Liquid Transport in Micron and Submicron Channels," *Sensors and Actuators*, A21-A23:431-4 (90).

Pfeifer et al., "Genomic Sequencing and Methylation Analysis by Ligation Mediated PCR," *Science*, 246:810-813 (1989).

Pidgeon et al., "Immobilized Artificial Membrane Chromatography: Supports Composed of Membrane Lipids," *Anal. Biochem.*, 176:36-47 (89).

Pillai, V.N., "Photoremovable Protecting Groups in Organic Synthesis," *Synthesis*, pp. 1-26 (1980).

Pillai et al., "3-Nitro-4-Aminomethylbenzoylderivative von Polythylenglykolen: Eine neue Klasse von Photosensitiven loslichen Polymeren Tragern zur Synthese von C-terminalen Peptidamiden," *Tetrah. Itr.*, # 36 p. 3409-3412 (1979).

Pillai et al., "Synthetic Hydrophilic Polymers, Biomedical and Chemical Applications," *Naturwissenschaften*, 68:558-566 (1981).

Pirrung et al., "Proofing of Photolithographic DNA Synthesis with 3'.5'-Dimethoxybenzoinyloxycarbonyl-Protected Deoxynucleoside Phosphoramidites," *J. Org. Chem.*, 63(2):241-246 (1998).

Pirrung et al., "Comparison of Methods for Photochemical Phosphoramidite-Based DNA Synthesis," *J. Org. Chem.*, 60:6270-6276 (1995).

Ploax et al., "Cyclization of peptides on a solid support," *Int. J. Peptide Protein Research*, 29:162-169 (1987).

Polsky-Cynkin et al., "Use of DNA Immobilized on Plastic and Agarose Supports to Detect DNA by Sandwich Hybridization," *Clin. Chem.*, 31(9):1428-1443 (1985).

Poustka et al., "Molecular Approaches to Mammallian Genetics," Cold Spring Harbor Symposia on Quantitive Biology, 51:131-139 (1986).

Purushothaman et al., "Synthesis of 4,5-diarylimidazoline-2-thiones and their photoconversion to bis(4,5-diarylimidazol-2-yl) sulphides," *Ind. J. Chem.*, 29B:18-21 (1990).

Quesada et al., "High-Sensitivity DNA Detection with a Laser-Exited Confocal Fluorescence Gel Scanner," *Biotechniques*, 10:616 (1991).

Reichmanis et al., *J. Polymer Sci. Polymer Chem. Edition*, 23:1-8 (1985).

Renz et al., "A colorimetric method for DNA hybridization," *Nuc. Acids Res.*, 12(8):3435-3445 (1984).

Richter et al., "An Electrohydrodynamic Micropump," *IEEE*, pp. 99-104 (1990).

Richter et al., "Electrohydrodynamic Pumping and Flow Measurement," *IEEE*, pp. 271-276 (1991).

Richter et al., "A Micromachined electrohydrodynamic (EHD) pump," *Sensors and Actuators*, A29:159-168 (91).

Robertson et al., "A General and Efficient Route for Chemical Aminoacylation of Transfer RNAs," *J. Am. Chem. Soc.*, 113:2722-2729 (1991).

Rodda et al., "The Antibody Response to Myoglobin-I. Systematic Synthesis of Myglobin Peptides Reveals Location and Substructure of Species-Dependent Continuous Antigenic Determinants," *Mol. Immunol.*, 23(6):603-610 (1986).

Rodgers, R.P., "Data Processing of Immunoassay Results," Manual of Clin. Lab. Immunol., 3rd ed., ch. 15, pp. 82-87 (1986).

Rose, D.J., "Free-solution reactor for post-column fluorescence detection in capillary zone electrophoresis," *J. Chromatography*, 540:343-353 (1991).

Rovero et al., "Syntheis of Cylic Peptides on solid Support," *Tetrahed. Letters*, 32(23):2639-2642 (1991).

Sambrook, Molecular Cloning—A Laboratory Manual, publ. in 1989 (not included).

Saiki et al., "Genetic analysis of amplified DNA with immobilized sequence-specific oligonucleotide probes," *PNAS*, 86:6230-6234 (1989).

Saiki et al., "Analysis of enzymatically amplified β-globin and HLA-DQα DNA with Allele-specific oligonucleotide probes," *Nature*, 324:163-166 (1986).

Schafer et al., "DNA fingerprinting using non-radioactive oligonucleotide probes specific for simple repeats," *Nuc. Acids. Res.*, 16(19):9344 (1988).

Scharf et al., "HLA class II allclic variation and susceptibility to pemphigus vulgaris," *PNAS*, 85(10):3504-3508 (1988).

Schena et al., "Parallel human genome analysis: Microarray-based expression monitoring of 1000 genes," *PNAS*, 93:10614-10619 (1996).

Schuup et al., "Mechanistic Studies of the Photorearrangement of o-Nitrobenzyl Esters," *J. Photochem.*, 36:85-97 (1987).

Seed, B., "Diazotizable arylamine cellulose papers for the coupling and hybridization of nucleic acids," *Nuc. Acids Res.*, 10(5):1799-1810 (1982).

Seiler et al., "Planar Glass Chips for Capillary Electrophoresis: Repetitive Sample Injection, Quantitation, and Separation Efficency," *Anal. Chem.*, 65:1481-1488 (1993).

Seller et al., "Electroosmotic Pumping and Valveless Control of Fluid Flow within a Manifold of Capillaries on a Glass Chip," Anal. Chem., 66:3485-3491 (1994).

Semmelhack et al., "Selective Removal of Protecting Groups Using Controlled Potential Electrolysis," *J. Am. Chem. Society*, 94(14):5139-5140 (1972).

Sheldon et al., "Matrix DNA Hybridization," *Clinical Chemistry*, 39(4):718-719 (1993).

Shin et al., "Dehydrooligonpeptides. XI. Facile Synthesis of Various Kinds of Dehydrodi-and tripeptides, and Dehydroenkephalins Containing Tyr Residue by Using N-Carboxydehydrotyrosine Anhydride," *Bull. Chem. Soc. Jpn.*, 62:1127-1135 (1989).

Sim et al., "Use of a cDNA Library for Studies on Evolution and Developmental Expression of the Chorion Multigene Families," *Cell*, 18:1303-1316 (1979).

Smith et al., "A Novel Method for Delineating Antigenic Determinants: Peptide Synthesis and Radioimmunoassay Using the Same Solid Support," *Immunochemistry*, 14:565-568 (1977).

Sofia, M.J., "Carbohydrate-based combinatorial libraries," *Molecular Diversity*, 3:75-94 (1998).

Southern et al., "Report on the Sequencing by Hybridization Workshop," *Genomics*, 13:1378-1383 (1992).

Southern et al., "Oligonucleotide hybridisations on glass supports: a novel linker for oligonucleotide synthesis and hybridization properties of oligonucleotides synthesized in situ," *Nuc. Acids Res.*, 20(7):1679-1684 (1992).

Southern et al., "Analyzing and Comparing Nucleic Acid Sequences by Hybridization to Arrays of Oligonucleotides: Evaluation Using Experimental Models," Genomics, 13:1008-10017 (1992).

Southern, E.M., "Detection of Specific Sequences Among DNA Fragments Separated by Gel Electrophoresis," *J. Mol. Biol.*, 98:503-517 (1975).

Stemme et al., "A valveless diffuser/nozzle-based fluid pump," *Sensors and Actuators*, A39:159-167 (1993).

Stryer, L., "DNA Probes and Genes Can be Synthesized by Automated Solid-Phase Methods," from *Biochemistry*, Third Edition, published by W.H. Freeman & Co., (1988).

Stuber et al., "Synthesis and photolytic cleavage of bovine insulin B22-30 on a nitrobenzoylgylcyl-poly (ethylene glycol) support," *Int. J. Peptide Protein Res.*, 22(3):277-283 (1984).

Sundberg et al., "Spatially-Addressable Immobilization of Macromolecules on Solid Supports," *J. Am. Chem. Soc.*, 117(49):12050-12057 (1995).

Swedberg, S.A., "Use of non-ionic and zwitterionic surfactants to enhance selectivity in high-performance capillary electrophoresis, An apparent micellar electrokinetic capillary chromatography mechanism," *J. Chromatography*, 503:449-452 (1990).

Thomas, P.S., "Hybridization of denatured RNA and small DNA fragments transferred to nitrocellulose," *PNAS*, 77(9):5201-5205 (1980).

Titus et al., "Texas Red, a Hydrophilic, red-emitting fluorophore for use with fluorescein in dual parameter plow microfluorometric and fluorescence microscopic studies," *J. Immunol. Meth.*, 50:193-204 (1982).

Tkachuk et al., "Detection of bcr-abl Fusion in chronic Myelogeneous Leukemia by in situ Hybridization," *Science*, 250:559-562 (90).

Trzeciak et al., "Synthesis of 'Head-to-Tail' Cyclized Peptides on Solid Support by FMOC Chemistry," *Tetrahed, Letters*, 33(32):4557-4560 (1992).

Tsien et al., "Control of Cytoplasmic Calcium with Photolabile Tetracarboxylate 2-Nitrobenzhydrol Chelators," *Biophys. J.*, 50:843-853 (1986).

Tsutsumi et al., "Expression of L- and M- Type Pyruvate Kinase in Human Tissues," *Genomics*, 2:86-89 (1988).

Turchinskii et al., "Multiple Hybridization in Genome Analysis, Reaction of Diamines and Bisulfate with Cytosine for Introduction of Nonradioactive labels Into DNA," *Molecular Biology*, 22:1229-1235 (1988).

Turner et al., "Photochemical Activation of Acylated α-Thrombin," *J. Am. Chem. Soc.*, 109:1274-1275 (1987).

Urdea et al., "A novel method for the rapid detection of specific nucleotide sequences in crude biological samples without blotting or radioactivity; application to the analysis of hepatitis B virus in human serum," *Gene*, 61:253-264 (1987).

Urdea et al., "A comparison of non-radioisotopic hybridization assay methods using fluorescent, chemiluminescent and enzyme labeled synthetic oligodeoxyribonucleotide probes," *Nuc. Acids Res.*, 16(11):4937-4956 (1988).

Van der Voort et al., "Design and Use of a Computer Controlled Confocal Microscope for Biological Applications," *Scanning*, 7(2):66-78 (1985).

Van Hijfte et al., "Intramolecular 1,3-Diyl Trapping Reactions. A Formal Total Synthesis of -Coriolin," J. Organic Chemistry, 50:3942-3944 (1985).

Veldkamp, W.B., "Binary optics: the optics technology of the 1990s," CLEO 90, vol. 7, paper # CMG6 (1990).

Verlaan-de Vries et al., "A dot-blot screening procedure for mutated ras oncongenes using synthetic oligodeoxynucleotides," Gene, 50:313-320 (1986).

Verpoorte et al., "Three-dimensional micro flow manifolds for miniaturized chemical analysis systems," J. Micromech. Microeng., 4:246-256 (1994).

Volkmuth et al., "DNA electrophoresis in microlithographic arrays," Nature, 358:600-602 (1992).

Voss et al., "The immobilization of oligonucleotides and their hybridization properties," Biochem. Soc. Transact., 16:216-217 (1988).

Wada, A., International Workshop on Automatic and High Speed DNA Base Sequencing, Hayashibara Forum 1987 at Hayashibara Biochemical Laboratories, Okayama, Japan, Jul. 7-9, 1987.

Walker et al., "Photolabile Protecting Groups for an Acetylcholine Receptor Ligand. Synthesis and Photochemistry of a New Class of o-Nitrobenzyl Derivatives and their Effects on Receptor Function," Biochemistry, 25:1799-1805 (1986).

Wallace et al., "The use of synthetic oligonucleotides as hybridization probes. II. Hybridization of oligonucleotides of mixed sequence to rabbit β-globin DNA," Nuc. Acids Res., 9(4):879 (1981).

Wallace et al., "Hybridization of synthetic oligodeoxyribonucleotides to $\Phi_\chi$ 174 DNA: the effect of single base pair mismatch," Nuc. Acids Res., 11(6):3543-3557 (1979).

Washizu et al., "Handling Biological Cells Using a Fluid Integrated Circuit," IEEE Transactions Industry Applications, 26(2):352-358 (1990).

Wiedmann, M. et al., "Ligase Chain Reaction (LCR)—Overview and Applications," PCR Meth. Appl., 3(4):S51-S64 (1994).

Werner et al., "Size-Dependent Separation of Proteins Denatured in SDS by Capillary Electrophoresis Using a Replaceable Sieving Matrix," Anal. Biochem., 212:253-258 (1993).

White et al., "An Evaluation of Confocal Versus Conventional Imaging of Biological Structures by Fluorescence Light Microscopy," J. Cell Biol., 105(1):41-48 (1987).

Widacki et al., "Biochemical Differences in Qa-2 Antigens Expressed by Qa-2+,6+ and Qa-2a+,6- Strains. Evidence for Differential Expression of the Q7 and Q9 Genes," Mol. Immunology, 27(6):559-570 (1990).

Wilcox et al., "Synthesis of Photolabile 'Precursors' of Amino Acid Neurotransmitters," J. Org. Chem., 55:1585-1589 (1990).

Wilding et al., "PCR in a Silicon Microstructure," Clin. Chem., 40(9):1815-1818 (1994).

Wilding et al., "Manipulation and Flow of Biological Fluids in Straight Channels Micromachined in Silicon," Clin. Chem., 40(1):43-47 (1994).

Wittman-Liebold, eds., Methods in Protein Sequence Analysis, from Proceedings of 7th Int'l Conf., Berlin, Germany, Jul. 3-8, 1988, table of contents, pp. xi-xx* (1989).

Wood et al., "Base composition-independent hybridization in tetramethylammonium chloride: A method for oligonucleotide screening of highly complex gene libraries," PNAS, 82:1585-1588 (1985).

Woolley et al., "Ultra-high-speed DNA fragment separations using microfabricated capillary array electrophoresis chips," PNAS, 91:11348-11352 (1994).

Wu et al., "Synthesis and Properties of Adenosine-5'-triphosphoro-γ-5-(5-sulfonic acid)naphthyl Ethylamidate: A Fluorescent Nucleotide Substrate for DNA-Dependent RNA Polymerase from Escherichia coli," Arch. Biochem. Biophys., 246(2):564-571 (1986).

Wu et al., "Laboratory Methods, Direct Analysis of Single Nucleotide Variation in Human DNA and RNA Using In Situ Dot Hybridization," DNA, 8(2):135-142 (1989).

Yamamoto et al., "Features and applications of the laser scanning microscope," J. Mod. Optics, 37(11):1691-1701 (1990).

Yarbrough et al., "Synthesis and Properties of Fluorescent Nucleotide Substrates for DNA-dependent RNA Polymerases," J. Biol. Chem., 254(23):12069-12073 (1979).

Yosomiya et al., "Performance, Glass fiber Having Isocyanate Group on the Surface. Preparation and Reaction with Amino Acid," Polymer Bulletin, 12:41-48 (1984).

Young, W.S., "Simultaneous Use of Digoxigenin- and Radiolabeled Oligodeoxyribonucleotide Probes for Hybridization Histochemistry," Neuropeptides, 13:271-275 (1989).

Yue et al., "Miniature Field-Flow Fractionation System for Analysis of Blood Cells," Clin. Chem., 40(9):1810-1814 (1994).

Zehavi et al., "Light-Sensitive Glycosides. I. 6-Nitroveratryl β-D-Glucopyranoside and 2-Nitrobenzyl β-D-Glucopyranoside," J. Org. Chem., 37(14):2281-2285 (1972).

Zengerle et al., "Transient measurements on miniaturized diaphragm pumps in micorfluid systems," Sensors and Actuators, A46-47:557-561 (1995).

Zischler et al., "Non-radioactive oligonucleotide fingerprinting in the gel," Nuc. Acids Res., 17(11)4411 (1989).

Zischler et al., "Digoxigenated oligonucleotide probes specific for simple repeats in DAN fingerprinting and hybridization in situ," Hum. Genet., 82:227-233 (1989).

Southern, E.M., et al., Analyzing and Comparing Nucleic Acid Sequences by Hybridization to Arrays of Oligonucleotides: Evaluation Using Experimental Models, Genomics, 13: 1008-1017 (1992).

Maskos,U., and Southern, E.M., Parallel Analysis of Oligodeoxyribonucelotide (oligonucleotide) Interactions. I. Analysis of Factors Influencing Oligonucleotide Duplex Formation, Nucleic Acids Research, 20(7): 1675-1678 (1992).

Chrisey, L.A., et al., Selective Attachment of Synthetic DNA to Self-Assembled-Monolayer Functionalized Surfaces, Mat. Res. Soc. Symp. Proc., 330: 179-184 (Symposium held Nov. 29-Dec. 3, 1994).

Southern, E.M., et al., Arrays of Complementary Oligonucleotides for Analysing the Hybridisation Behaviour of Nucleic Acids, Nucleic Acids Research, 22(8): 1368-1373 (1994).

Lamture, J.B., et al., Direct Detection of Nucleic Acid Hybridization on the Surface of a Charge Coupled Device, Nucleic Acids Research, 22(11): 2121-2125 (1994).

Guo, Z., et al., Direct Fluorescence Analysis of Genetic Polymorphisms by Hybridization with Oligonucleotide Arrays on Glass Supports, Nucleic Acids Research, 22(24): 5456-5465 (1994).

Eggers, M., et al., A Microchip for Quantitative Detection of Molecules Utilizing Luminescent and Radioisotope Reporter Groups, BioTechniques, 17(3): 516-524 (1994).

Wetmer, J.G., "Light-Directed, Spatially Addressable Parallel Chemical Synthesis," *Chemtracts-Biochem Mol. Biol.*, 2: 207-210 (1991).

Chow, T., et al., A High Capacity, Reusable Oligodeoxythimidine Affinity Column, *Analytical Biochemistry*, 175: 63-66 (1988).

Dunn, A.R., and Sambrook, J., Mapping Viral mRNAs by Sandwich Hybridization, *Methods in Enzymology*, 65: 468-478 (1980).

Weetall, H.H., Covalent Coupling Methods for Inorganic Support Materials, *Methods in Enzymology*, 44: 134-148 (1976).

Rentrop, M., et al., Aminoakylsilane-treated Glass Slides as Support for *in situ* Hybridization of Keratin cDNAs to Frozen Tissue Sections Under Varying Fixation and Pretreatment Conditions, *Histochemical Journal*, 18: 271-276 (1986).

Matteucci, M.D., and Caruthers, M.H., Synthesis of Deoxyoligonucleotides on a Polymer Support, *J. Am. Chem. Soc.*, 103: 3185-3191 (1981).

Kessler, "Nonradioactive Labeling Methods for Nucleic Acids," *Nonisotopic DNA Probe Techniques*, edited by Larry Kricka, Chapter 2, pp. 29-92 (1991).

Dyson, N.J., "Immobilization of Nucleic Acids and Hybridization Analysis," *Essential Molecular Biology* vol. II: A Practical Approach, edited by T.A. Brown, Chapter 5, pp. 111-156 (1991).

Ballard, S.G., "Imaging Genes, Chromosomes and Nuclear Structures using Laser-Scanning Confocal Microscopy," *SPIE*, 1205:2-10 (1990).

Burns, D.H., "Scanning Slit Aperture Confocal Microscopy for Three-Dimensional Imaging," *Scanning*, 12: 156-160 (1990).

Frank, et al., "A multiple reaction system for automated simultaneous peptide synthesis," *Peptides*, 206-207 (1990).

Frank, et al., "Facile and Rapid Spot-Synthesis' of Large Numbers of Peptides on Membrane Sheets," *Peptides*, 151-152 (1990).

Haridasan & Rajasekharan Pillai, "Peptide Synthesis Using Photolytically Cleavable 2-Nitrobenzyloxycarbonyl Protecting Group," Proceedings of the Indian National Science Academy. Part A. Physical Science, 53(6) : 717-728 (1987).

Iwamura, Michiko et al., "1-pyrenyl esters, photolabile protecting groups for carboxylic acids," *Tetrahedron Letters*, 28 (6) : 679-682 (1987).

Rajasekharan Pillai, V.N., "Photoremovable Protecting Group in Organic Synthesis," *Synthesis*, 1(1): 1-26 (1980).

Southern, et al., "Parallel synthesis and analysis of large numbers of related chemical compounds: applications to oligonucleotides," *Journal of Biotechnology*, 35 : 217-227 (1994).

Voet, D. and Voet, J. G. "Biochemistry, Second Edition." John Wiley & Sons: New York, .57, 848-849 (1995).

* cited by examiner

*Primary Examiner*—Jezia Riley
(74) *Attorney, Agent, or Firm*—Thomas E. Malone, Esq.; Lisa M. Treannie, Esq.; Jesse A. Fecker

(57) ABSTRACT

A synthetic strategy for the creation of large scale chemical diversity. Solid-phase chemistry, photolabile protecting groups, and photolithography are used to achieve light-directed spatially-addressable parallel chemical synthesis. Binary masking techniques are utilized in one embodiment. A reactor system, photoremovable protective groups, and improved data collection and handling techniques are also disclosed. A technique for screening linker molecules is also provided.

17 Claims, 17 Drawing Sheets

Fig. 10

NUCLEOTIDES AND ANALOGS HAVING PHOTOREMOVABLE PROTECTING GROUPS

CROSS REFERENCE TO RELATED APPLICATIONS

The instant application is a Continuation of application Ser. No. 09/465,126, filed Dec. 17, 1999, which is a Continuation of application Ser. No. 09/063,933, filed Apr. 21, 1998, and a Continuation of application Ser. No. 08/466,632, filed June 6, 1995 now U.S. Pat. No. 5,744,305, which is a Rule 60 Divisional of application Ser. No. 08/390,272, filed Feb. 16, 1995 now U.S. Pat. No. 5,489,678, which is a file wrapper continuation of application Ser. No. 07/624,120, filed Dec. 6, 1990, now abandoned, which is a Continuation-in-Part of application Ser. No. 07/492,462, filed Mar. 7, 1990 now U.S. Pat. No. 5,143,854, which is a Continuation-in-Part of application Ser. No. 07/362,901, filed Jun. 7, 1989, now abandoned and a Continuation-in-Part of application Ser. No. 08/456,887, filed June 1, 1995, which is a Divisional of application Ser. No. 07/954,646, filed Sep. 30, 1992 now U.S. Pat. No. 5,445,934, which is a Divisional of application Ser. No. 07/850,356, filed Mar. 12, 1992 now U.S. Pat. No. 5,405,783, which is a Divisional of application Ser. No. 07/492,462, filed Mar. 7, 1990 now U.S. Pat. No. 5,143,854. The teachings of all of the above are incorporated herein by reference in their entirety.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The present invention relates to the field of polymer synthesis. More specifically, the invention provides a reactor system, a masking strategy, photoremovable protective groups, data collection and processing techniques, and applications for light directed synthesis of diverse polymer sequences on substrates.

SUMMARY OF THE INVENTION

Methods, apparatus, and compositions for synthesis and use of techniques for diverse polymer sequences on a substrate are disclosed, as well as applications thereof.

According to one aspect of the invention, an improved reactor system for synthesis of diverse polymer sequences on a substrate is provided. According to this embodiment the invention provides for a reactor for contacting reaction fluids to a substrate; a system for delivering selected reaction fluids to the reactor; a translation stage for moving a mask or substrate from at least a first relative location relative to a second relative location; a light for illuminating the substrate through a mask at selected times; and an appropriately programmed digital computer for selectively directing a flow of fluids from the reactor system, selectively activating the translation stage, and selectively illuminating the substrate so as to form a plurality of diverse polymer sequences on the substrate at predetermined locations.

The invention also provides a technique for selection of linker molecules in VLSIPS. According to this aspect of the invention, the invention provides a method of screening a plurality of linker polymers for use in binding affinity studies. The invention includes the steps of forming a plurality of linker polymers on a substrate in selected regions, the linker polymers formed by the steps of recursively: on a surface of a substrate, irradiating a portion of the selected regions to remove a protective group, and contacting the surface with a monomer; contacting the plurality of linker polymers with a ligand; and contacting the ligand with a labeled receptor.

According to another aspect of the invention, improved photoremovable protective groups are provided. According to this aspect of the invention a compound having the formula:

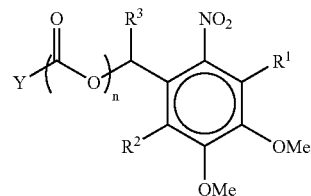

wherein n=0 or 1; Y is selected from the group consisting of an oxygen of the carboxyl of a natural or unnatural amino acid, an amino group of a natural or unnatural amino acid, or the C-5' oxygen group of a natural or unnatural deoxyribonucleic or ribonucleic acid; $R^1$ and $R^2$ independently are a hydrogen atom, a lower alkyl, aryl, benzyl, halogen, hydroxyl, alkoxyl, thiol, thioether, amino, nitro, carboxyl, formate, formamido, sulfido, or phosphido group; and $R^3$ is a alkoxy, alkyl, aryl, hydrogen, or alkenyl group is provided.

The invention also provides improved masking techniques for VLSIPS. According to one aspect of the masking technique, the invention provides an ordered method for forming a plurality of polymer sequences by sequential addition of reagents comprising the step of serially protecting and deprotecting portions of the plurality of polymer sequences for addition of other portions of the polymer sequences using a binary synthesis strategy.

Improved data collection equipment and techniques are also provided. According to one embodiment, the instrumentation provides a system for determining affinity of a receptor to a ligand comprising: means for applying light to a surface of a substrate, the substrate comprising a plurality of ligands at predetermined locations, the means for applying directing light providing simultaneous illumination at a plurality of the predetermined locations; and an array of detectors for detecting light fluoresced at the plurality of predetermined locations. The invention further provides for improved data analysis techniques including the steps of exposing fluorescently labelled receptors to a substrate, the substrate comprising a plurality of ligands in regions at known locations; at a plurality of data collection points within each of the regions, determining an amount of light fluoresced from the data collection points; removing the data collection points deviating from a predetermined statistical distribution and determining a relative binding affinity of the receptor to remaining data collection points.

Protected amino acid N-carboxy anhydrides for use in polymer synthesis are also disclosed. According to this aspect of the invention provides a compound having the formula:

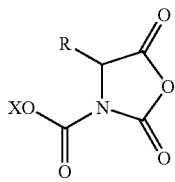

where R is a side chain of a natural or unnatural amino acid and X is a photoremovable protecting group.

A further understanding of the nature and advantages of the inventions herein may be realized by reference to the remaining portions of the specification and the attached drawings.

BRIEF DESCRIPTION OF THE DRAWINGS

FIG. 10 is a coordinate map for the ten-step binary synthesis;

DESCRIPTION OF THE PREFERRED EMBODIMENTS

Contents

Figure 1:
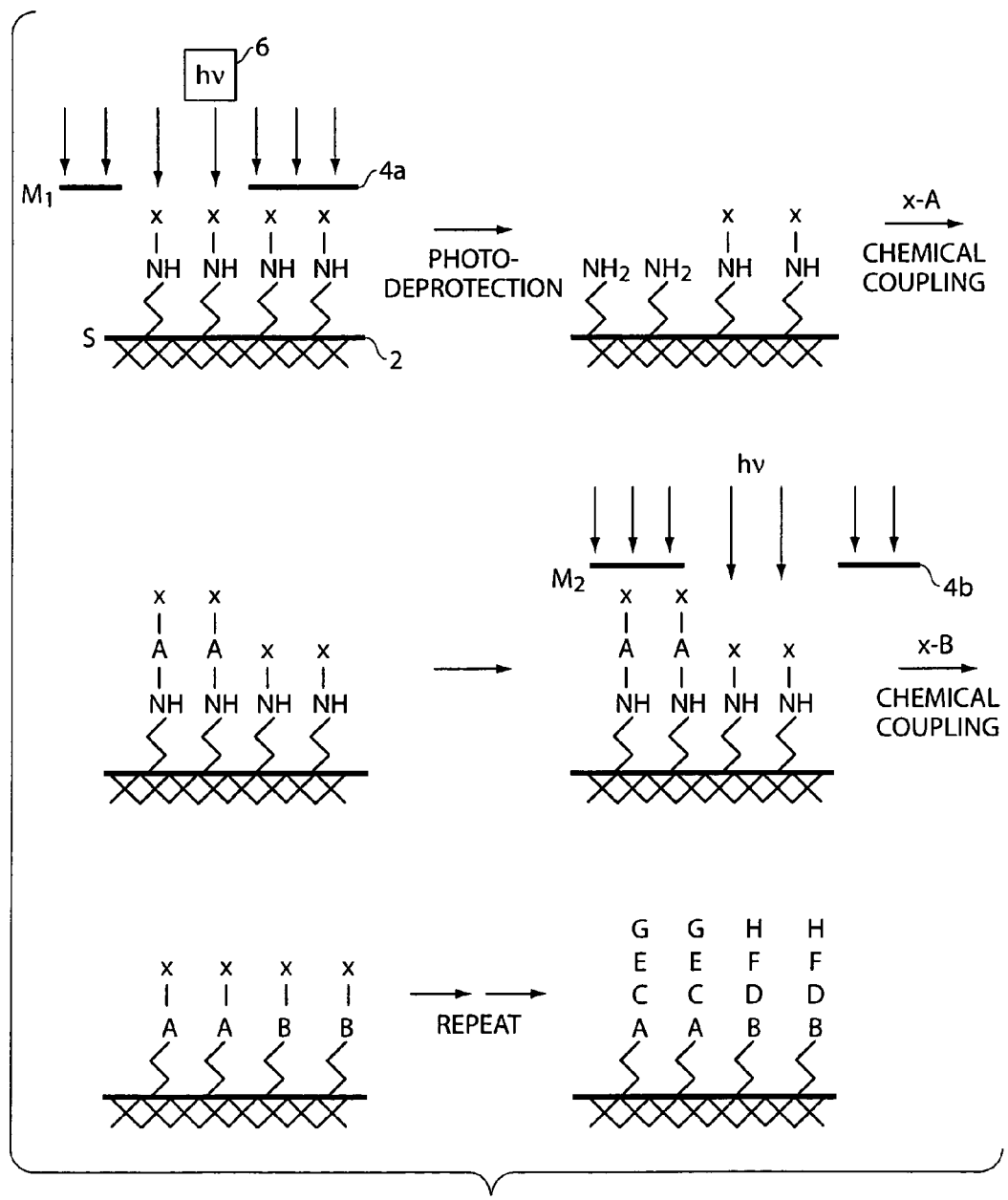
FIG. 1 schematically illustrates light-directed spatially-addressable parallel chemical synthesis.

I. Definitions
II. General
  A. Deprotection and Addition
    1. Example
    2. Example
  B. Antibody recognition
    1. Example
III. Synthesis
  A. Reactor System
  B. Binary Synthesis Strategy
    1. Example
    2. Example
    3. Example
    4. Example
    5. Example
    6. Example
  C. Linker Selection
  D. Protecting Groups
    1. Use of Photoremovable Groups During Solid-Phase Synthesis of Peptides
    2. Use of Photoremovable Groups Durign Solid-Phase Synthesis of Oligonucleotides
  E. Amino Acid N-Carboxy Anhydrides Protected with a Photoremovable Group
IV. Data Collection
  A. Data Collection System
  B. Data Analysis
V. Other Representative Applications
  A. Oligonucleotide Synthesis
    1. Example
VI. Conclusion I. Definitions Certain terms used herein are intended to have the following general definitions:

1. Complementary: Refers to the topological compatibility or matching together of interacting surfaces of a ligand molecule and its receptor. Thus, the receptor and its ligand can be described as complementary, and furthermore, the contact surface characteristics are complementary to each other.

2. Epitope: The portion of an antigen molecule which is delineated by the area of interaction with the subclass of receptors known as antibodies.

3. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides, nucleic acids, oligosaccharides, proteins, and monoclonal antibodies.

4. Monomer: A member of the set of small molecules which can be joined together to form a polymer. The set of monomers includes but is not restricted to, for example, the set of common L-amino acids, the set of D-amino acids, the set of synthetic amino acids, the set of nucleotides and the set of pentoses and hexoses. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis.

5. Peptide: A polymer in which the monomers are alpha amino acids and which are joined together through amide bonds and alternatively referred to as a polypeptide. In the context of this specification it should be appreciated that the amino acids may be the L-optical isomer or the D-optical isomer. Peptides are often two or more amino acid monomers long, and often more than 20 amino acid monomers long. Standard abbreviations for amino acids are used (e.g., P for proline). These abbreviations are included in Stryer, *Biochemistry*, Third Ed., 1988, which is incorporated herein by reference for all purposes.
6. Radiation: Energy which may be selectively applied including energy having a wavelength of between $10^{-14}$ and $10^4$ meters including, for example, electron beam radiation, gamma radiation, x-ray radiation, ultra-violet radiation, visible light, infrared radiation, microwave radiation, and radio waves. "Irradiation" refers to the application of radiation to a surface.
7. Receptor: A molecule that has an affinity for a given ligand. Receptors may be naturally-occurring or man-made molecules. Also, they can be employed in their unaltered state or as aggregates with other species. Receptors may be attached, covalently or noncovalently, to a binding member, either directly via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex.
Other examples of receptors which can be investigated by this invention include but are not restricted to:
 a) Microorganism receptors: Determination of ligands which bind to receptors, such as specific transport proteins or enzymes essential to survival of microorganisms, is useful in a new class of antibiotics. Of particular value would be antibiotics against opportunistic fungi, protozoa, and those bacteria resistant to the antibiotics in current use.
 b) Enzymes: For instance, the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.
 c) Antibodies: For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or lead to the development of related diagnostic agents or compounds useful in therapeutic treatments such as for auto-immune diseases (e.g., by blocking the binding of the "self" antibodies).
 d) Nucleic Acids: Sequences of nucleic acids may be synthesized to establish DNA or RNA binding sequences.
 e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides are described in, for example, U.S. application Ser. No. 404,920, which is incorporated herein by reference for all purposes.
 f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. Other examples are the vasoconstrictive hormone receptors; determination of those ligands which bind to a receptor may lead to the development of drugs to control blood pressure.
 g) Opiate receptors: Determination of ligands which bind to the opiate receptors in the brain is useful in the development of less-addictive replacements for morphine and related drugs.
8. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.
9. Protective Group: A material which is chemically bound to a monomer unit and which may be removed upon selective exposure to an activator such as electromagnetic radiation. Examples of protective groups with utility herein include those comprising nitropiperonyl, pyrenyl-methoxy-carbonyl, nitroveratryl, nitrobenzyl, dimethyl dimethoxybenzyl, 5-bromo-7-nitroindolinyl, o-hydroxy-α-methyl cinnamoyl, and 2-oxymethylene anthraquinone.
10. Predefined Region: A predefined region is a localized area on a surface which is, was, or is intended to be activated for formation of a polymer. The predefined region may have any convenient shape, e.g., circular, rectangular, elliptical, wedge-shaped, etc. For the sake of brevity herein, "predefined regions" are sometimes referred to simply as "regions."
11. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor.
12. Activator refers to an energy source adapted to render a group active and which is directed from a source to a predefined location on a substrate. A primary illustration of an activator is light. Other examples of activators include ion beams, electric fields, magnetic fields, electron beams, x-ray, and the like.
13. Binary Synthesis Strategy refers to an ordered strategy for parallel synthesis of diverse polymer sequences by sequential addition of reagents which may be represented by a reactant matrix, and a switch matrix, the product of which is a product matrix. A reactant matrix is a 1×n matrix of the building blocks to be added. The switch matrix is all or a subset of the binary numbers, preferably ordered, between 1 and n arranged in columns. In preferred embodiments, a binary strategy is one in which at least two successive steps illuminate half of a region of interest on the substrate. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme, but will still be considered to be a binary masking scheme within the definition herein. A binary "masking" strategy is a binary synthesis which uses light to remove protective groups from materials for addition of other materials such as amino acids. In preferred embodiments, selected columns of the switch matrix are arranged in order of increasing binary numbers in the columns of the switch matrix.

14. Linker refers to a molecule or group of molecules attached to a substrate and spacing a synthesized polymer from the substrate for exposure/binding to a receptor.

II. General

The present invention provides synthetic strategies and devices for the creation of large scale chemical diversity. Solid-phase chemistry, photolabile protecting groups, and photolithography are brought together to achieve light-directed spatially-addressable parallel chemical synthesis in preferred embodiments.

The invention is described herein for purposes of illustration primarily with regard to the preparation of peptides and nucleotides, but could readily be applied in the preparation of other polymers. Such polymers include, for example, both linear and cyclic polymers of nucleic acids, polysaccharides, phospholipids, and peptides having either $\alpha$-, $\beta$-, or $\omega$-amino acids, hetero-polymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. It will be recognized further, that illustrations herein are primarily with reference to C- to N-terminal synthesis, but the invention could readily be applied to N- to C-terminal synthesis without departing from the scope of the invention.

A. Deprotection and Addition

The present invention uses a masked light source or other activator to direct the simultaneous synthesis of many different chemical compounds. FIG. 1 is a flow chart illustrating the process of forming chemical compounds according to one embodiment of the invention. Synthesis occurs on a solid support 2. A pattern of illumination through a mask 4a using a light source 6 determines which regions of the support are activated for chemical coupling. In one preferred embodiment activation is accomplished by using light to remove photolabile protecting groups from selected areas of the substrate.

After deprotection, a first of a set of building blocks (indicated by "A" in FIG. 1), each bearing a photolabile protecting group (indicated by "X") is exposed to the surface of the substrate and it reacts with regions that were addressed by light in the preceding step. The substrate is then illuminated through a second mask 4b, which activates another region for reaction with a second protected building block "B". The pattern of masks used in these illuminations and the sequence of reactants define the ultimate products and their locations, resulting in diverse sequences at pre-defined locations, as shown with the sequences ACEG and BDFH in the lower portion of FIG. 1. Preferred embodiments of the invention take advantage of combinatorial masking strategies to form a large number of compounds in a small number of chemical steps.

A high degree of miniaturization is possible because the density of compounds is determined largely with regard to spatial addressability of the activator, in one case the diffraction of light. Each compound is physically accessible and its position is precisely known. Hence, the array is spatially-addressable and its interactions with other molecules can be assessed.

In a particular embodiment shown in FIG. 1, the substrate contains amino groups that are blocked with a photolabile protecting group. Amino acid sequences are made accessible for coupling to a receptor by removal of the photoprotective groups.

When a polymer sequence to be synthesized is for example, a polypeptide, amino groups at the ends of linkers attached to a glass substrate are derivatized with nitroveratryloxycarbonyl (NVOC), a photoremovable protecting group. The linker molecules may be, for example, aryl acetylene, ethylene glycol oligomers containing from 2–10 monomers, diamines, diacids, amino acids, or combinations thereof. Photodeprotection is effected by illumination of the substrate through, for example, a mask wherein the pattern has transparent regions with dimensions of, for example, less than 1 cm², $10^{-1}$ cm², $10^{-2}$ cm², $10^{-3}$ cm², $10^{-4}$ cm², $10^{-5}$ cm², $10^{-6}$ cm², $10^{-7}$ cm², $10^{-8}$ cm², or $10^{-10}$ cm². In a preferred embodiment, the regions are between about 10×10 μm and 500×500 μm. According to some embodiments, the masks are arranged to produce a checkerboard array of polymers, although any one of a variety of geometric configurations may be utilized.

1. EXAMPLE

In one example of the invention, free amino groups were fluorescently labelled by treatment of the entire substrate surface with fluorescein isothiocynate (FITC) after photodeprotection. Glass microscope slides were cleaned, aminated by treatment with 0.1% aminopropyltriethoxysilane in 95% ethanol, and incubated at 110° C. for 20 min. The aminated surface of the slide was then exposed to a 30 mM solution of the N-hydroxysuccinimide ester of NVOC-GABA (nitroveratryloxycarbonyl-τ-amino butyric acid) in DMF. The NVOC protecting group was photolytically removed by imaging the 365 nm output from a Hg arc lamp through a chrome on glass 100 μm checkerboard mask onto the substrate for 20 min at a power density of 12 mW/cm². The exposed surface was then treated with 1 mM FITC in DMF. The substrate surface was scanned in an epi-fluorescence microscope (Zeiss Axioskop 20) using 488 nm excitation from an argon ion laser (Spectra-Physics model 2025). The fluorescence emission above 520 nm was detected by a cooled photomultiplier (Hamamatsu 943-02) operated in a photon counting mode. Fluorescence intensity was translated into a color display with red in the highest intensity and black in the lowest intensity areas. The presence of a high-contrast fluorescent checkerboard pattern of 100×100 μm elements revealed that free amino groups were generated in specific regions by spatially-localized photodeprotection.

2. EXAMPLE

Figure 2:
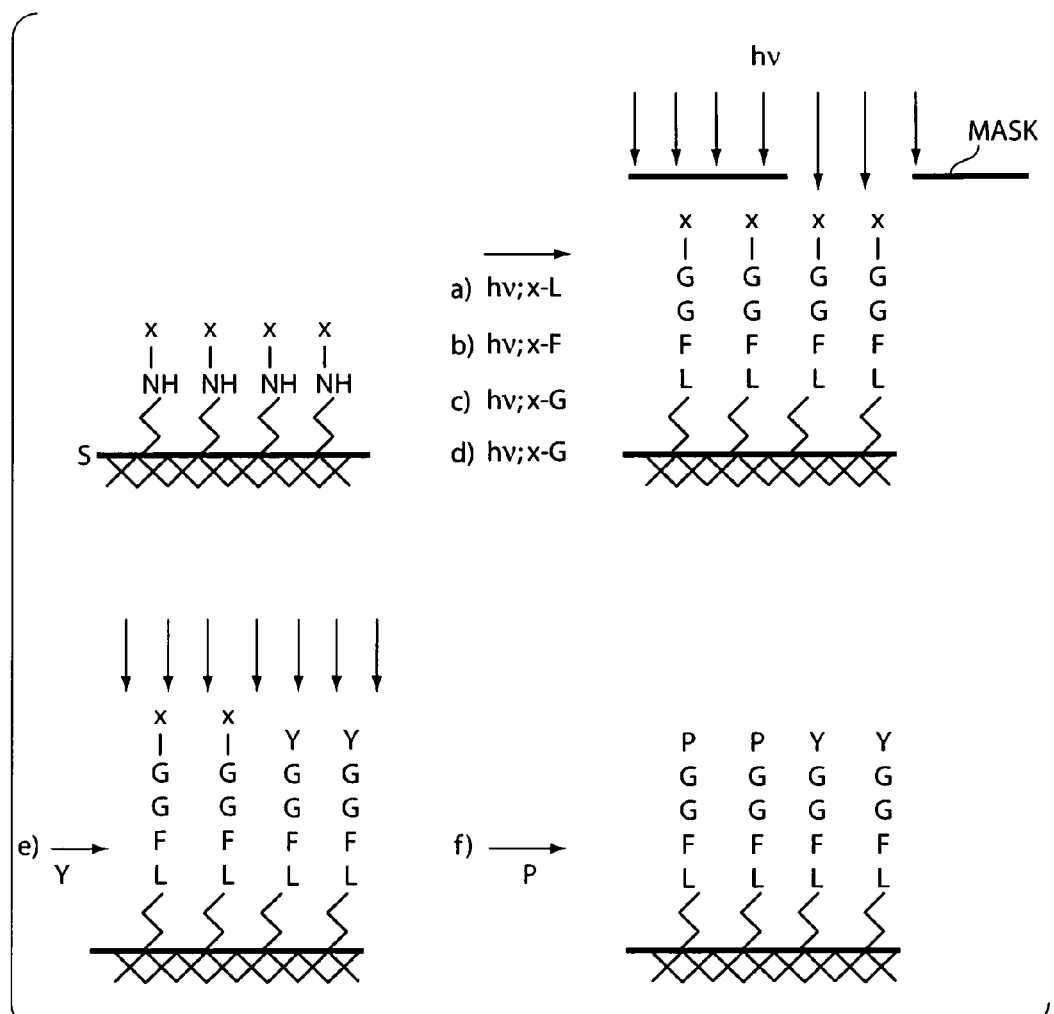
FIG. 2 schematically illustrates one example of light-directed peptide synthesis.

FIG. 2 is a flow chart illustrating another example of the invention. Carboxy-activated NVOC-leucine was allowed to react with an aminated substrate. The carboxy activated HOBT ester of leucine and other amino acids used in this synthesis was formed by mixing 0.25 mmol of the NVOC amino protected amino acid with 37 mg HOBT (1-hydroxy-benzotriazole), 111 mg BOP (benzotriazolyl-n-oxy-tris (dimethylamino)-phosphoniumhexa-fluorophosphate) and 86 μl DIEA (diisopropylethylamine) in 2.5 ml DMF. The NVOC protecting group was removed by uniform illumination. Carboxy-activated NVOC-phenylalanine was coupled to the exposed amino groups for 2 hours at room temperature, and then washed with DMF and methylene chloride. Two unmasked cycles of photodeprotection and coupling with carboxy-activated NVOC-glycine were carried out. The surface was then illuminated through a chrome on glass 50 μm checkerboard pattern mask. Carboxy-activated Nα-tBOC-O-tButyl-L-tyrosine was then added. The entire surface was uniformly illuminated to photolyze the remaining NVOC groups. Finally, carboxy-activated NVOC-L-proline was added, the NVOC group was removed by illumination, and the t-BOC and t-butyl protecting groups were removed with TFA. After removal of the protecting groups, the surface consisted of a 50 μm checkerboard array of Tyr-Gly-Gly-Phe-Leu (YGGFL) and Pro-Gly-Gly-Phe-Leu (PGGFL).

B. Antibody Recognition

In one preferred embodiment the substrate is used to determine which of a plurality of amino acid sequences is recognized by an antibody of interest.

1. EXAMPLE

In one example, the array of pentapeptides in the example illustrated in FIG. 2 was probed with a mouse monoclonal antibody directed against β-endorphin. This antibody (called 3E7) is known to bind YGGFL and YGGFK with nanomolar affinity and is discussed in Meo et al., *Proc. Natl. Acad. Sci. USA* (1983) 80:4084, which is incorporated by reference herein for all purposes. This antibody requires the amino terminal tyrosine for high affinity binding. The array of peptides formed as described in FIG. 2 was incubated with a 2 μg/ml mouse monoclonal antibody (3E7) known to recognize YGGFL. 3E7 does not bind PGGFL. A second incubation with fluoresceinated goat anti-mouse antibody labeled the regions that bound 3E7. The surface was scanned with an epi-fluorescence microscope. The results showed alternating bright and dark 50 μm squares indicating that YGGFL and PGGFL were synthesized in geometric array determined by the mask. A high contrast (>12:1 intensity ratio) fluorescence checkerboard image shows that (a) YGGFL and PGGFL were synthesized in alternate 50 μm squares, (b) YGGFL attached to the surface is accessible for binding to antibody 3E7, and (c) antibody 3E7 does not bind to PGGFL.

Figure 3:
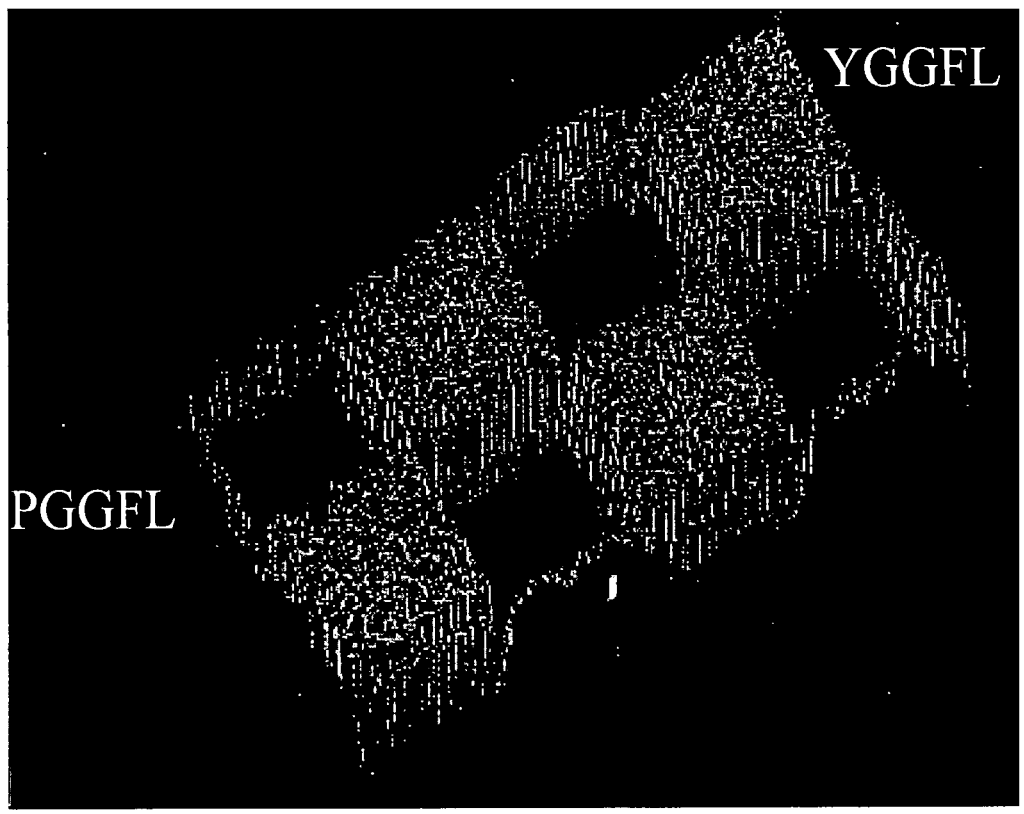
FIG. 3 is a three-dimensional representation of a portion of the checkerboard array of YGGFL and PGGFL.

A three-dimensional representation of the fluorescence intensity data in a portion of the checkboard is shown in FIG. 3. This figure shows that the border between synthesis sites is sharp. The height of each spike in this display is linearly proportional to the integrated fluorescence intensity in a 2.5 μm pixel. The transition between PGGFL and YGGFL occurs within two spikes (5 μm). There is little variation in the fluorescence intensity of different YGGFL squares. The mean intensity of sixteen YGGFL synthesis sites was 2.03× $10^5$ counts and the standard deviation was 9.6×$10^3$ counts.

III. Synthesis

A. Reactor System

Figure 4:
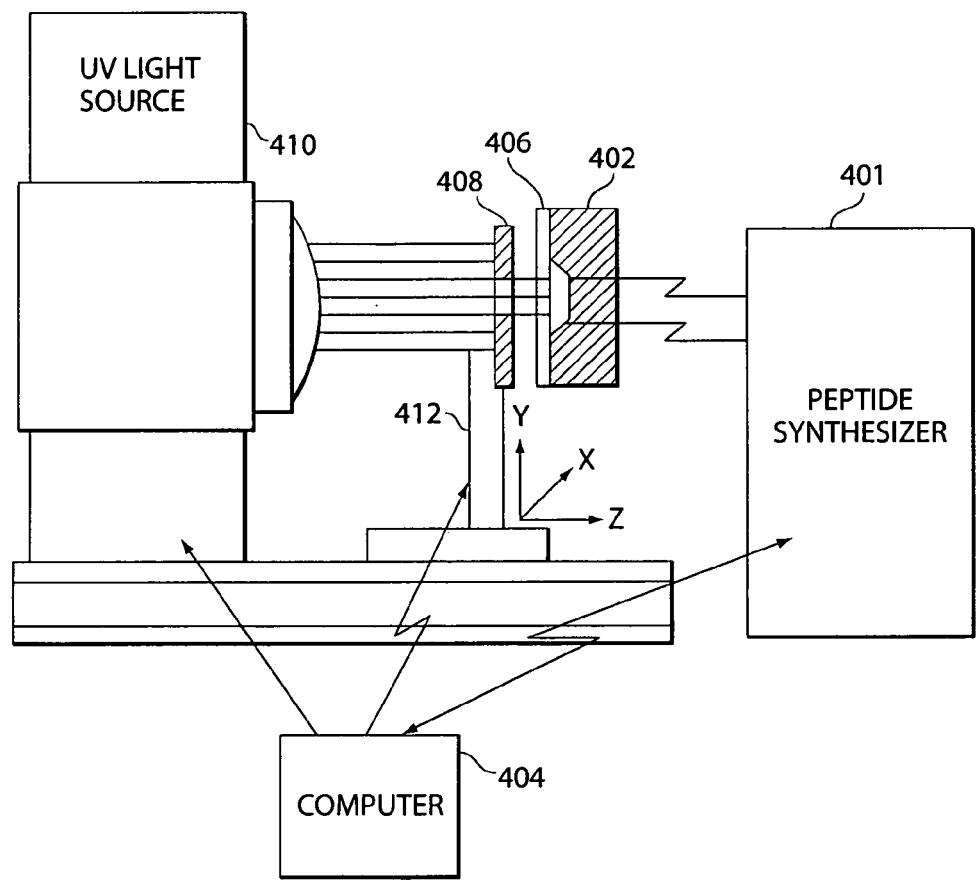
FIG. 4 schematically illustrates the software for the automated system for synthesizing diverse polymer sequences.

FIG. 4 schematically illustrates a device used to synthesize diverse polymer sequences on a substrate. The device includes an automated peptide synthesizer 401. The automated peptide synthesizer is a device which flows selected reagents through a flow cell 402 under the direction of a computer 404. In a preferred embodiment the synthesizer is an ABI Peptide Synthesizer, model no. 431A. The computer may be selected from a wide variety of computers or discrete logic including for, example, an IBM PC-AT or similar computer linked with appropriate internal control systems in the peptide synthesizer. The PC is provided with signals from the board computer indicative of, for example, the end of a coupling cycle.

Substrate 406 is mounted on the flow cell, forming a cavity between the substrate and the flow cell. Selected reagents flow through this cavity from the peptide synthesizer at selected times, forming an array of peptides on the face of the substrate in the cavity. Mounted above the substrate, and preferably in contact with the substrate is a mask 408. Mask 408 is transparent in selected regions to a selected wavelength of light and is opaque in other regions to the selected wavelength of light. The mask is illuminated with a light source 410 such as a UV light source. In one specific embodiment the light source 410 is a model no. 82420 made by oriel. The mask is held and translated by an x-y-z translation stage 412 such as an x-y translation stage made by Newport Corp. The computer coordinates action of the peptide synthesizer, x-y translation stage, and light source. Of course, the invention may be used in some embodiments with translation of the substrate instead of the mask.

In operation, the substrate is mounted on the reactor cavity. The slide, with its surface protected by a suitable photo removable protective group, is exposed to light at selected locations by positioning the mask and illuminating the light source for a desired period of time (such as, for example, 1 sec to 60 min in the case of peptide synthesis). A selected peptide or other monomer/polymer is pumped through the reactor cavity by the peptide synthesizer for binding at the selected locations on the substrate. After a selected reaction time (such as about 1 sec to 300 min in the case of peptide reactions) the monomer is washed from the system, the mask is appropriately repositioned or replaced, and the cycle is repeated. In most embodiments of the invention, reactions may be conducted at or near ambient temperature.

Figure 5A:
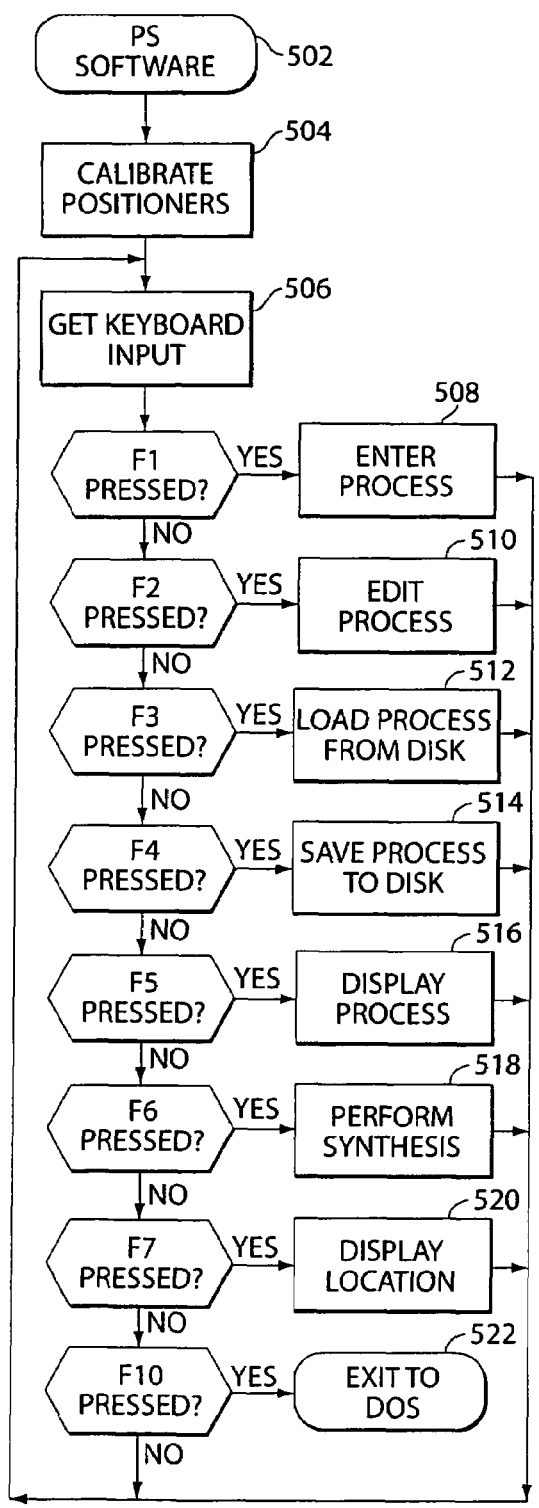
FIGS. 5a and 5b illustrate operation of a program for polymer sythesis.
Figure 5B:
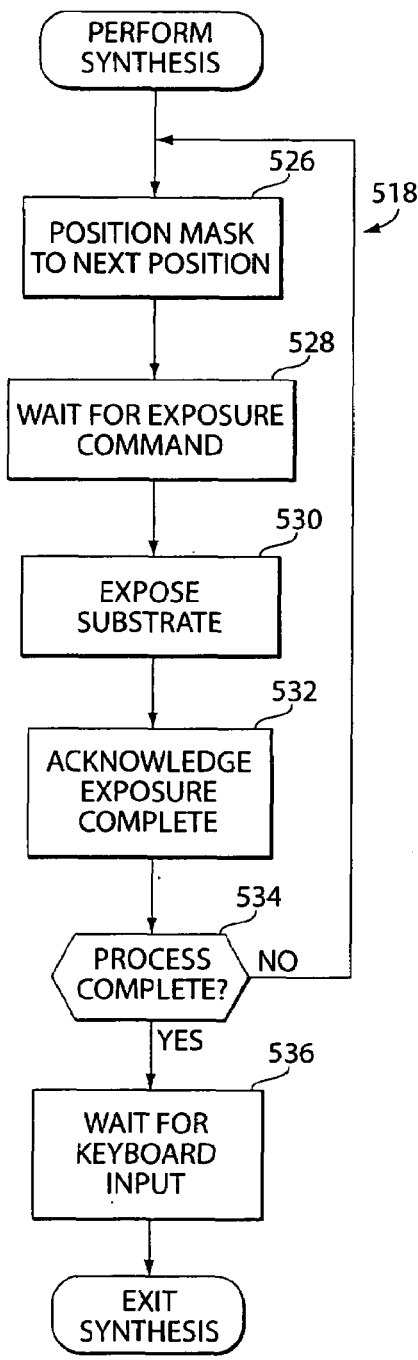

FIGS. 5a and 5b are flow charts of the software used in operation of the reactor system. At step 502 the peptide synthesis software is initialized. At step 504 the system calibrates positioners on the x-y translation stage and begins a main loop. At step 506 the system determines which, if any, of the function keys on the computer have been pressed. If F1 has been pressed, the system prompts the user for input of a desired synthesis process. If the user enters F2, the system allows a user to edit a file for a synthesis process at step 510. If the user enters F3 the system loads a process from a disk at step 512. If the user enters F4 the system saves an entered or edited process to disk at step 514. If the user selects F5 the current process is displayed at step 516 while selection of F6 starts the main portion of the program, i.e., the actual synthesis according to the selected process. If the user selects F7 the system displays the location of the synthesized peptides, while pressing F10 returns the user to the disk operating system.

FIG. 5b illustrates the synthesis step 518 in greater detail. The main loop of the program is started in which the system first moves the mask to a next position at step 526. During the main loop of the program, necessary chemicals flow through the reaction cell under the direction of the on-board computer in the peptide synthesizer. At step 528 the system then waits for an exposure command and, upon receipt of the exposure command exposes the substrate for a desired time at step 530. When an acknowledge of exposure complete is received at step 532 the system determines if the process is complete at step 534 and, if so, waits for additional keyboard input at step 536 and, thereafter, exits the perform synthesis process.

A computer program used for operation of the system described above is included as microfiche Appendix A (Copyright, 1990, Affymax Technologies N.V., all rights reserved). The program is written in Turbo C++ (Borland Int'l) and has been implemented in an IBM compatible system. The motor control software is adapted from software produced by Newport Corporation. It will be recognized that a large variety of programming languages could be utilized without departing from the scope of the invention herein. Certain calls are made to a graphics program in "Programmer Guide to PC and PS2 Video Systems" (Wilton, Microsoft Press, 1987), which is incorporated herein by reference for all purposes.

Alignment of the mask is achieved by one of two methods in preferred embodiments. In a first embodiment—the system relies upon relative alignment of the various components, which is normally acceptable since x-y-z translation stages are capable of sufficient accuracy for the purposes herein. In alternative embodiments, alignment marks on the substrate are coupled to a CCD device for appropriate alignment.

According to some embodiments, pure reagents are not added at each step, or complete photolysis of the protective groups is not provided at each step. According to these embodiments, multiple products will be formed in each synthesis site. For example, if the monomers A and B are mixed during a synthesis step, A and B will bind to deprotected regions, roughly in proportion to their concentration in solution. Hence, a mixture of compounds will be formed in a synthesis region. A substrate formed with mixtures of compounds in various synthesis regions may be used to perform, for example, an initial screening of a large number of compounds, after which a smaller number of compounds in regions which exhibit high binding affinity are further screened. Similar results may be obtained by only partially photylizing a region, adding a first monomer, re-photylizing the same region, and exposing the region to a second monomer.

B. Binary Synthesis Strategy

In a light-directed chemical synthesis, the products formed depend on the pattern and order of masks, and on the order of reactants. To make a set of products there will in general be "n" possible masking schemes. In preferred embodiments of the invention herein a binary synthesis strategy is utilized. The binary synthesis strategy is illustrated herein primarily with regard to a masking strategy, although it will be applicable to other polymer synthesis strategies such as the pin strategy, and the like.

In a binary synthesis strategy, the substrate is irradiate with a first mask, exposed to a first building block, irradiated with a second mask, exposed to a second building block, etc. Each combination of masked irradiation and exposure to a building block is referred to herein as a "cycle."

In a preferred binary masking scheme, the masks for each cycle allow irradiation of half of a region of interest on the substrate and protection of the remaining half of the region of interest. By "half" it is intended herein not to mean exactly one-half the region of interest, but instead a large fraction of the region of interest such as from about 30 to 70 percent of the region of interest. It will be understood that the entire masking scheme need not take a binary form; instead non-binary cycles may be introduced as desired between binary cycles.

In preferred embodiments of the binary masking scheme, a given cycle illuminates only about half of the region which was illuminated in a previous cycle, while protecting the remaining half of the illuminated portion from the previous cycle. conversely, in such preferred embodiments, a given cycle illuminates half of the region which was protected in the previous cycle and protects half the region which was protected in a previous cycle.

In the synthesis strategy disclosed herein, the longest length (l) of the synthesized polymers is $l=n/a$; where n is the number of cycles and a is the number of chemical building blocks (note that a given building block may be repeated). The total number of possible compounds synthesized (k) will be $k=a^l$. For example, if $a=20$ and $l=5$, $n=100$ and $k=3.2\times10^5$.

The synthesis strategy is most readily illustrated and handled in matrix notation. At each synthesis site, the determination of whether to add a given monomer is a binary process. Therefore, each product element $P_j$ is given by the dot product of two vectors, a chemical reactant vector, e.g., $C=[A,B,C,D]$, and a binary vector $\sigma_j$. Inspection of the products in the example below for a four-step synthesis, shows that in one four-step synthesis $\sigma_1=[1,0,1,0]$, $\sigma_2=[1,0,0,1]$, $\sigma_3=[0,1,1,0]$, and $\sigma_4=[0,1,0,1]$, where a 1 indicates illumination and a 0 indicates protection. Therefore, it becomes possible to build a "switch matrix" S from the column vectors $\sigma_j$ (j=1,k where k is the number of products).

$$S = \begin{matrix} \sigma_1 & \sigma_2 & \sigma_3 & \sigma_4 \\ 1 & 1 & 0 & 0 \\ 0 & 0 & 1 & 1 \\ 1 & 0 & 1 & 0 \\ 0 & 1 & 0 & 1 \end{matrix}$$

The outcome P of a synthesis is simply $P=CS$, the product of the chemical reactant matrix and the switch matrix.

The switch matrix for an n-cycle synthesis yielding k products has n rows and k columns. An important attribute of S is that each row specifies a mask. A two-dimensional mask $m_j$ for the jth chemical step of a synthesis is obtained directly from the jth row of S by placing the elements $s_{j1}, \ldots s_{jk}$ into, for example, a square format. The particular arrangement below provides a square format, although linear or other arrangements may be utilized.

$$S = \begin{matrix} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{matrix} \qquad m_j = \begin{matrix} s_{j1} & s_{j2} \\ s_{j3} & s_{j4} \end{matrix}$$

Of course, compounds formed in a light-activated synthesis can be positioned in any defined geometric array. A square or rectangular matrix is convenient but not required. The rows of the switch matrix may be transformed into any convenient array as long as equivalent transformations are used for each row.

For example, the masks in the four-step synthesis below are then denoted by:

$$m_1 = \begin{matrix} 1 & 1 \\ 0 & 0 \end{matrix} \quad m_2 = \begin{matrix} 0 & 0 \\ 1 & 1 \end{matrix} \quad m_3 = \begin{matrix} 1 & 0 \\ 1 & 0 \end{matrix} \quad m_4 = \begin{matrix} 0 & 1 \\ 0 & 1 \end{matrix}$$

where 1 denotes illumination (activation) and 0 denotes no illumination.

The matrix representation is used to generate a desired set of products and product maps in preferred embodiments. Each compound is defined by the product of the chemical vector and a particular switch vector. Therefore, for each synthesis address, one simply saves the switch vector, assembles all of them into a switch matrix, and extracts each of the rows to form the masks.

In some cases, particular product distributions or a maximal number of products are desired. For example, for C=[A,B,C,D], any switch vector ($\sigma_j$) consists of four bits. Sixteen four-bit vectors exist. Hence, a maximum of 16 different products can be made by sequential addition of the reagents [A,B,C,D]. These 16 column vectors can be assembled in 16! different ways to form a switch matrix. The order of the column vectors defines the masking patterns, and therefore, the spatial ordering of products but not their makeup. One ordering of these columns gives the following switch matrix (in which "null" (Ø) additions are included in brackets for the sake of completeness, although such null additions are elsewhere ignored herein):

$$S = \begin{matrix} & \sigma 1 & & & & & & & & & & & & & & \sigma_{16} & \\ & 1 & 1 & 1 & 1 & 1 & 1 & 1 & 1 & 0 & 0 & 0 & 0 & 0 & 0 & 0 & 0 & A \\ [ & 0 & 0 & 0 & 0 & 0 & 0 & 0 & 0 & 1 & 1 & 1 & 1 & 1 & 1 & 1 & 1] & \emptyset \\ & 1 & 1 & 1 & 1 & 0 & 0 & 0 & 0 & 1 & 1 & 1 & 1 & 0 & 0 & 0 & 0 & B \\ [ & 0 & 0 & 0 & 0 & 1 & 1 & 1 & 1 & 0 & 0 & 0 & 0 & 1 & 1 & 1 & 1] & \emptyset \\ & 1 & 1 & 0 & 0 & 1 & 1 & 0 & 0 & 1 & 1 & 0 & 0 & 1 & 1 & 0 & 0 & C \\ [ & 0 & 0 & 1 & 1 & 0 & 0 & 1 & 1 & 0 & 0 & 1 & 1 & 0 & 0 & 1 & 1] & \emptyset \\ & 1 & 0 & 1 & 0 & 1 & 0 & 1 & 0 & 1 & 0 & 1 & 0 & 1 & 0 & 1 & 0 & D \\ [ & 0 & 1 & 0 & 1 & 0 & 1 & 0 & 1 & 0 & 1 & 0 & 1 & 0 & 1 & 0 & 1] & \emptyset \end{matrix}$$

The columns of S according to this aspect of the invention are the binary representations of the numbers 15 to 0. The sixteen products of this binary synthesis are ABCD, ABC, ABD, AB, ACD, AC, AD, A, BCD, BC, BD, B, CD, C, D, and ø (null). Also note that each of the switch vectors from the four-step synthesis masks above (and hence the synthesis products) are present in the four bit binary switch matrix. (See columns 6, 7, 10, and 11)

This synthesis procedure provides an easy way for mapping the completed products. The products in the various locations on the substrate are simply defined by the columns of the switch matrix (the first column indicating, for example, that the product ABCD will be present in the upper left-hand location of the substrate). Furthermore, if only selected desired products are to be made, the mask sequence can be derived by extracting the columns with the desired sequences. For example, to form the product set ABCD, ABD, ACD, AD, BCD, BD, CD, and D, the masks are formed by use of a switch matrix with only the 1st, 3rd, 5th, 7th, 9th, 11th, 13th, and 15th columns arranged into the switch matrix:

$$S = \begin{matrix} 1 & 1 & 1 & 1 & 0 & 0 & 0 & 0 \\ 1 & 1 & 0 & 0 & 1 & 1 & 0 & 0 \\ 1 & 0 & 1 & 0 & 1 & 0 & 1 & 0 \\ 1 & 1 & 1 & 1 & 1 & 1 & 1 & 1 \end{matrix}$$

To form all of the polymers of length 4, the reactant matrix [ABCDABCDABCDABCD] is used. The switch matrix will be formed from a matrix of the binary numbers from 0 to $2^{16}$ arranged in columns. The columns having four monomers are than selected and arranged into a switch matrix. Therefore, it is seen that the binary switch matrix in general will provide a representation of all the products which can be made from an n-step synthesis, from which the desired products are then extracted.

The rows of the binary switch matrix will, in preferred embodiments, have the property that each masking step illuminates half of the synthesis area. Each masking step also factors the preceding masking step; that is, half of the region that was illuminated in the preceding step is again illuminated, whereas the other half is not. Half of the region that was unilluminated in the preceding step is also illuminated, whereas the other half is not. Thus, masking is recursive. The masks are constructed, as described previously, by extracting the elements of each row and placing them in a square array. For example, the four masks in S for a four-step synthesis are:

$$m_1 = \begin{matrix} 1 & 1 & 1 & 1 \\ 1 & 1 & 1 & 1 \\ 0 & 0 & 0 & 0 \\ 0 & 0 & 0 & 0 \end{matrix} \quad m_2 = \begin{matrix} 1 & 1 & 1 & 1 \\ 0 & 0 & 0 & 0 \\ 1 & 1 & 1 & 1 \\ 0 & 0 & 0 & 0 \end{matrix} \quad m_3 = \begin{matrix} 1 & 1 & 0 & 0 \\ 1 & 1 & 0 & 0 \\ 1 & 1 & 0 & 0 \\ 1 & 1 & 0 & 0 \end{matrix} \quad m_4 = \begin{matrix} 1 & 0 & 1 & 0 \\ 1 & 0 & 1 & 0 \\ 1 & 0 & 1 & 0 \\ 1 & 0 & 1 & 0 \end{matrix}$$

The recursive factoring of masks allows the products of a light-directed synthesis to be represented by a polynomial. (Some light activated syntheses can only be denoted by irreducible, i.e., prime polynomials.) For example, the polynomial corresponding to the top synthesis of FIG. 9a (discussed below) is $$P=(A+B)(C+D)$$

A reaction polynomial may be expanded as though it were an algebraic expression, provided that the order of joining of reactants $X_1$ and $X_2$ is preserved ($X_1X_2 \neq X_2X_1$), i.e., the products are not comutative. The product then is AC+AD+BC+BD. The polynomial explicitly specifies the reactants and implicitly specifies the mask for each step. Each pair of parentheses demarcates a round of synthesis. The chemical reactants of a round (e.g., A and B) react at nonoverlapping sites and hence cannot combine with one other. The synthesis area is divided equally amongst the elements of a round (e.g., A is directed to one-half of the area and B to the other half). Hence, the masks for a round (e.g., the masks $m_A$ and $m_B$) are orthogonal and form an orthonormal set. The polynomial notation also signifies that each element in a round is to be joined to each element of the next round (e.g., A with C, A with D, B with C, and B with D). This is accomplished by having $m_C$ overlap $m_A$ an $m_B$ equally, and likewise for $m_D$. Because C and D are elements of a round, $m_C$ and $m_D$ are orthogonal to each other and form an orthonormal set.

The polynomial representation of the binary synthesis described above, in which 16 products are made from 4 reactants, is $$P=(A+\emptyset)(B+\emptyset)(C+\emptyset)(D+\emptyset)$$

which gives ABCD, ABC, ABD, AB, ACD, AC, AD, A, BCD, BC, BD, B, CD, C, D, and Ø when expanded (with the rule that ØX=X and XØ=X, and remembering that joining is ordered). In a binary synthesis, each round contains one reactant and one null (denoted by Ø). Half of the synthesis area receives the reactant and the other half receives nothing. Each mask overlaps every other mask equally.

Binary rounds and non-binary rounds can be interspersed as desired, as in $$P=(A+\emptyset)(B)(C+D30\ \emptyset)(E+F+G)$$

The 18 compounds formed are ABCE, ABCF, ABCG, ABDE, ABDF, ABDG, ABE, ABF, ABG, BCE, BCF, BCG, BDE, BDF, BDG, BE, BF, and BG. The switch matrix S for this 7-step synthesis is $$S = \begin{matrix} 1 & 1 & 1 & 1 & 1 & 1 & 1 & 1 & 1 & 0 & 0 & 0 & 0 & 0 & 0 & 0 & 0 & 0 \\ 1 & 1 & 1 & 1 & 1 & 1 & 1 & 1 & 1 & 1 & 1 & 1 & 1 & 1 & 1 & 1 & 1 & 1 \\ 1 & 1 & 1 & 0 & 0 & 0 & 0 & 0 & 0 & 1 & 1 & 1 & 0 & 0 & 0 & 0 & 0 & 0 \\ 0 & 0 & 0 & 1 & 1 & 1 & 0 & 0 & 0 & 0 & 0 & 0 & 1 & 1 & 1 & 0 & 0 & 0 \\ 1 & 0 & 0 & 1 & 0 & 0 & 1 & 0 & 0 & 1 & 0 & 0 & 1 & 0 & 0 & 1 & 0 & 0 \\ 0 & 1 & 0 & 0 & 1 & 0 & 0 & 1 & 0 & 0 & 1 & 0 & 0 & 1 & 0 & 0 & 1 & 0 \\ 0 & 0 & 1 & 0 & 0 & 1 & 0 & 0 & 1 & 0 & 0 & 1 & 0 & 0 & 1 & 0 & 0 & 1 \end{matrix}$$

The round denoted by (B) places B in all products because the reaction area was uniformly activated (the mask for B consisted entirely of 1's).

The number of compounds k formed in a synthesis consisting of r rounds, in which the ith round has $b_i$ chemical reactants and $z_i$ nulls, is $$k=\Sigma(b_i+z_i)$$

and the number of chemical steps n is $$n=\Sigma b_i$$

The number of compounds synthesized when b=a and z=0 in all rounds is $a^{n/a}$, compared with $2^n$ for a binary synthesis. For n=20 and a=5, 625 compounds (all tetrameres) would be formed, compared with $1.049 \times 10^6$ compounds in a binary synthesis with the same number of chemical steps.

It should also be noted that rounds in a polynomial can be nested, as in $$(A+(B+\emptyset)(C+\emptyset))(D+\emptyset)$$

The products are AD, BCD, BD, CD, D, A, BC, B, C, and Ø.

Binary syntheses are attractive for two reasons. First, they generate the maximal number of products ($2^n$) for a given number of chemical steps (n). For four reactants, 16 compounds are formed in the binary synthesis, whereas only 4 are made when each round has two reactants. A 10-step binary synthesis yields 1,024 compounds, and a 20-step synthesis yields 1,048,576. Second, products formed in a binary synthesis are a complete nested set with lengths ranging from 0 to n. All compounds that can be formed by deleting one or more units from the longest product (the n-mer) are present. Contained within the binary set are the smaller sets that would be formed from the same reactants using any other set of masks (e.g., AC, AD, BC, and BD formed in the synthesis shown in FIG. 6 are present in the set of 16 formed by the binary synthesis). In some cases, however, the experimentally achievable spatial resolution may not suffice to accommodate all the compounds formed. Therefore, practical limitations may require one to select a particular subset of the possible switch vectors for a given synthesis.

1. EXAMPLE

Figure 6A:
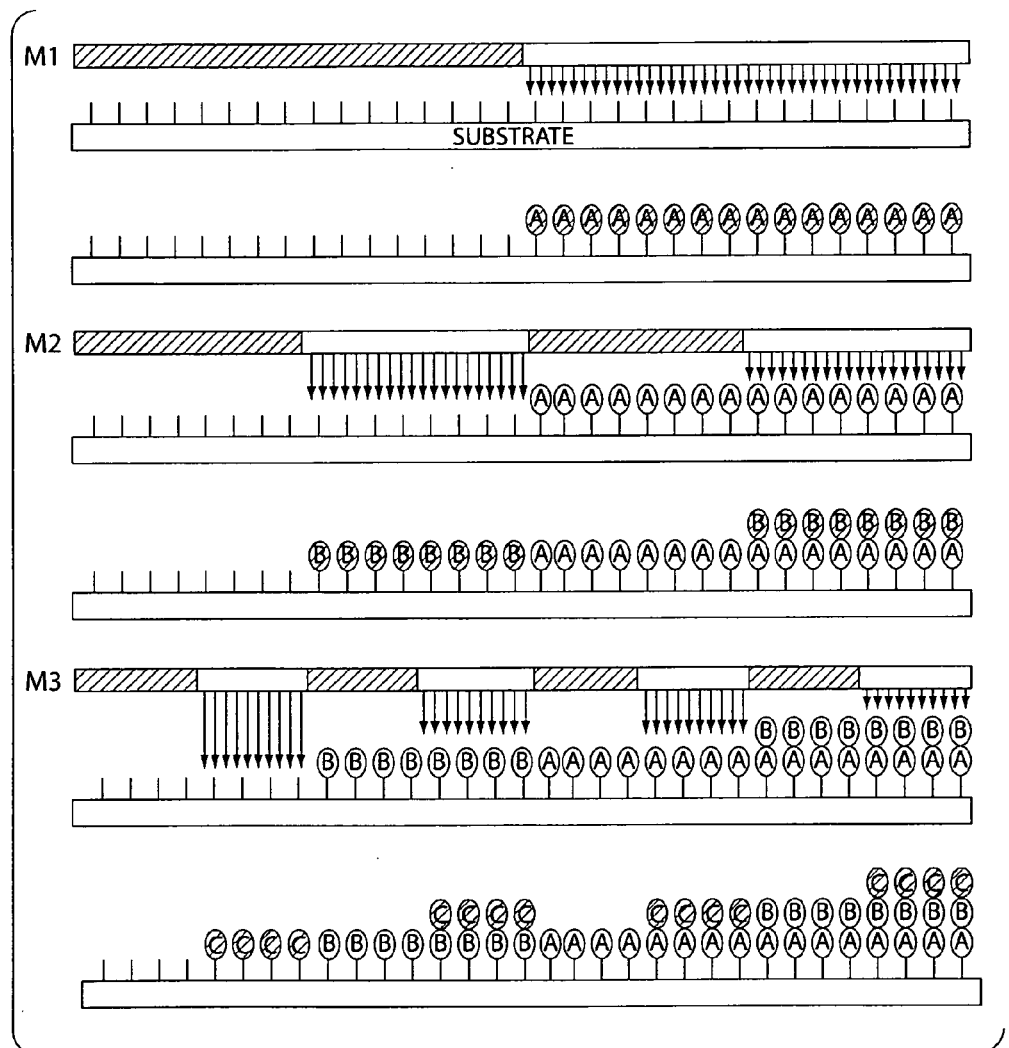
FIGS. 6a and 6b are schematic illustrations of a "pure" binary masking strategy.
Figure 6B:
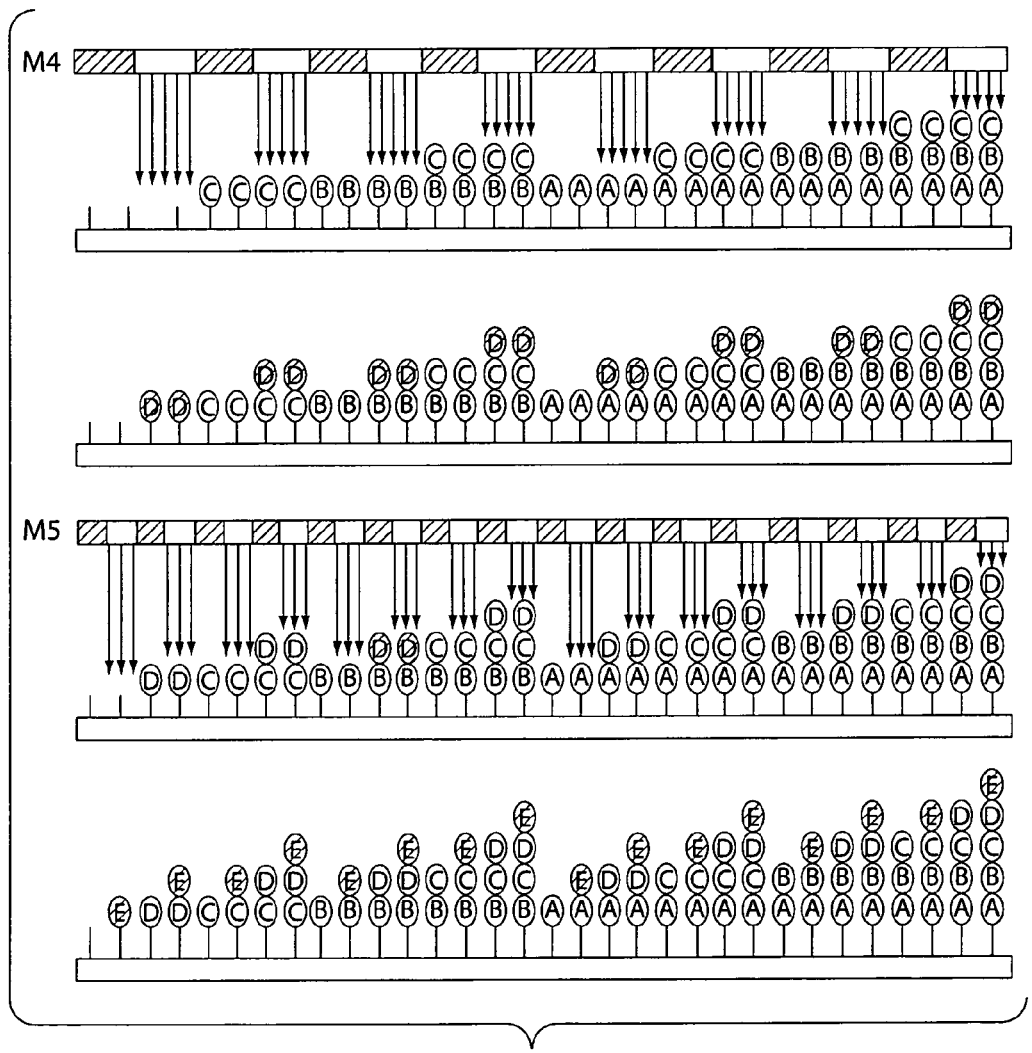

FIGS. 6a & 6b illustrate a synthesis with binary masking scheme. The binary masking scheme provides the greatest-number of sequences for a given number of cycles. According to this embodiment, a mask m1 allows illumination of half of the substrate. The substrate is then exposed to the building block A, which binds at the illuminated regions.

Thereafter, the mask m2 allows illumination of half of the previously illuminated region, while protecting half of the previously illuminated region. The building block B is then added, which binds at the illuminated regions from m2.

The process continues with masks m3, m4, and m5, resulting in the product array shown in the bottom portion of the figure. The process generates 32 (2 raised to the power of the number of monomers) sequences with 5 (the number of monomers) cycles.

2. EXAMPLE

Figure 7A:
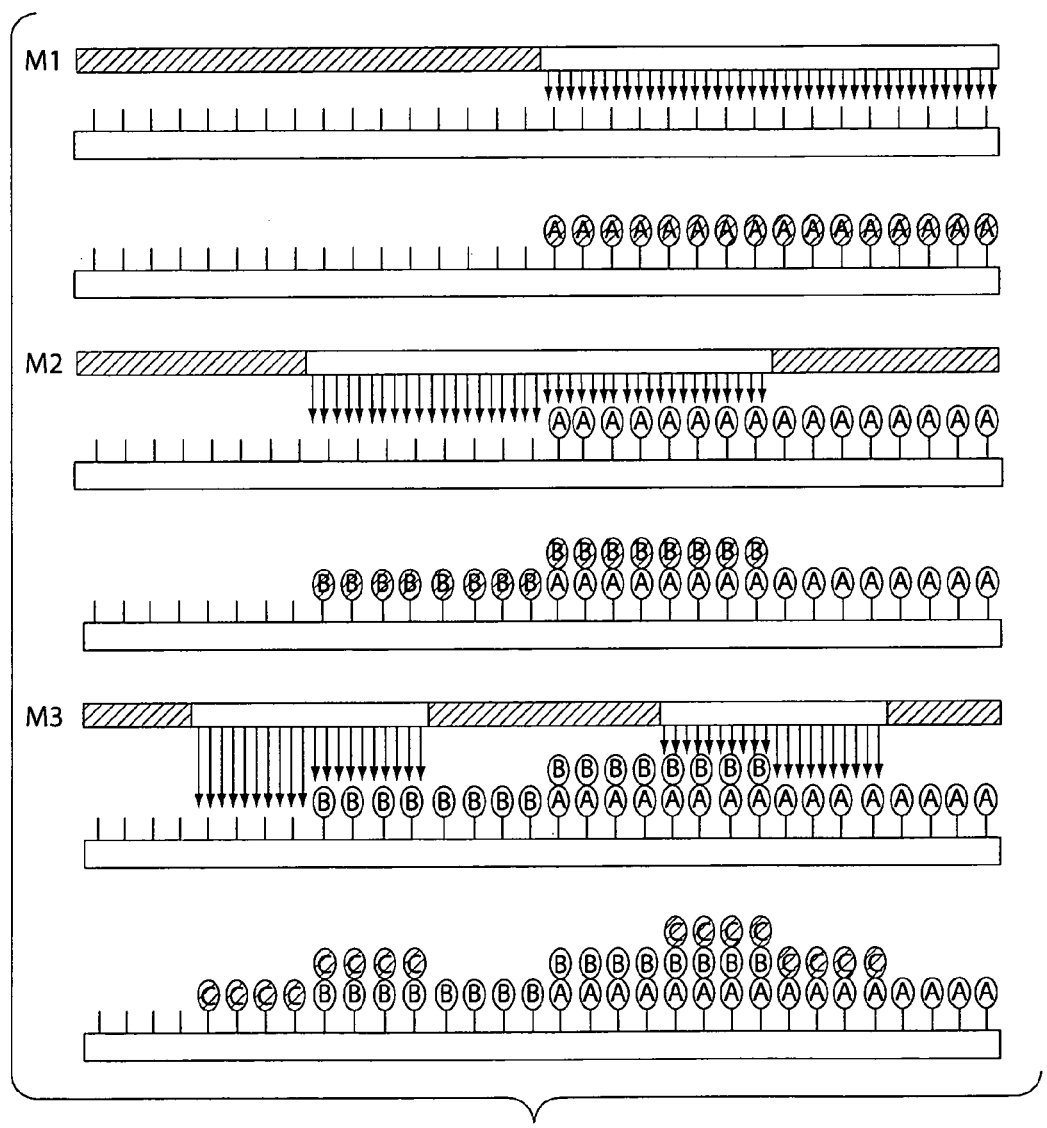
FIGS. 7a and 7b are schematic illustrations of a gray code binary masking strategy.
Figure 7B:
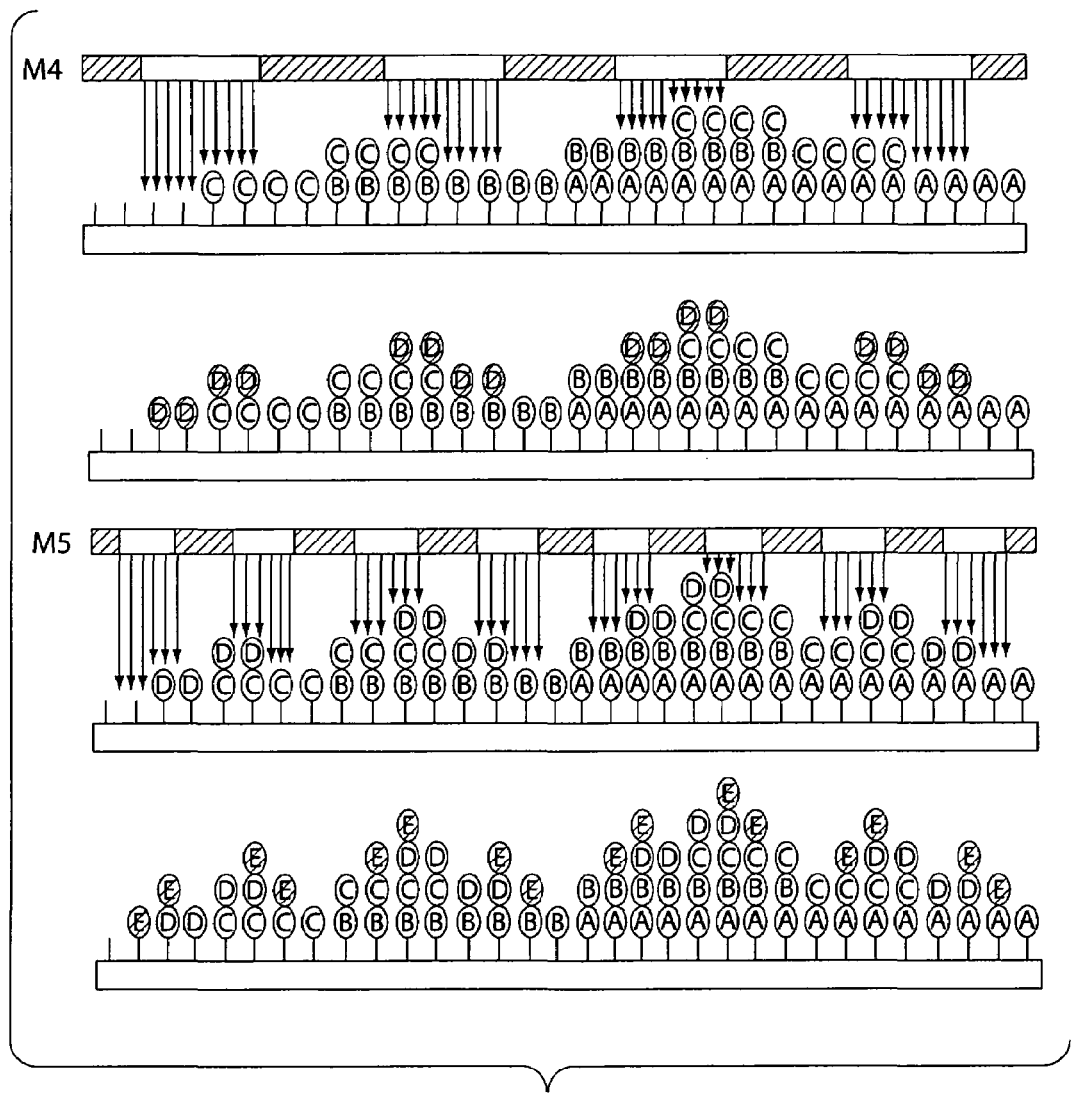

FIGS. 7a & 7b illustrate another preferred binary masking scheme which is referred to herein as the gray code masking scheme. According to this embodiment, the masks m1 to m5 are selected such that a side of any given synthesis region is defined by the edge of only one mask. The site at which the sequence BCDE is formed, for example, has its right edge defined by m5 and its left side formed by mask m4 (and no other mask is aligned on the sides of this site). Accordingly, problems created by misalignment, diffusion of light under the mask and the like will be minimized.

13. EXAMPLE

Figure 8A:
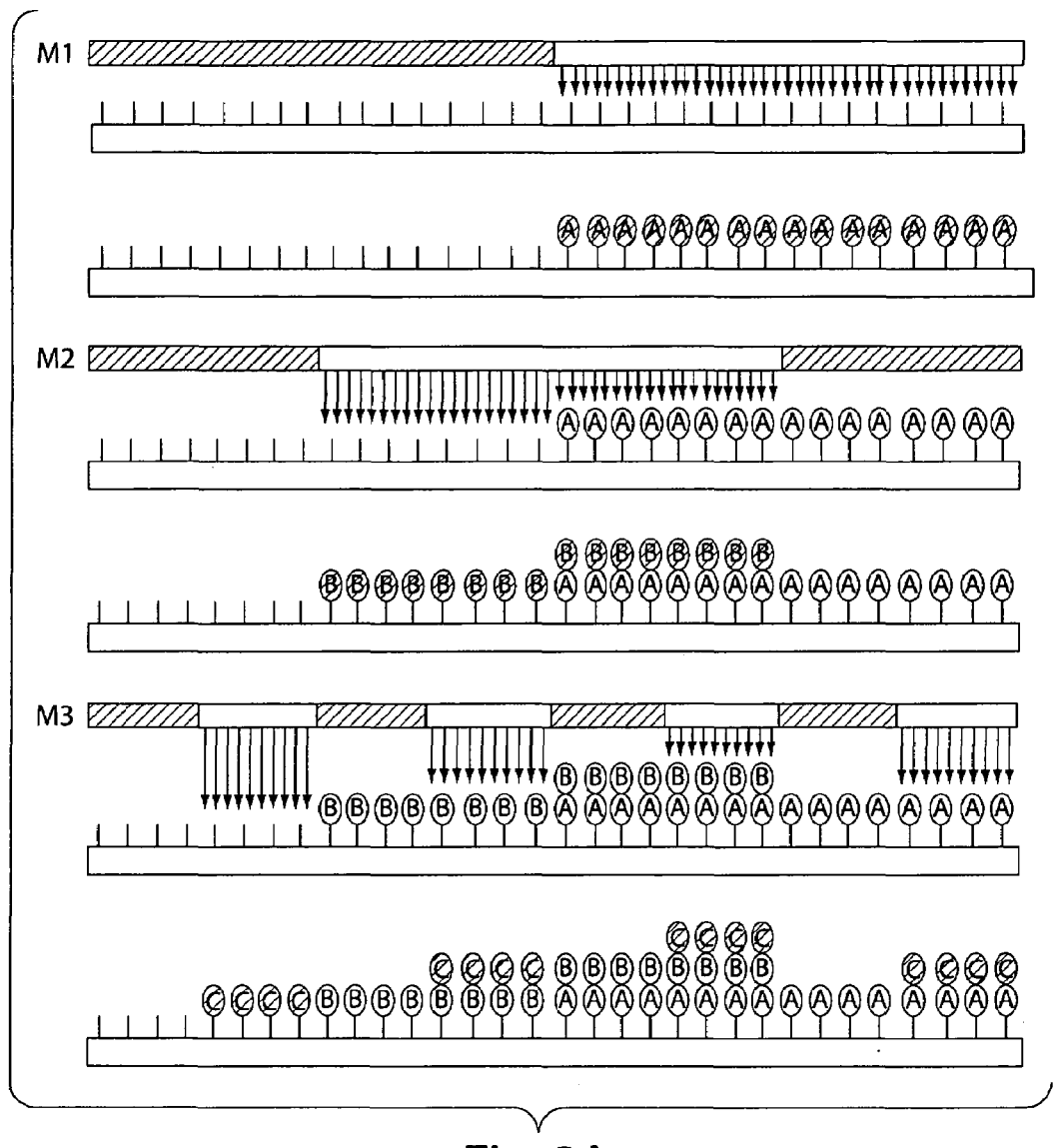
FIGS. 8a and 8b are schematic illustrations of a modified gray code binary masking strategy.
Figure 8B:
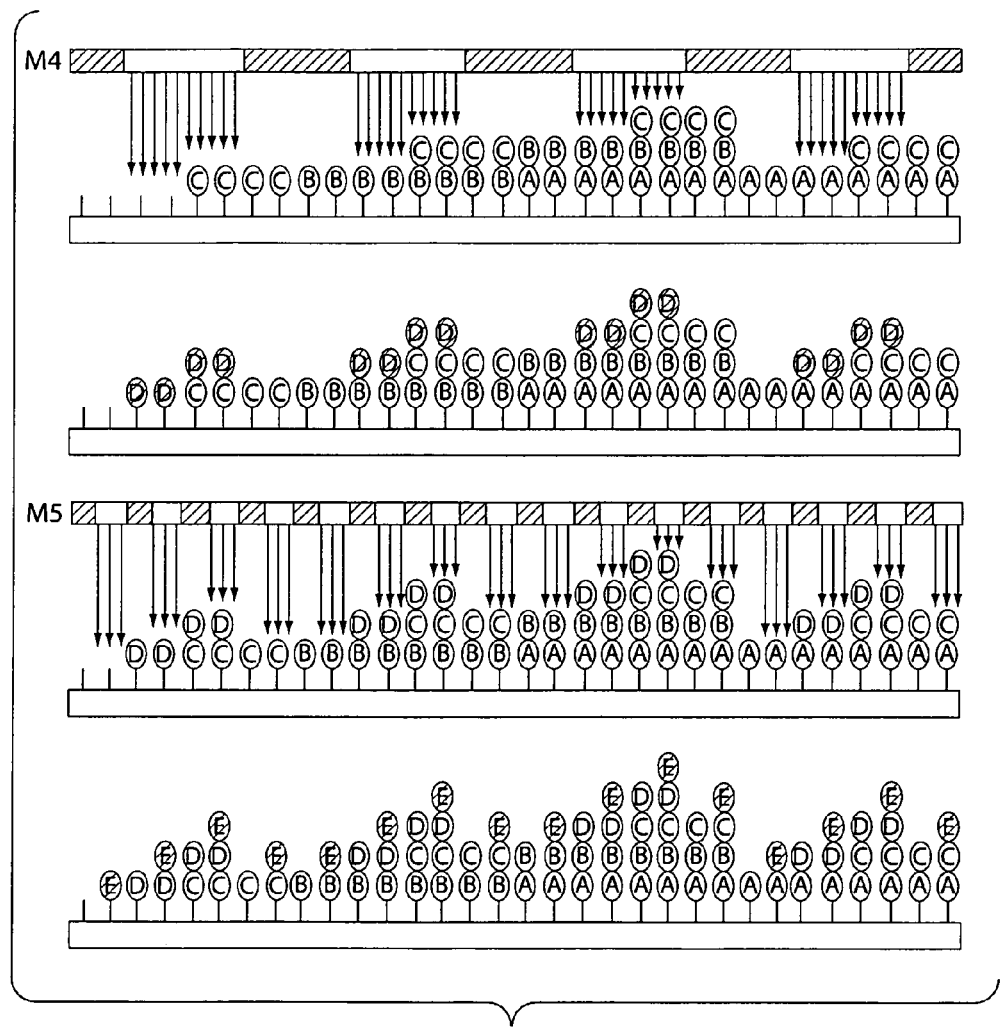

FIGS. 8a & 8b illustrate another binary masking scheme. According to this scheme, referred to herein as a modified gray code masking scheme, the number of masks needed is minimized. For example, the mask m2 could be the same mask as m1 and simply translated laterally. Similarly, the mask m4 could be the same as mask m3 and simply translated laterally.

4. EXAMPLE

Figure 9A:
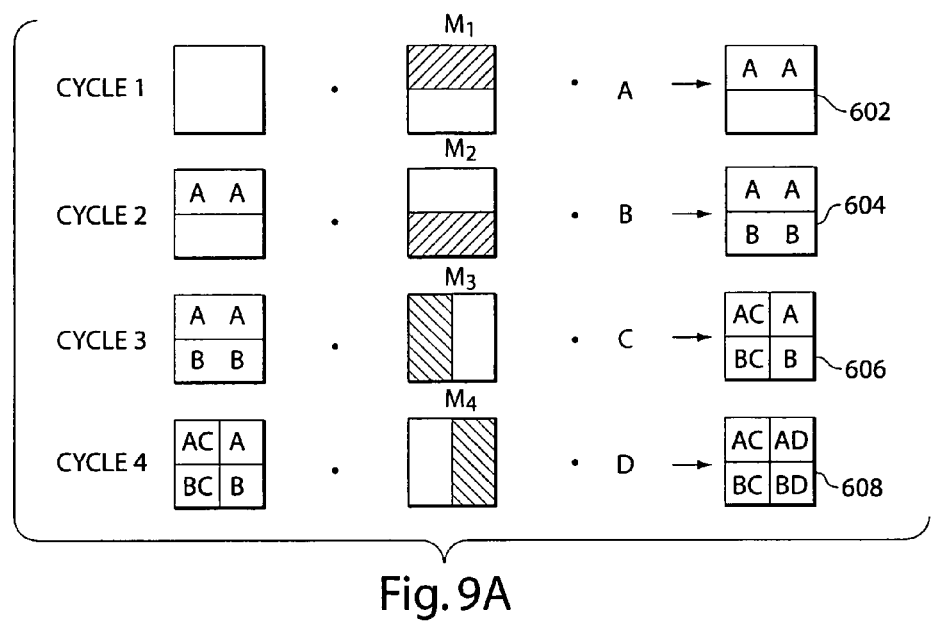
FIG. 9a schematically illustrates a masking scheme for a four step synthesis.

A four-step synthesis is shown in FIG. 9a. The reactants are the ordered set (A,B,C,D). In the first cycle, illumination through $m_1$ activates the upper half of the synthesis area. Building block A is then added to give the distribution 602. Illumination through mask $m_2$ (which activates the lower half), followed by addition of B yields the next intermediate distribution 604. C is added after illumination through $m_3$ (which activates the left half) giving the distribution 604, and D after illumination through $m_4$ (which activates the right half), to yield the final product pattern 608 (AC,AD, BC,BD).

5. EXAMPLE

Figure 9B:
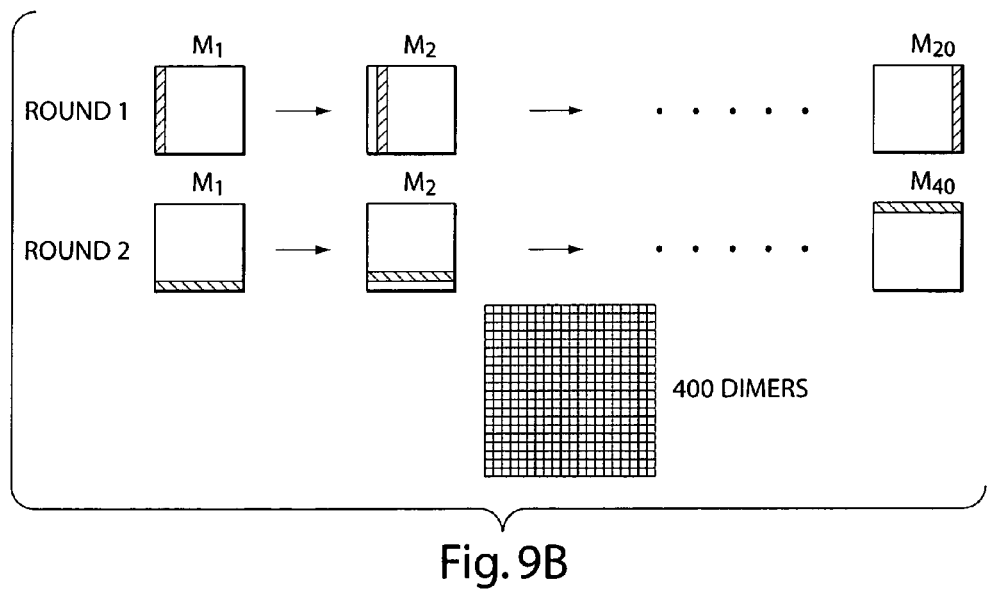
FIG. 9b schematically illustrates synthesis of all 400 peptide dimers.

The above masking strategy for the synthesis may be extended for all 400 dipeptides from the 20 naturally occurring amino acids as shown in FIG. 9b. The synthesis consists of two rounds, with 20 photolysis and chemical coupling cycler per round. In the first cycle of round 1, mask 1 activates 1/20th of the substrate for coupling with the first of 20 amino acids. Nineteen subsequent illumination/coupling cycles in round 1 yield a substrate consisting of 20 rectangular stripes each bearing a distinct member of the 20 amino acids. The masks of round 2 are perpendicular to round 1 masks and therefore a single illumination/coupling cycle in round 2 yields 20 dipeptides. The 20 illumination/coupling cycles of round 2 complete the synthesis of the 400 dipeptides.

6. EXAMPLE

The power of the binary masking strategy can be appreciated by the outcome of a 10-step synthesis that produced 1,024 peptides. The polynomial expression for this 10-step binary synthesis was:

$$(f+\emptyset)(Y+\emptyset)(G+\emptyset)(A+\emptyset)(G+\emptyset)(T+\emptyset)(F+\emptyset)(L+\emptyset)(S+\emptyset)(F+\emptyset)$$

Each peptide occupied a 400×400 µm square. A 32×32 peptide array (1,024 peptides, including the null peptide and 10 peptides of l=1, and a limited number of duplicates) was clearly evident in a fluorescence scan following side group deprotection and treatment with the antibody 3E7 and fluorescinated antibody. Each synthesis site was a 400×400 µm square.

The scan showed a range of fluorescence intensities, from a background value of 3,300 counts to 22,400 counts in the brightest square (x=20, y=9). Only 15 compounds exhibited an intensity greater than 12,300 counts. The median value of the array was 4,800 counts.

Figure 10:
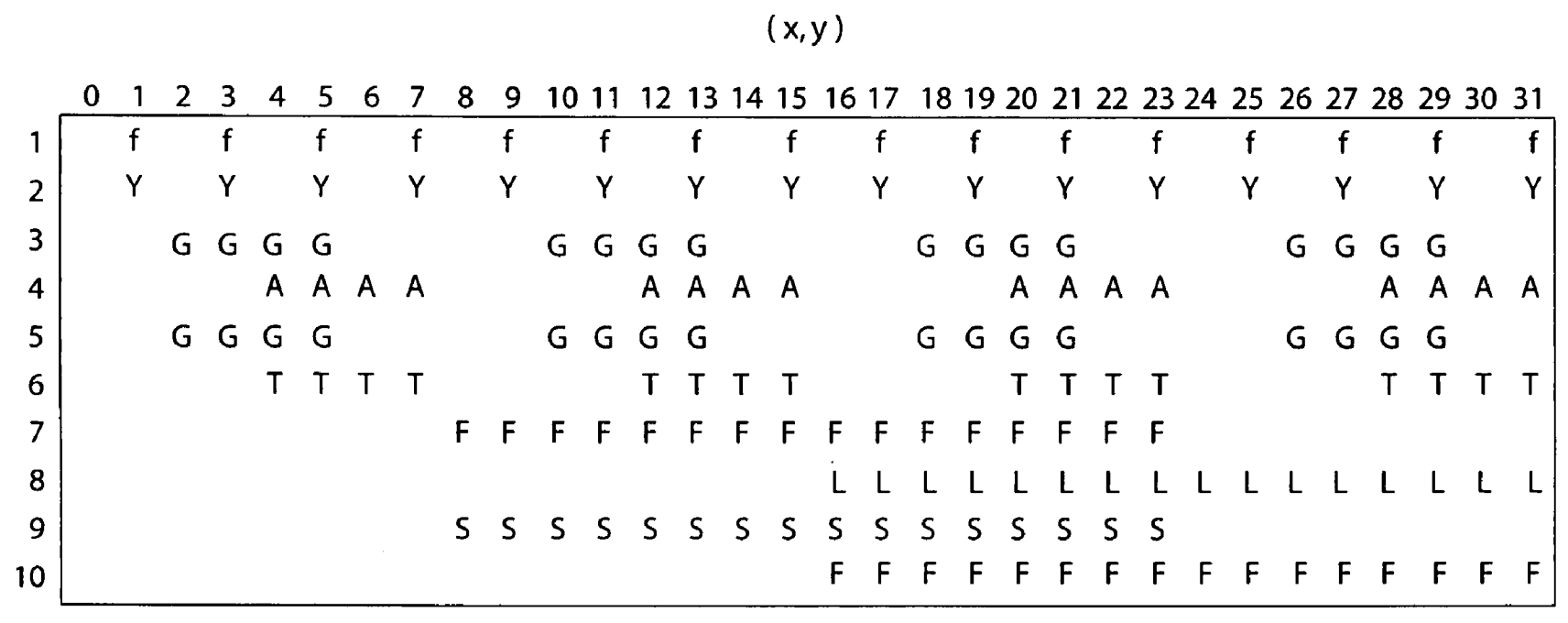

The identity of each peptide in the array could be determined from its x and y coordinate (each range from 0 to 31) and the map of FIG. 10. The chemical units at positions 2, 5, 6, 9, and 10 are specified by the y coordinate and those at positions 1, 3, 4, 7, 8 by the x coordinate. All but one of the peptides was shorter than 10 residues. For example, the peptide at x=12 and y=3 is YGAGF (positions 1, 6, 8, 9, and 10 are nulls). YGAFLS, the brightest element of the array, is at x=20 and y=9.

It is often desirable to deduce a binding affinity of a given peptide from the measured fluorescence intensity. Conceptually, the simplest case is one in which a single peptide binds to a univalent antibody molecule. The fluorescence scan is carried out after the slide is washed with buffer for a defined time. The order of fluorescence intensities is then a measure primarily of the relative dissociation rates of the antibody-peptide complexes. If the on-rate constants are the same (e.g., if they are diffusion-controlled), the order of fluorescence intensities will correspond to the order of binding affinities. However, the situation is sometimes more complex because a bivalent primary antibody and a bivalent secondary antibody are used. The density of peptides in a synthesis area corresponded to a mean separation of ~7 nm, which would allow multivalent antibody-peptide interactions. Hence, fluorescence intensities obtained according to the method herein will often be a qualitative indicator of binding affinity.

Another important consideration is the fidelity of synthesis. Deletions are produced by incomplete photodeprotection or incomplete coupling. The coupling yield per cycle in these experiments is typically between 85% and 95%. Implementing the switch matrix by masking is imperfect because of light diffraction, internal reflection, and scattering. Consequently, stowaways (chemical units that should not be on board) arise by unintended illumination of regions that should be dark. A binary synthesis array contains many of the controls needed to assess the fidelity of a synthesis. For example, the fluorescence signal from a synthesis area nominally containing a tetrapeptide ABCD could come from a tripeptide deletion impurity such as ACD. Such an artifact would be ruled out by the finding that the fluorescence intensity of the ACD site is less than that of the ABCD site.

The fifteen most highly labelled peptides in the array obtained with the synthesis of 1,024 peptides described above, were YGAFLS, YGAFS, YGAFL, YGGFLS, YGAF, YGALS, YGGFS, YGAL, YGAFLF, YGAF, YGAFF, YGGLS, YGGFL, YGAFSF, and YGAFLSF. A striking feature is that all fifteen begin with YG, which agrees with previous work showing that an amino-terminal tyrosine is a key determinant of binding. Residue 3 of this set is either A or G, and residue 4 is either F or L. The exclusion of S and T from these positions is clear cut. The finding that the preferred sequence is YG (A/G) (F/L) fits nicely with the outcome of a study in which a very large library of peptides on phage generated by recombinant DNA methods was screened for binding to antibody 3E7 (see Cwirla et al., Proc. Natl. Acad. Sci. USA, (1990) 87:6378, incorporated herein by reference). Additional binary syntheses based on leads from peptides on phage experiments show that YGA-FMQ, YGAFM, and YGAFQ give stronger fluorescence signals than does YGGFM, the immunogen used to obtain antibody 3E7.

Variations on the above masking strategy will be valuable in certain circumstances. For example, if a "kernel" sequence of interest consists of PQR separated from XYZ and that the aim is to synthesize peptides in which these units are separated by a variable number of different residues. The kernel can be placed in each peptide by using a mask that has 1's everywhere. The polynomial representation of a suitable synthesis is:

$$(P)(Q)(R)(A+\emptyset)(B+\emptyset)(C+\emptyset)(D+\emptyset)(X)(Y)(Z)$$

Sixteen peptides will be formed, ranging in length from the 6-mer PQRXYZ to the 10-mer PQRABCDXYZ.

Several other masking strategies will also find value in selected circumstances. By using a particular mask more than once, two or more reactants will appear in the same set of products. For example, suppose that the mask for an 8-step synthesis is A 11110000
B 00001111
C 11001100
D 00110011
E 10101010
F 01010101
G 11110000
H 00001111

The products are ACEG, ACFG, ADEG, ADFG, BCEH, BCFH, BDEH, and BDFH. A and G always appear together because their additions were directed by the same mask, and likewise for B and H.

C. Linker Selection

According to preferred embodiments the linker molecules used as an intermediary between the synthesized polymers and the substrate are selected for optimum length and/or type for improved binding interaction with a receptor.

According to this aspect of the invention diverse linkers of varying length and/or type are synthesized for subsequent attachment of a ligand. Through variations in the length and type of linker, it becomes possible to optimize the binding interaction between an immobilized ligand and its receptor.

The degree of binding between a ligand (peptide, inhibitor, hapten, drug, etc.) and its receptor (enzyme, antibody, etc.) when one of the partners is immobilized on to a substrate will in some embodiments depend on the accessibility of the receptor in solution to the immobilized ligand. The accessibility in turn will depend on the length and/or type of linker molecule employed to immobilize one of the partners. Preferred embodiments of the invention therefore employ the VLSIPS technology described herein to generate an array of, preferably, inactive or inert linkers of varying length and/or type, using photochemical protecting groups to selectively expose different regions of the substrate and to build upon chemically-active groups.

In the simplest embodiment of this concept, the same unit is attached to the substrate in varying multiples or lengths in known locations on the substrate via VLSIPS techniques to generate an array of polymers of varying length. A single ligand (peptide, drug, hapten, etc.) is attached to each of them, and an assay is performed with the binding site to evaluate the degree of binding with a receptor that is known to bind to the ligand. In cases where the linker length impacts the ability of the receptor to bind to the ligand, varying levels of binding will be observed. In general, the linker which provides the highest binding will then be used to assay other ligands synthesized in accordance with the techniques herein.

According to other embodiments the binding between a single ligand/receptor pair is evaluated for linkers of diverse monomer sequence. According to these embodiments, the linkers are synthesized in an array in accordance with the techniques herein and have different monomer sequence (and, optionally, different lengths). Thereafter, all of the linker molecules are provided with a ligand known to have at least some binding affinity for a given receptor. The given receptor is then exposed to the ligand and binding affinity is deduced. Linker molecules which provide adequate binding between the ligand and receptor are then utilized in screening studies.

D. Protecting Groups

As discussed above, selectively removable protecting groups allow creation of well defined areas of substrate surface having differing reactivities. Preferably, the protecting groups are selectively removed from the surface by applying a specific activator, such as electromagnetic radiation of a specific wavelength and intensity. More preferably, the specific activator exposes selected areas of surface to remove the protecting groups in the exposed areas.

Protecting groups of the present invention are used in conjunction with solid phase oligomer syntheses, such as peptide syntheses using natural or unnatural amino acids, nucleotide syntheses using deoxyribonucleic and ribonucleic acids, oligosaccharide syntheses, and the like. In addition to protecting the substrate surface from unwanted reaction, the protecting groups block a reactive end of the monomer to prevent self-polymerization. For instance, attachment of a protecting group to the amino terminus of an activated amino acid, such as an N-hydroxysuccinimide-activated ester of the amino acid, prevents the amino terminus of one monomer from reacting with the activated ester portion of another during peptide synthesis. Alternatively, the protecting group may be attached to the carboxyl group of an amino acid to prevent reaction at this site. Most protecting groups can be attached to either the amino or the carboxyl group of an amino acid, and the nature of the chemical synthesis will dictate which reactive group will require a protecting group. Analogously, attachment of a protecting group to the 5'-hydroxyl group of a nucleoside during synthesis using for example, phosphate-triester coupling chemistry, prevents the 5'-hydroxyl of one nucleoside from reacting with the 3'-activated phosphate-triester of another. Attachment of a photoremovable protecting group to a hydroxyl group of a nucleoside can occur before attachment of an activated phosphorous group to a hydroxyl group.

Regardless of the specific use, protecting groups are employed to protect a moiety on a molecule from reacting with another reagent. Protecting groups of the present invention have the following characteristics: they prevent selected reagents from modifying the group to which they are attached; they are stable (that is, they remain attached to the molecule) to the synthesis reaction conditions; they are removable under conditions that do not adversely affect the remaining structure; and once removed, do not react appreciably with the surface or surface-bound oligomer. The selection of a suitable protecting group will depend, of course, on the chemical nature of the monomer unit and oligomer, as well as the specific reagents they are to protect against.

In a preferred embodiment, the protecting groups are photoactivatable. The properties and uses of photoreactive protecting compounds have been reviewed. See, McCray et al., *Ann. Rev. of Biophys. and Biophys. Chem.* (1989) 18:239–270, which is incorporated herein by reference. Preferably, the photosensitive protecting groups will be removable by radiation in the ultraviolet (UV) or visible portion of the electromagnetic spectrum. More preferably, the protecting groups will be removable by radiation in the near UV or visible portion of the spectrum. In some embodiments, however, activation may be performed by other methods such as localized heating, electron beam lithography, laser pumping, oxidation or reduction with microelectrodes, and the like. Sulfonyl compounds are suitable reactive groups for electron beam lithography. Oxidative or reductive removal is accomplished by exposure of the protecting group to an electric current source, preferably using microelectrodes directed to the predefined regions of the surface which are desired for activation. Other methods may be used in light of this disclosure.

Many, although not all, of the photoremovable protecting groups will be aromatic compounds that absorb near-UV and visible radiation. Suitable photoremovable protecting groups are described in, for example, McCray et al., Patchornik, *J. Amer. Chem. Soc.* (1970) 92:6333, and Amit et al., *J. Org. Chem.* (1974) 39:192, which are incorporated herein by reference.

A preferred class of photoremovable protecting groups has the general formula:

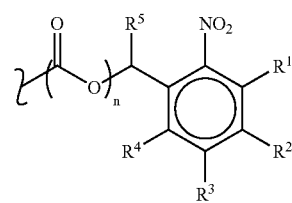

where $R^1$, $R^2$, $R^3$, and $R^4$ independently are a hydrogen atom, a lower alkyl, aryl, benzyl, halogen, hydroxyl, alkoxyl, thiol, thioether, amino, nitro, carboxyl, formate, formamido or phosphido group, or adjacent substituents (i.e., $R^1$–$R^2$, $R^2$–$R^3$, $R^3$—$R^4$) are substituted oxygen groups that together form a cyclic acetal or ketal; $R^5$ is a hydrogen atom, a alkoxyl, alkyl, hydrogen, halo, aryl, or alkenyl group, and n=0 or 1.

A preferred protecting group, 6-nitroveratryl (NV), which is used for protecting the carboxyl terminus of an amino acid or the hydroxyl group of a nucleotide, for example, is formed when $R^2$ and $R^3$ are each a methoxy group, $R^1$, $R^4$ and $R^5$ are each a hydrogen atom, and n=0:

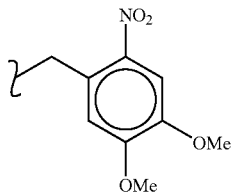

A preferred protecting group, 6-nitroveratryloxycarbonyl (NVOC), which is used to protect the amino terminus of an amino acid, for example, is formed when $R^2$ and $R^3$ are each a methoxy group, $R^1$, $R^4$ and $R^5$ are each a hydrogen atom, and n=1:

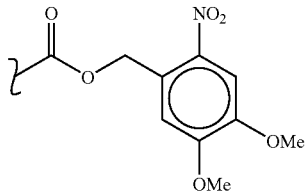

Another preferred protecting group, 6-nitropiperonyl (NP), which is used for protecting the carboxyl terminus of an amino acid or the hydroxyl group of a nucleotide, for example, is formed when $R^2$ and $R^3$ together form a methylene acetal, $R^1$, $R^4$ and $R^5$ are each a hydrogen atom, and n=0:

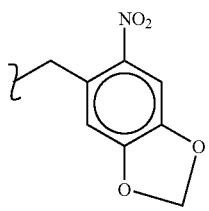

Another preferred protecting group, 6-nitropiperonyloxycarbonyl (NPOC), which is used to protect the amino terminus of an amino acid, for example, is formed when $R^2$ and $R^3$ together form a methylene acetal, $R^1$, $R^4$ and $R^5$ are each a hydrogen atom, and n =1:

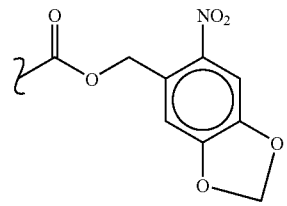

A most preferred protecting group, methyl-6-nitroveratryl (MeNV), which is used for protecting the carboxyl terminus of an amino acid or the hydroxyl group of a nucleotide, for example, is formed when $R^2$ and $R^3$ are each a methoxy group, $R^1$ and $R^4$ are each a hydrogen atom, $R^5$ is a methyl group, and n=0:

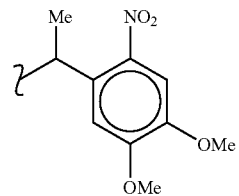

Another most preferred protecting group, methyl-6-nitroveratryloxycarbonyl (MeNVOC), which is used to protect the amino terminus of an amino acid, for example, is formed when $R^2$ and $R^3$ are each a methoxy group, $R^1$ and $R^4$ are each a hydrogen atom, $R^5$ is a methyl group, and n=1:

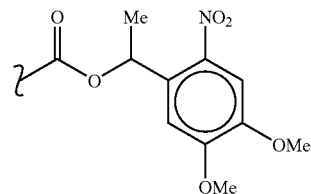

Another most preferred protecting group, methyl-6-nitropiperonyl (MeNP), which is used for protecting the carboxyl terminus of an amino acid or the hydroxyl group of a nucleotide, for example, is formed when $R^2$ and $R^3$ together form a methylene acetal, $R^1$ and $R^4$ are each a hydrogen atom, $R^5$ is a methyl group, and n=0:

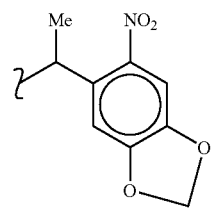

Another most preferred protecting group, methyl-6-nitropiperonyloxycarbonyl (MeNPOC), which is used to protect the amino terminus of an amino acid, for example, is formed when $R^2$ and $R^3$ together form a methylene acetal, $R^1$ and R⁴ are each a hydrogen atom, R⁵ is a methyl group, and n=1:

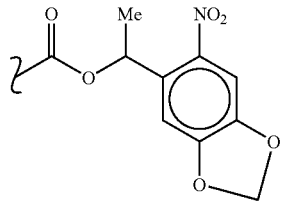

A protected amino acid having a photoactivatable oxycarbonyl protecting group, such NVOC or NPOC or their corresponding methyl derivatives, MeNVOC or MeNPOC, respectively, on the amino terminus is formed by acylating the amine of the amino acid with an activated oxycarbonyl ester of the protecting group. Examples of activated oxycarbonyl esters of NVOC and MeNVOC have the general formula:

NVOC-X

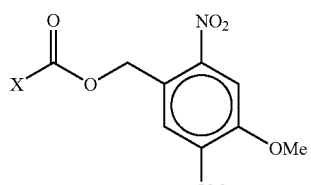

MeNVOC-X

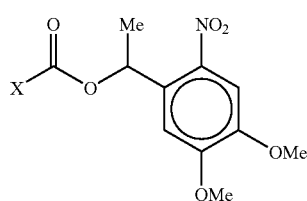

where X is halogen, mixed anhydride, phenoxy, p-nitrophenoxy, N-hydroxysuccinimide, and the like.

A protected amino acid or nucleotide having a photoactivatable protecting group, such as NV or NP or their corresponding methyl derivatives, MeNV or MeNP, respectively, on the carboxy terminus of the amino acid or 5'-hydroxy terminus of the nucleotide, is formed by acylating the carboxy terminus or 5'-OH with an activated benzyl derivative of the protecting group. Examples of activated benzyl derivatives of MeNV and MeNP have the general formula:

MeNV-X

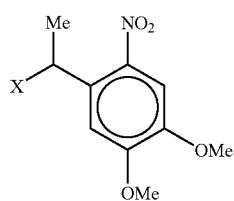

-continued

MeNP-X

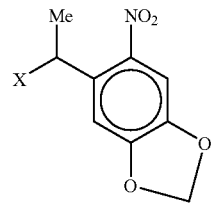

where X is halogen, hydroxyl, tosyl, mesyl, trifluormethyl, diazo, azido, and the like.

Another method for generating protected monomers is to react the benzylic alcohol derivative of the protecting group with an activated ester of the monomer. For example, to protect the carboxyl terminus of an amino acid, an activated ester of the amino acid is reacted with the alcohol derivative of the protecting group, such as 6-nitroveratrol (NVOH). Examples of activated esters suitable for such uses include halo-formate, mixed anhydride, imidazoyl formate, acyl halide, and also includes formation of the activated ester in situ the use of common reagents such as DCC and the like. See Atherton et al. for other examples of activated esters.

A further method for generating protected monomers is to react the benzylic alcohol derivative of the protecting group with an activated carbon of the monomer. For example, to protect the 5'-hydroxyl group of a nucleic acid, a derivative having a 5'-activated carbon is reacted with the alcohol derivative of the protecting group, such as methyl-6-nitropiperonol (MePyROH). Examples of nucleotides having activating groups attached to the 5'-hydroxyl group have the general formula:

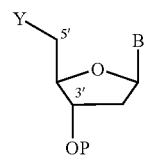

where Y is a halogen atom, a tosyl, mesyl, trifluoromethyl, azido, or diazo group, and the like.

Another class of preferred photochemical protecting groups has the formula:

$$\text{[structure with } R^1, R^2, R^3, R^4, R^5, n \text{]}$$

where $R^1$, $R^2$, and $R^3$ independently are a hydrogen atom, a lower alkyl, aryl, benzyl, halogen, hydroxyl, alkoxyl, thiol, thioether, amino, nitro, carboxyl, formate, formamido, sulfanates, sulfido or phosphido group, $R^4$ and $R^5$ independently are a hydrogen atom, an alkoxy, alkyl, halo, aryl, hydrogen, or alkenyl group, and n=0 or 1.

A preferred protecting group, 1-pyrenylmethyloxycarbonyl (PyROC), which is used to protect the amino terminus of an amino acid, for example, is formed when $R^1$ through $R^5$ are each a hydrogen atom and n=1:

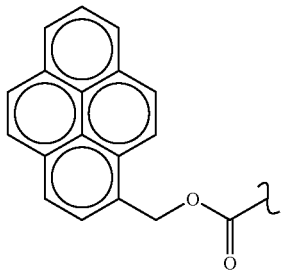

Another preferred protecting group, 1-pyrenylmethyl (PyR), which is used for protecting the carboxy terminus of an amino acid or the hydroxyl group of a nucleotide, for example, is formed when $R^1$ through $R^5$ are each a hydrogen atom and n=0:

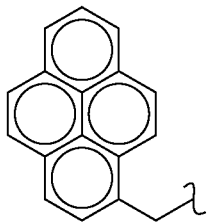

An amino acid having a pyrenylmethyloxycarbonyl protecting group on its amino terminus is formed by acylation of the free amine of amino acid with an activated oxycarbonyl ester of the pyrenyl protecting group. Examples of activated oxycarbonyl esters of PyROC have the general formula:

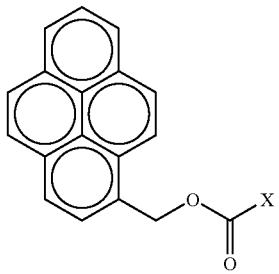

where X is halogen, or mixed anhydride, p-nitrophenoxy, or N-hydroxysuccinimide group, and the like.

A protected amino acid or nucleotide having a photoactivatable protecting group, such as PyR, on the carboxy terminus of the amino acid or 5'-hydroxy terminus of the nucleic acid, respectively, is formed by acylating the carboxy terminus or 5'-OH with an activated pyrenylmethyl derivative of the protecting group. Examples of activated pyrenylmethyl derivatives of PyR have the general formula:

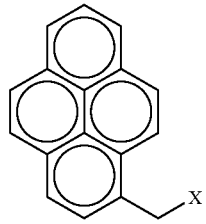

where X is a halogen atom, a hydroxyl, diazo, -or azido group, and the like.

Another method of generating protected monomers is to react the pyrenylmethyl alcohol moiety of the protecting group with an activated ester of the monomer. For example, an activated ester of an amino acid can be reacted with the alcohol derivative of the protecting group, such as pyrenylmethyl alcohol (PyROH), to form the protected derivative of the carboxy terminus of the amino acid. Examples of activated esters include halo-formate, mixed anhydride, imidazoyl formate, acyl halide, and also includes formation of the activated ester in situ and the use of common reagents such as DCC and the like.

Clearly, many photosensitive protecting groups are suitable for use in the present invention. In preferred embodiments, the substrate is irradiated to remove the photoremovable protecting groups and create regions having free reactive moieties and side products resulting from the protecting group. The removal rate of the protecting groups depends on the wavelength and intensity of the incident radiation, as well as the physical and chemical properties of the protecting group itself. Preferred protecting groups are removed at a faster rate and with a lower intensity of radiation. For example, at a given set of conditions, MeNVOC and MeNPOC are photolytically removed from the N-terminus of a peptide chain faster than their unsubstituted parent compounds, NVOC and NPOC, respectively.

Removal of the protecting.group is accomplished by irradiation to liberate the reactive group and degradation products derived from the protecting group. Not wishing to be bound by theory, it is believed that irradiation of an NVOC- and MeNVOC-protected oligomers occurs by the following reaction schemes:

NVOC-AA-→3,4-dimethoxy-6-nitrosobenzaldehyde+ $CO_2$+AA

MeNVOC-AA-→3,4-dimethoxy-6-nitrosoacetophenone+ $CO_2$+AA where AA represents the N-terminus of the amino acid oligomer.

Along with the unprotected amino acid, other products are liberated into solution: carbon dioxide and a 2,3-dimethoxy-6-nitrosophenylcarbonyl compound, which can react with nucleophilic portions of the oligomer to form unwanted secondary reactions. In the case of an NVOC-protected amino acid, the degradation product is a nitrosobenzaldehyde, while the degradation product for the other is a nitrosophenyl ketone. For instance, it is believed that the product aldehyde from NVOC degradation reacts with free amines to form a Schiff base (imine) that affects the remaining polymer synthesis. Preferred photoremovable protecting groups react slowly or reversibly with the oligomer on the support.

Again not wishing to be bound by theory, it is believed that the product ketone from irradiation of a MeNVOC-protected oligomer reacts at a slower rate with nucleophiles on the oligomer than the product aldehyde from irradiation of the same NVOC-protected oligomer. Although not unambiguously determined, it is believed that this difference in reaction rate is due to the difference in general reactivity between aldehyde and ketones towards nucleophiles due to steric and electronic effects.

The photoremovable protecting groups of the present invention are readily removed. For example, the photolysis of N-protected L-phenylalanine in solution and having different photoremovable protecting groups was analyzed, and the results are presented in the following table:

TABLE

Photolysis of Protected L-Phe-OH

| Solvent | $t_{1/2}$ in seconds | | | |
| --- | --- | --- | --- | --- |
|  | NBOC | NVOC | MeNVOC | MeNPOC |
| Dioxane | 1288 | 110 | 24 | 19 |
| 5mM $H_2SO_4$/Dioxane | 1575 | 98 | 33 | 22 |

The half life, $t_e$ 50% of the starting amount of protecting group. NBOC is the 6-nitrobenzyloxycarbonyl group, NVOC is the 6-nitroveratryloxycarbonyl group, MeNVOC is the methyl-6-nitroveratryloxycarbonyl group, and MeNPOC is the methyl-6-nitropiperonyloxycarbonyl group. The photolysis was carried out in the indicated solvent with 362/364 nm-wavelength irradiation having an intensity of 10 mW/cm$^2$, and the concentration of each protected phenylalanine was 0.10 mM.

The table shows that deprotection of NVOC—, MeNVOC—, and MeNPOC-protected phenylalanine proceeded faster than the deprotection of NBOC. Furthermore, it shows that the deprotection of the two derivatives that are substituted on the benzylic carbon, MeNVOC and MeNPOC, were photolyzed at the highest rates in both dioxane and acidified dioxane.

1. Use of Photoremovable Groups During Solid-Phase Synthesis of Peptides

The formation of peptides on a solid-phase support requires the stepwise attachment of an amino acid to a substrate-bound growing chain. In order to prevent unwanted polymerization of the monomeric amino acid under the reaction conditions, protection of the amino terminus of the amino acid is required. After the monomer is coupled to the end of the peptide, the N-terminal protecting group is removed, and another amino acid is coupled to the chain. This cycle of coupling and deprotecting is continued for each amino acid in the peptide sequence. See Merrifield, *J. Am. Chem. Soc.* (1963) 85:2149, and Atherton et al., "Solid Phase Peptide Synthesis" 1989, IRL Press, London, both incorporated herein by reference for all purposes. As described above, the use of a photoremovable protecting group allows removal of selected portions of the substrate surface, via patterned irradiation, during the deprotection cycle of the solid phase synthesis. This selectively allows spatial control of the synthesis—the next amino acid is coupled only to the irradiated areas.

In one embodiment, the photoremovable protecting groups of the present invention are attached to an activated ester of an amino acid at the amino terminus:

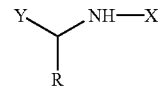

where R is the side chain of a natural or unnatural amino acid, X is a photoremovable protecting group, and Y is an activated carboxylic acid derivative. The photoremovable protecting group, X, is preferably NVOC, NPOC, PyROC, MeNVOC, MeNPOC, and the like as discussed above. The activated ester, Y, is preferably a reactive derivative having a high coupling efficiency, such as an acyl halide, mixed anhydride, N-hydroxysuccinimide ester, perfluorophenyl ester, or urethane protected acid, and the like. Other activated esters and reaction conditions are well known (See Atherton et al.).

2. Use of Photoremovable Groups During Solid-Phase Synthesis of Oligonucleotides The formation of oligonucleotides on a solid-phase support requires the stepwise attachment of a nucleotide to a substrate-bound growing oligomer. In order to prevent unwanted polymerization of the monomeric nucleotide under the reaction conditions, protection of the 5'-hydroxyl group of the nucleotide is required. After the monomer is coupled to the end of the oligomer, the 5'-hydroxyl protecting group is removed, and another nucleotide is coupled to the chain. This cycle of coupling and deprotecting is continued for each nucleotide in the oligomer sequence. See Gait, "Oligonucleotide Synthesis: A Practical Approach" 1984, IRL Press, London, incorporated herein by reference for all purposes. As described above, the use of a photoremovable protecting group allows removal, via patterned irradiation, of selected portions of the substrate surface during the deprotection cycle of the solid phase synthesis. This selectively allows spatial control of the synthesis—the next nucleotide is coupled only to the irradiated areas.

Oligonucleotide synthesis generally involves coupling an activated phosphorous derivative on the 3'-hydroxyl group of a nucleotide with the 5'-hydroxyl group of an oligomer bound to a solid support. Two major chemical methods exist to perform this coupling: the phosphate-triester and phosphoamidite methods (See Gait) Protecting groups of the present invention are suitable for use in either method.

In a preferred embodiment, a photoremovable protecting group is attached to an activated nucleotide on the 5'-hydroxyl group:

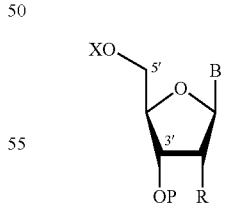

where B is the base attached to the sugar ring; R is a hydrogen atom when the sugar is deoxyribose or R is a hydroxyl group when the sugar is ribose; P represents an activated phosphorous group; and X is a photoremovable protecting group. The photoremovable protecting group, X, is preferably NV, NP, PyR, MeNV, MeNP, and the like as described above. The activated phosphorous group, P, is preferably a reactive derivative having a high coupling efficiency, such as a phosphate-triester, phosphoamidite (e.g., N,N-dialkyl-O-methylphosphoramidite, N,N-dialkyl-O-(2-cyanoethyl)phosphoramidite) or the like. Other activated phosphorous derivatives, as well as reaction conditions, are well known (See Gait).

E. Amino Acid N-Carboxy Anhydrides Protected With a Photoremovable Group

During Merrifield peptide synthesis, an activated ester of one amino acid is coupled with the free amino terminus of a substrate-bound oligomer. Activated esters of amino acids suitable for the solid phase synthesis include halo-formate, mixed anhydride, imidazoyl formate, acyl halide, and also includes formation of the activated ester in situ and the use of common reagents such as DCC and the like (See Atherton et al.). A preferred protected and activated amino acid has the general formula:

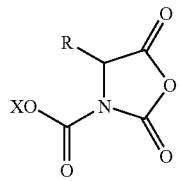

where R is the side chain of the amino acid and X is a photoremovable protecting group. This compound is a urethane-protected amino acid having a photoremovable protecting group attach to the amine. A more preferred activated amino acid is formed when the photoremovable protecting group has the general formula:

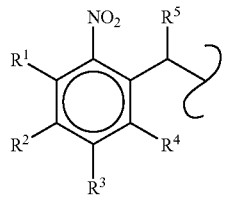

where $R^1$, $R^2$, $R^3$, and $R^4$ independently are a hydrogen atom, a lower alkyl, aryl, benzyl, halogen, hydroxyl, alkoxyl, thiol, thioether, amino, nitro, carboxyl, formate, formamido or phosphido group, or adjacent substituents (i.e., $R^1$–$R^2$, $R^2$–$R^3$, $R^3$–$R^4$) are substituted oxygen groups that together form a cyclic acetal or ketal; and $R^5$ is a hydrogen atom, a alkoxyl, alkyl, hydrogen, halo, aryl, or alkenyl group.

A preferred activated amino acid is formed when the photoremovable protecting group is 6-nitroveratryloxycarbonyl. That is, $R^1$ and $R^4$ are each a hydrogen atom, $R^2$ and $R^3$ are each a methoxy group, and $R^5$ is a hydrogen atom. Another preferred activated amino acid is formed when the photoremovable group is 6-nitropiperonyl: $R^1$ and $R^4$ are each a hydrogen atom, $R^2$ and $R^3$ together form a methylene acetal, and $R^5$ is a hydrogen atom. Other protecting groups are possible. Another preferred activated ester is formed when the photoremovable group is methyl-6-nitroveratryl or methyl-6-nitropiperonyl.

Another preferred activated amino acid is formed when the photoremovable protecting group has the general formula:

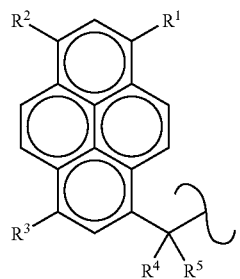

where $R^1$, $R^2$, and $R^3$ independently are a hydrogen atom, a lower alkyl, aryl, benzyl, halogen, hydroxyl, alkoxyl, thiol, thioether, amino, nitro, carboxyl, formate, formamido, sulfanates, sulfido or phosphido group, and $R^4$ and $R^5$ independently are a hydrogen atom, an alkoxy, alkyl, halo, aryl, hydrogen, or alkenyl group. The resulting compound is a urethane-protected amino acid having a pyrenylmethyloxycarbonyl protecting group attached to the amine. A more preferred embodiment is formed when $R^1$ through $R^5$ are each a hydrogen atom.

The urethane-protected amino acids having a photoremovable protecting group of the present invention are prepared by condensation of an N-protected amino acid with an acylating agent such as an acyl halide, anhydride, chloroformate and the like (See Fuller et al., U.S. Pat. No. 4,946,942 and Fuller et al., J. Amer. Chem. Soc. (1990) 112:7414–7416, both herein incorporated by reference for all purposes).

Urethane-protected amino acids having photoremovable protecting groups are generally useful as reagents during solid-phase peptide synthesis, and because of the spatially selectivity possible with the photoremovable protecting group, are especially useful for the spatially addressing peptide synthesis. These amino acids are difunctional: the urethane group first serves to activate the carboxy terminus for reaction with the amine bound to the surface and, once the peptide bond is formed, the photoremovable protecting group protects the newly formed amino terminus from further reaction. These amino acids are also highly reactive to nucledphiles, such as deprotected amines on the surface of the solid support, and due to this high reactivity, the solid-phase peptide coupling times are significantly reduced, and yields are typically higher.

IV. Data Collection

A. Data Collection System

Figure 11:
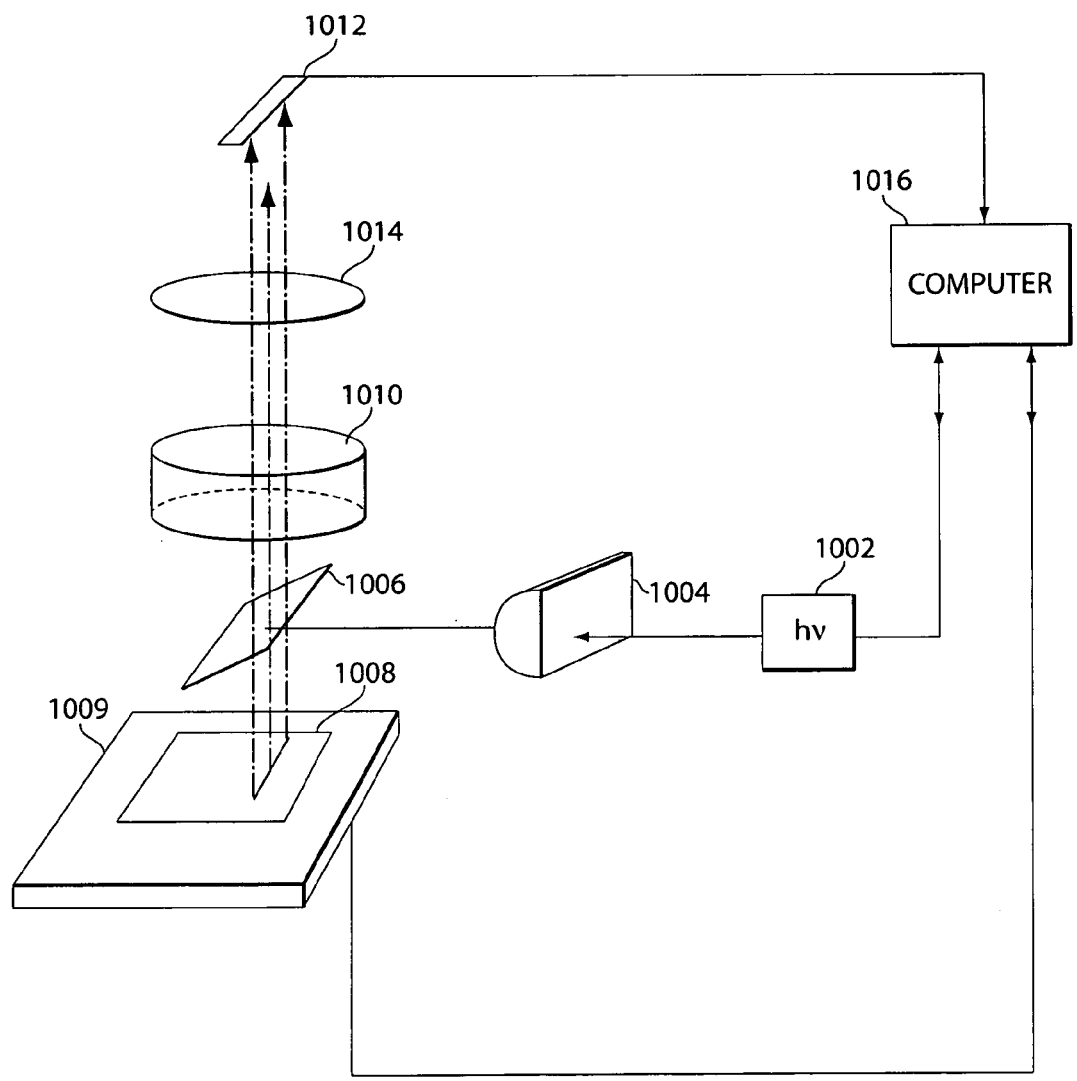
FIG. 11 schematically illustrates a data collection system.

Substrates prepared in accordance with the above description are used in one embodiment to determine which of the plurality of sequences thereon bind to a receptor of interest. FIG. 11 illustrates one embodiment of a device used to detect regions of a substrate which contain florescent markers. This device would be used, for example, to detect the presence or absence of a labeled receptor such as an antibody which has bound to a synthesized polymer on a substrate.

Light is directed at the substrate from a light source 1002 such as a laser light source of the type well known to those of skill in the art such as a model no. 2025 made by Spectra Physics. Light from the source is directed at a lens 1004 which is preferably a cylindrical lens of the type well known to those of skill in the art. The resulting output from the lens 1004 is a linear beam rather than a spot of light, resulting in the capability to detect data substantially simultaneously along a linear array of pixels rather than on a pixel-by-pixel basis. It will be understood that which a cylindrical lens is used herein as an illustration of one technique for generating a linear beam of light on a surface, it will be understood that other techniques could also be utilized.

The beam from the cylindrical lens is passed through a dichroic mirror or prism and directed at the surface of the suitably prepared substrate 1008. Substrate 1008 is placed on an x-y translation stage 1009 such as a model no. PM500-8 made by Newport. Light at certain locations on the substrate will be fluoresced and transmitted along the path indicated by dashed lines back through the dichroic mirror, and focused with a suitable lens 1010 such as an f/1.4 camera lens on a linear detector 1012 via a variable f stop focusing lens 1014. Through use of a linear light beam, it becomes possible to generate data over a line of pixels (such as about 1 cm) along the substrate, rather than from individual points on the substrate. In alternative embodiments, light is directed at a 2-dimensional area of the substrate and fluoresced light detected by a 2-dimensional CCD array. Linear detection is preferred because substantially higher power densities are obtained.

Detector 1012 detects the amount of light fluoresced from the substrate as a function of position. According to one embodiment the detector is a linear CCD array of the type commonly known to those of skill in the art. The x-y translation stage, the light source, and the detector 1012 are all operably connected to a computer 1016 such as a IBM PC-AT or equivalent for control of the device and data collection from the CCD array.

In operation, the substrate is appropriately positioned by the translation stage. The light source is then illuminated, and intensity data are gathered with the computer via the detector.

Figure 12:
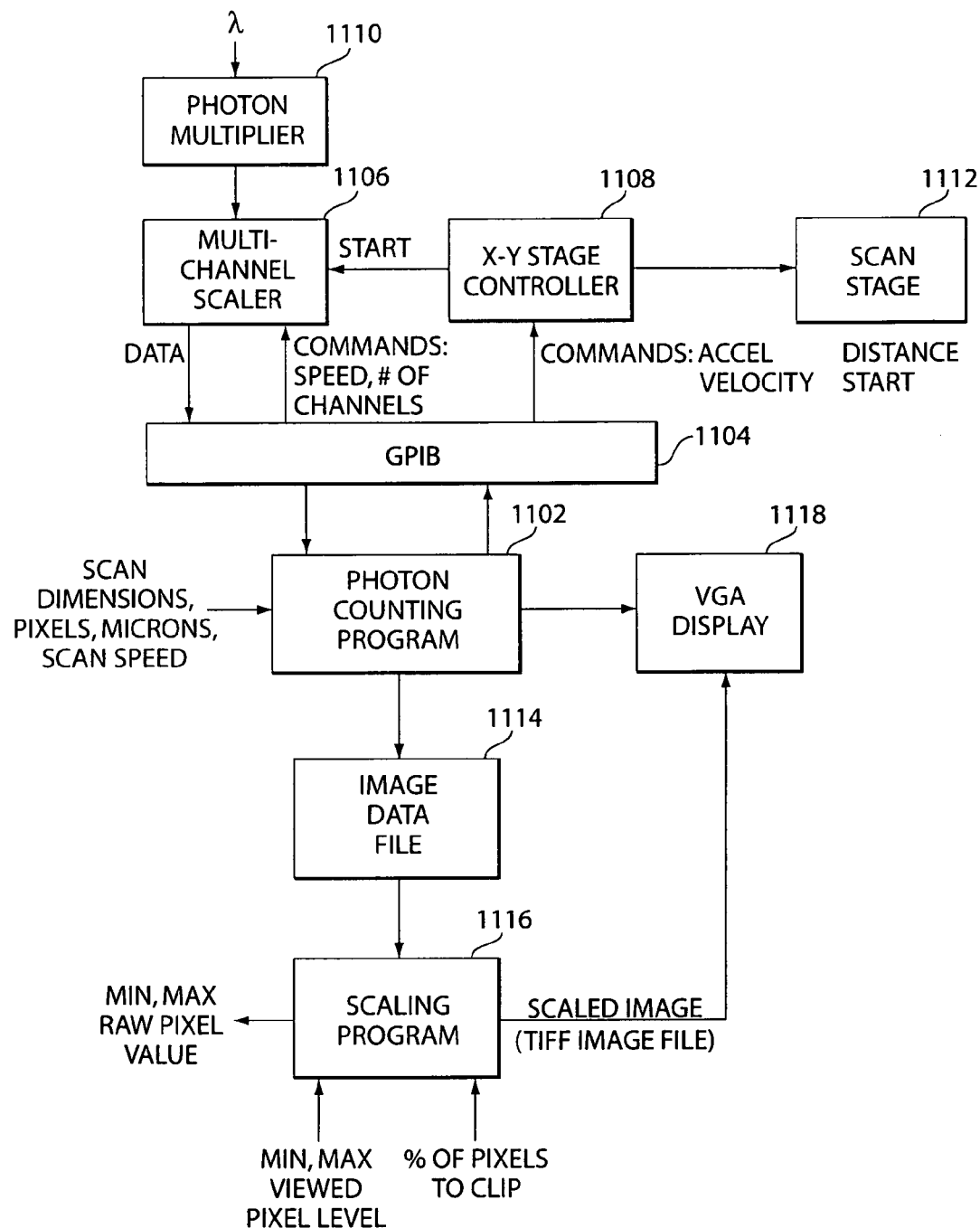
FIG. 12 is a block diagram illustrating the architecture of the data collection system.

FIG. 12 illustrates the architecture of the data collection system in greater detail. Operation of the system occurs under the direction of the photon counting program 1102 (photon), included herewith as Appendix B. The user inputs the scan dimensions, the number of pixels or data points in a region, and the scan speed to the counting program. Via a GP1B bus 1104 the program (in an IBM PC compatible computer, for example) interfaces with a multichannel scaler 1106 such as a Stanford Research SR 430 and an x-y stage controller 1108 such as a PM500. The signal from the light from the fluorescing substrate enters a photon counter 1110, providing output to the scaler 1106. Data are output from the scaler indicative of the number of counts in a given region. After scanning a selected area, the stage controller is activated with commands for acceleration and velocity, which in turn drives the scan stage 1112 such as a PM500-A to another region.

Data are collected in an image data file 1114 and processed in a scaling program 1116, also included in Appendix B. A scaled image is output for display on, for example, a VGA display 1118. The image is scaled based on an input of the percentage of pixels to clip and the minimum and maximum pixel levels to be viewed. The system outputs for use the min and max pixel levels in the raw data.

B. Data Analysis

The output from the data collection system is an array of data indicative of fluorescent intensity versus location on the substrate. The data are typically taken over regions substantially smaller than the area in which synthesis of a given polymer has taken place. Merely by way of example, if polymers were synthesized in squares on the substrate having dimensions of 500 microns by 500 microns, the data may be taken over regions having dimensions of 5 microns by 5 microns. In most preferred embodiments, the regions over which florescence data are taken across the substrate are less than about ½ the area of the regions in which individual polymers are synthesized, preferably less than 1/10 the area in which a single polymer is synthesized, and most preferably less than 1/100 the area in which a single polymer is synthesized. Hence, within any area in which a given polymer has been synthesized, a large number of fluorescence data points are collected.

A plot of number of pixels versus intensity for a scan of a cell when it has been exposed to, for example, a labeled antibody will typically take the form of a bell curve, but spurious data are observed, particularly at higher intensities. Since it is desirable to use an average of fluorescent intensity over a given synthesis region in determining relative binding affinity, these spurious data will tend to undesirably skew the data.

Accordingly, in one embodiment of the invention the data are corrected for removal of these spurious data points, and an average of the data points is thereafter utilized in determining relative binding efficiency.

Figure 13:
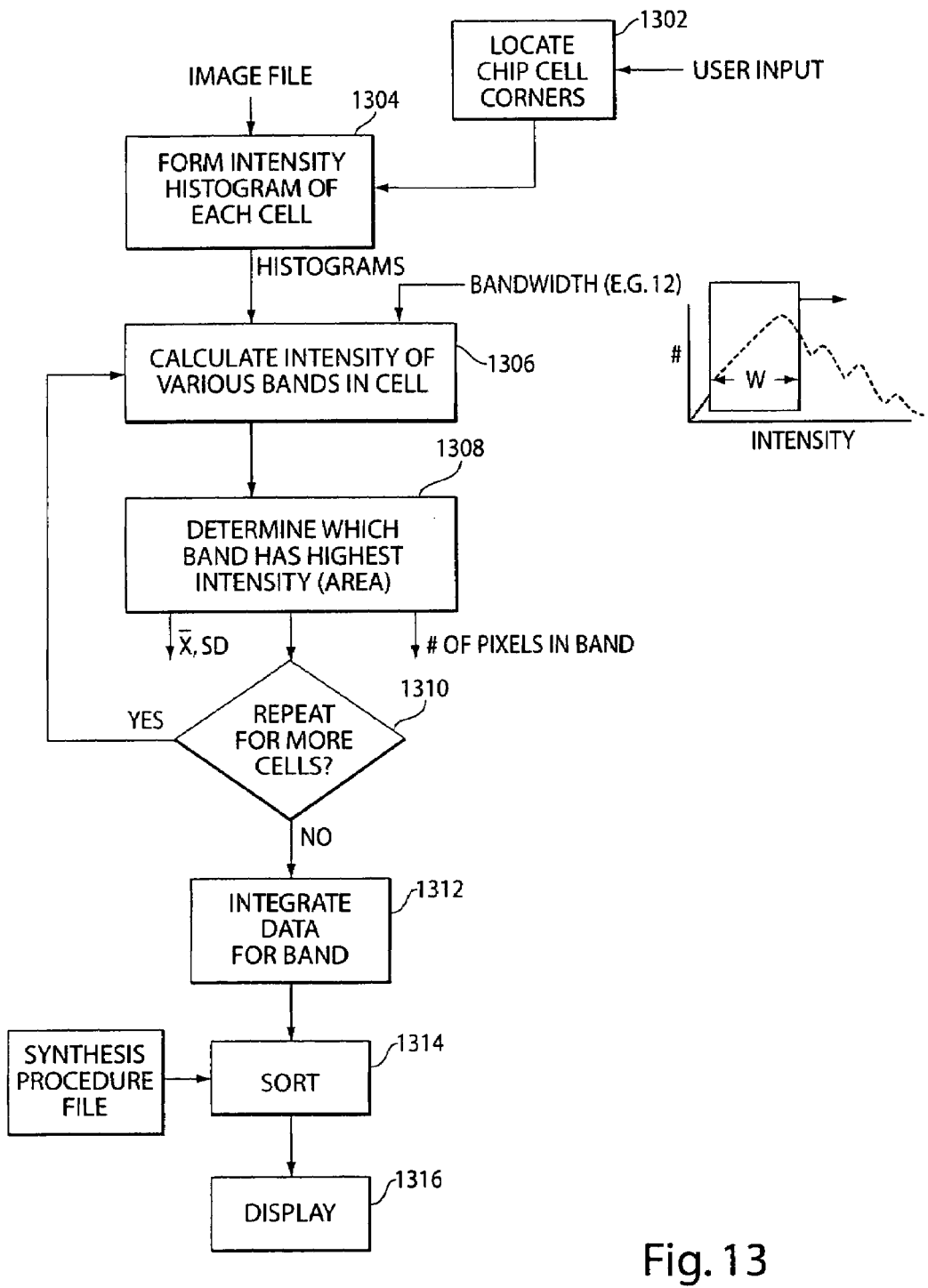
FIG. 13 is a flow chart illustrating operation of software for the data collection/analysis system.

FIG. 13 illustrates one embodiment of a system for removal of spurious data from a set of fluorescence data such as data used in affinity screening studies. A user or the system inputs data relating to the chip location and cell corners at step 1302. From this information and the image file, the system creates a computer representation of a histogram at step 1304, the histogram (at least in the form of a computer file) plotting number of data pixels versus intensity.

For each cell, a main data analysis loop is then performed. For each cell, at step 1306, the system calculates the total intensity or number of pixels for the bandwidth centered around varying intensity levels. For example, as shown in the plot to the right of step 1306, the system calculates the number of pixels within the band of width w. The system then "moves" this bandwidth to a higher center intensity, and again calculates the number or pixels the bandwidth. This process is repeated until the entire range of intensities have been scanned, and at step 1308 the system determines which band has the highest total number of pixels. The data within this bandwidth are used for further analysis. Assuming the bandwidth is selected to be reasonably small, this procedure will have the effect of eliminating spurious data located at the higher intensity levels. The system then repeats at step 1310 if all cells have been evaluated, or repeats for the next cell.

At step 1312 the system then integrates the data within the bandwidth for each of the selected cells, sorts the data at step 1314 using the synthesis procedure file, and displays the data to a user on, for example, a video display or a printer.

V. Representative Applications

A. Oligonucleotide Synthesis

The generality of light directed spatially addressable parallel chemical synthesis is demonstrated by application to nucleic acid synthesis.

1. EXAMPLE

Light activated formation of a thymidine-cytidine dimer was carried out. A three dimensional representation of a fluorescence scan showing a checkboard pattern generated by the light-directed synthesis of a dinucleotide is shown in FIG. 8. 5'-nitroveratryl thymidine was attached to a synthesis substrate through the 3' hydroxyl group. The nitroveratryl protecting groups were removed by illumination through a 500 mm checkerboard mask. The substrate was then treated with phosphoramidite activated 2'-deoxycytidine. In order to follow the reaction fluorometrically, the deoxycycidine had been modified with an FMOC protected aminohexyl linker attached to the exocyclic amine (5'-O-dimethoxytrityl-4-N-(6-N-fluorenylmethylcarbamoyl-hexylcarboxy)-2'-deoxycytidine). After removal of the FMOC protecting group with base, the regions which contained the dinucleotide were fluorescently labelled by treatment of the substrate with 1 mM FITC in DMF for one hour.

Figure 14:
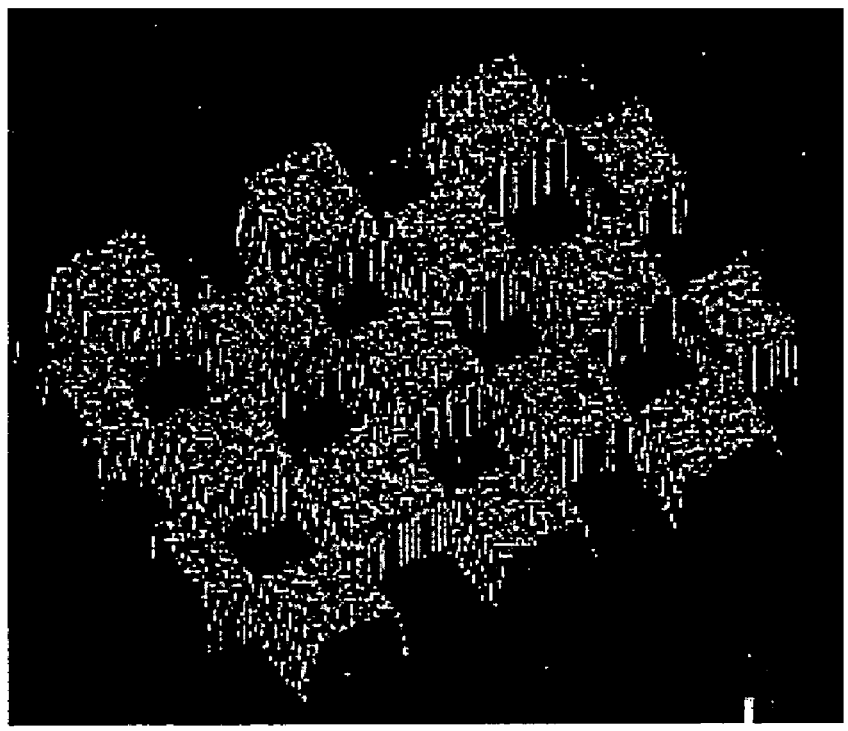
FIG. 14 illustrates a three-dimensional plot of intensity versus position for light directed synthesis of a dinucleotide.

The three-dimensional representation of the fluorescent intensity data in FIG. 14 clearly reproduces the checkerboard illumination pattern used during photolysis of the substrate. This result demonstrates that oligonucleotidesas well as peptides can be synthesized by the light-directed method.

VI. Conclusion

The inventions herein provide a new approach for the simultaneous synthesis of a large number of compounds. The method can be applied whenever one has chemical building blocks that can be coupled in a solid-phase format, and when light can be used to generate a reactive group.

The above description is illustrative and not restrictive. Many variations of the invention will become apparent to those of skill in the art upon review of this disclosure. Merely by way of example, while the invention is illustrated primarily with regard to peptide and nucleotide synthesis, the invention is not so limited. The scope of the invention should, therefore, be determined not with reference to the above description, but instead should be determined with reference to the appended claims along with their full scope of equivalents.

What is claimed is:

1. A compound having a photoremovable protecting group covalently attached to a C-3' or C-5' oxygen atom, wherein said compound is selected from the group consisting of a natural or unnatural nucleoside or a natural or unnatural nucleoside having an activated phosphorus group.

2. A compound of claim 1, wherein said oxygen atom is a C-3' oxygen of a ribonucleoside phosphoramidite or a ribonucleoside H-phosphonate.

3. A compound of claim 2, wherein said oxygen atom is a C-3' oxygen of a deoxyribonucleoside phosphoramidite or a deoxyribonucleoside H-phosphonate.

4. A compound of claim 1, wherein said oxygen atom is a C-3' oxygen of a natural nucleoside phosphoramidite.

5. A compound of claim 1, having the formula:

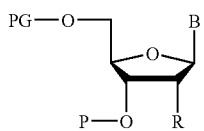

wherein

B is selected from the group consisting of natural or synthetic adenine, natural or synthetic guanine, natural or synthetic thymine, natural or synthetic cytosine, and natural or synthetic uracil;

R is selected from the group consisting of hydrogen, protected hydroxy, halogen and alkoxy;

P is an activated phosphorus group, and

PG is photoremovable protecting group selected from the group consisting of NVOC, MeNPOC, NPOC, MeN-VOC and pyrenylmethyloxycarbonyl.

6. A compound of claim 5, wherein R is hydrogen or protected hydroxy.

7. A compound of claim 5, wherein P is selected from the group consisting of N,N-dialkyl-O-methylphosphoramidite, phosphochloridite, an H-phosphonate group and an N,N-dialkyl-O-(2-cyanoethyl)phosphoramidite group.

8. A compound of claim 5, wherein B is selected from the group consisting of adenine, thymine, uracil, cytosine and guanine.

9. A compound of claim 5, wherein B is selected from the group consisting of adenine, thymine, uracil, cytosine and guanine, R is hydrogen or protected hydroxy, or alkoxy, P is an N,N-dialkyl-O-(2-cyanoethyl)phosphoramidite group.

10. A compound of claim 1, having the formula:

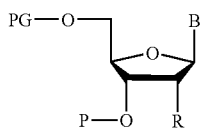

wherein
- B is selected from the group consisting of natural or synthetic adenine, natural or synthetic guanine, natural or synthetic thymine, natural or synthetic cytosine, and natural or synthetic uracil;
- R is selected from the group consisting of hydrogen, protected hydroxy, halogen and alkoxy;
- P is an activated phosphorus group, and
- PG is photoremovable protecting group selected from the group consisting of NVOC, MeNPOC, NPOC, MeNVOC and pyrenylmethyloxycarbonyl.

11. A compound of claim 10, wherein R is hydrogen or protected hydroxy.

12. A compound of claim 10, wherein P is N,N-dialkyl-O-methylphosphoramidite, or phosphochloridite, or an H-phosphonate group or an N,N-dialkvl-O-(2-cyanoethyl) phosphoramidite group.

13. A compound of claim 10, wherein B is selected from the group consisting of adenine, thymine, uracil, cytosine and guanine.

14. A compound of claim 10, wherein B is selected from the group consisting of adenine, thymine, uracil, cytosine and guanine, R is hydrogen or protected hydroxy, or alkoxy, P is an N,N-dialkyl-O-(2-cyanoethyl)phosphoramidite group.

15. A method for preparing a compound of claim 1, said method comprising attaching a photoremovable protecting group to the C-3' or C-5' oxygen atom of a natural or unnatural nucleoside and subsequently attaching an activated phosphorous group to the remaining C-3' or C-5' oxygen atom.

16. A method of claim 15, wherein said compound is selected from the group consisting of natural nucleoside phosphoramidites and natural nucleoside H-phosphonates.

17. A method of claim 15, wherein said compound is selected from the group consisting of natural deoxyribonucleoside phosphoramidites.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 1

Tyr Gly Gly Phe Leu
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 2

Pro Gly Gly Phe Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic sequence for description of method

<400> SEQUENCE: 3

Tyr Gly Ala Phe Leu Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 4

Tyr Gly Ala Phe Ser
1               5

<210> SEQ ID NO 5
```

```
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 5

Tyr Gly Ala Phe Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic sequence for description of method

<400> SEQUENCE: 6

Tyr Gly Gly Phe Leu Ser
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic sequence for description of method

<400> SEQUENCE: 7

Tyr Gly Ala Phe
1

<210> SEQ ID NO 8
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 8

Tyr Gly Ala Leu Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 9

Tyr Gly Gly Phe Ser
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic sequence for description of method

<400> SEQUENCE: 10

Tyr Gly Ala Leu
1

<210> SEQ ID NO 11
<211> LENGTH: 6
```

```
<212> TYPE: PRT
<213> ORGANISM: Artificial Sequence
<220> FEATURE:
<223> OTHER INFORMATION: Synthetic sequence for description of method

<400> SEQUENCE: 11

Tyr Gly Ala Phe Leu Phe
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 12

Tyr Gly Ala Phe Phe
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 13

Tyr Gly Gly Leu Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic sequence for description of method

<400> SEQUENCE: 14

Tyr Gly Ala Phe Ser Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic sequence for description of method

<400> SEQUENCE: 15

Tyr Gly Ala Phe Leu Ser Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic sequence for description of method

<400> SEQUENCE: 16

Tyr Gly Ala Phe Met Gln
1               5

<210> SEQ ID NO 17
<211> LENGTH: 5
<212> TYPE: PRT
```

```
<213> ORGANISM: Artificial Sequence
<220> FEATURE:
<223> OTHER INFORMATION: Synthetic sequence for description of method

<400> SEQUENCE: 17

Tyr Gly Ala Phe Met
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 18

Tyr Gly Ala Phe Gln
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic sequence for description of method

<400> SEQUENCE: 19

Tyr Gly Gly Phe Met
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic sequence for description of method

<400> SEQUENCE: 20

Gly Gly Phe Leu
1
```